US006506747B1

(12) United States Patent
Betageri et al.

(10) Patent No.: US 6,506,747 B1
(45) Date of Patent: Jan. 14, 2003

(54) SUBSTITUTED 1-(4-AMINOPHENYL) PYRAZOLES AND THEIR USE AS ANTI-INFLAMMATORY AGENTS

(75) Inventors: Rajashekhar Betageri, Bethel, CT (US); Charles L. Cywin, Bethel, CT (US); Karl Hargrave, Brookfield, CT (US); Mary Ann Hoermann, Holmes, NY (US); Thomas M. Kirrane, Danbury, CT (US); Thomas M. Parks, San Mateo, CA (US); Usha R. Patel, Brookfield, CT (US); John R. Proudfoot, Newtown, CT (US); Rajiv Sharma, Ridgefield, CT (US); Sanxing Sun, Danbury, CT (US); Xiao-Jun Wang, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/324,933

(22) Filed: Jun. 3, 1999

Related U.S. Application Data

(60) Provisional application No. 60/088,154, filed on Jun. 5, 1998.

(51) Int. Cl.$^7$ .................... A61K 31/535; C07D 263/30; C07D 241/36; C07D 417/00; C07D 413/00

(52) U.S. Cl. .................... 514/228.8; 514/307; 514/300; 514/340; 548/235; 544/353; 544/60; 544/132

(58) Field of Search ............................. 548/375.1, 235; 514/336, 341, 300, 340, 307; 544/238, 253, 333, 366, 132, 60, 376.1, 353; 546/275.7, 144; 540/488; 549/376.1

(56) References Cited

FOREIGN PATENT DOCUMENTS

WO WO 99/19303 * 4/1999

OTHER PUBLICATIONS

Vaz et al., "3, 5, 5–Trimethyl–1–aryl–2–pyrazolines biologically active agents", Chemical Abstracts 86: 5363f, vol. 86, p. 464, 1977.*

* cited by examiner

*Primary Examiner*—Alan L. Rotman
*Assistant Examiner*—Binta Robinson
(74) *Attorney, Agent, or Firm*—Robert P. Raymond; Mary-Ellen M. Devlin; Alan R. Stempel

(57) ABSTRACT

1-(4-aminophenyl)pyrazoles optionally substituted on the 3- and 5-positions of the pyrazole ring and on the amino group at the 4-position of the phenyl ring are disclosed and described, which pyrazoles inhibit IL-2 production in T-lymphocytes.

15 Claims, No Drawings

SUBSTITUTED 1-(4-AMINOPHENYL) PYRAZOLES AND THEIR USE AS ANTI-INFLAMMATORY AGENTS

This application claims the benefit of Provisional Application Serial No. 60/088,154 filed Jun. 5, 1998.

BACKGROUND OF THE INVENTION

It has been well established that T-cells play an important role in regulating immune response (F. Powrie and R. L. Coffman, *Immunol. Today*, 14, p. 270 (1993)). Indeed, activation of T-cells is often the initiating event in many inflammatory and autoimmune diseases. IL-2 is an autocrine growth factor which plays an essential role in the regulation of T-cell activation and proliferation. Clinical studies have shown that interference with IL-2 activity effectively suppresses immune response in vivo (T. A. Waldmann, *Immunol. Today*, 14, 270 (1993)). Accordingly, agents which inhibit IL-2 production are therapeutically useful for selectively suppressing immune response in a patient in need of such immunosuppression.

Previously, others have attempted to interfere with the activity of IL-2 by using cytokine antagonists, monoclonal antibodies, toxins and other biologics which seek to prevent IL-2 from binding to its receptor (G. Mazur and I. Frydecka, *Acta Haematol. Pol.*, 24(4), p. 307 (1993)). More recently, others have attempted to inhibit IL-2 production at the T cell level, for example by blocking the expression of IL-2 mRNA with glucocorticoids or cyclosporin A. However, to date, the reported compounds suffer from several disadvantages such as low potency, poor in vivo activity, toxicity and poor oral bioavailability. Accordingly, a need exists for compounds that can effectively inhibit IL-2 production for preventing and treating immune disorders.

A number of 3,5-disubstituted-1-(4-substituted) phenypyrazoles are available commercially or are known in the literature. These include N-{4-[3,5-bis(trifluoromethyl) pyrazol-1-yl]phenyl}-4-chlorobenzamide, N-{4-[3,5-bis (trifluoromethyl)pyrazol-1-yl]phenyl}-4-trifluoromethyoxybenzamid,e, N-{4-[3,5-bis (trifluoromethyl)pyrazol-1-yl]phenyl}-3,5-dimethylisoxazole-4-carboxamide, N-{4-[3,5-bis (trifluoromethyl)pyrazol-1-yl]phenyl}-4-methyl-1,2,3-thiadiazole-5-carboxamide, N-{4-[3,5-bis(trifluoromethyl) pyrazol-1-yl]phenyl}-N'-(3,5-dichlorophenyl)urea, N-{4-[3,5-bis(trifluoromethyl)pyrazol-1-yl]phenyl}-N'-(3,5-difluorophenyl)urea, and N-{4-[3,5-bis(trifluoromethyl) pyrazol-1-yl]phenyl}-N'-n-propylurea which are available commercially as chemical intermediates from Maybridge Chemical Company Ltd., Trevillett, Tintagel, Cornwall PL34 OHW, UK.

N-[4-(3,5-dimethylpyrazol-1-yl)phenyl]acetamide (Bouchet and Coquelet, Bull. Soc. Chim.

Fr. 1976, 195), N-[4-(3-methyl-5-chloropyrazol-1-yl) phenyl]acetamide (Michaelis and Behn, Chem. Ber. 1900, 33, 2602), N-[4-(3-methyl-5-(methylthio)pyrazol-1-yl) phenyl]acetamide (Michaelis, Justus Liebigs Ann. Chem., 1911, 378, 346), N-[4-(3-methyl-5-phenylpyrazol-1-yl) phenyl]benzamide (Barry et al., J. Chem. Soc. 1956, 4974), N-[4-(3-methyl-5-ethoxypyrazol-1-yl)phenyl]acetamide (Hoechster Farbw., DE 92990), N-[4-(3,5-dimethylpyrazol-1-yl)phenyl]-4-methoxybenzylamine, N-[4-(3,5-dimethylpyrazol-1-yl)phenyl]-4-nitrobenzylamine (Fernandes et al. J. Indian Chem. Soc. 1977, 54, 923), 4-(3,5-dimethylpyrazol-1-yl)-N-methylbenzamide (Wright et al., J. Med. Chem. 1964, 7, 102), 4-methoxy- and 4-nitro-alpha-{[4-(3,5-dimethylpyrazol-1-yl)phenyl] amino}benzeneacetonitrile and N-[4-(3,5-dimethylpyrazol-1-yl)phenyl]-4-methoxy-(and 4-nitro)-benzenemethaneamine (Fernandes et al., J. Indian Chem. Soc. 1977, 54, 923) are described in the chemical or patent literature. In no case is antiinflammatory activity or ability to inhibit IL-2 production associated with or described for any of these compounds.

1-(4-Methylaminophenyl)-5-(4-methylsulfonylphenyl)-3-trifluoromethylpyrazole, 1-(4-methylaminophenyl)-5-(4-methylsulfonylphenyl)-3-difluoromethylpyrazole (K. Tsuji et al., Chem. Pharm. Bull., 1997, 45, 1475) and 3-cyano-1-(4-methylaminophenyl)-5-(4-methylsulfonylphenyl) pyrazole and 3-cyano-1-(4-ethylaminophenyl)-5-(4-methylsulfonylphenyl)pyrazole (K. Tsuji et al., Chem Pharm. Bull. 1997, 45, 987) are among several compounds described as having antiinflammatory activity due to their ability to inhibit an isoform of cyclooxygenase referred to as COX-2. In neither case is the inhibition of IL-2 production mentioned.

Among a series of substituted pyrazoles having antiinflammatory activity described by M. Matsuo (EP 418845 A1) are 1-[4-($C_1$–$C_6$ alkylamino)phenyl]- and [4-($C_1$–$C_6$ acylamino)phenyl]pyrazoles substituted on the pyrazole on either the 3-,4-, or 5-position with $CF_3$, halogen, dimethylaminomethyl, CN, $C_{1-6}$ alkylthio, or esterified carboxy and on another of the 3-, 4-, or 5-positions with a substituted aryl or heteroaryl ring. No mention is made of inhibition of IL-2 production.

BRIEF SUMMARY OF THE INVENTION

The compounds of this invention are 1-(4-aminophenyl) pyrazoles optionally substituted on the 3- and 5-positions of the pyrazole ring and on the amino group on the 4-position of the phenyl ring having antiinflammatory activity by virtue of their ability to inhibit IL-2 production in T-lymphocytes.

In its broadest generic aspect, the invention comprises 1(4-amninophenyl)pyrazoles of Formula I Formula I

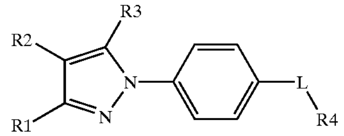

wherein:

$R_1$ and $R_3$ are the same or different and each is $CF_3$, halogen, CN, $C_{1-8}$ alkyl or branched alkyl or $C_{1-8}$ alkenyl or branched alkenyl or $C_{3-8}$ cycloalkyl optionally substituted with OH, CN or methoxy; $C_{1-8}$ alkoxy, $C_{1-4}$ alkyloxyalkyl, $C_{1-8}$ alkylthio, $C_{1-4}$ alkylthioalkyl, $C_{1-8}$ dialkylamino, $C_{1-4}$ dialkylaminoalkyl, $CO_2R_5$ where $R_5$ is $C_{1-4}$ alkyl or $C_{1-4}$ alkenyl optionally substituted with carbocyclyl or heterocyclyl; aryl or heterocyclyl connected to the pyrazole in any position that makes a stable bond, optionally substituted with halogen, $C_{1-4}$ alkyl, $C_{1-4}$ alkenyl, CN, $Me_2N$, $CO_2Me$, OMe, aryl, heterocyclyl or $R_5$.

$R_2$ is H, halogen, or methyl.

L is —NHC(O)—, —NHC(O)O—, —NHC(O)C(O)—, —NHC(S)—, —NH—, —NHC(O)NH, NHC(S)NH, $NHCH_2$, —NHCH($R_6$)—, where $R_6$ is H, CN, $C_{1-6}$ alkyl, $C_{1-6}$ alkyloxyoalkyl $C_{1-6}$ alkythioalkyl, $C_{1-6}$ alkylsulfinylalkyl, $C_{1-6}$ alkysulfonylalkyl, $C_{3-6}$ cycloalkyl, or heterocyclyl or aryl optionally substituted with a halogen, $C_{1-4}$ alkyl, CN, $Me_2N$, $CO_2Me$ or OMe, or —NHC($R_6$)— lower alkyl.

$R_4$ is $C_{1-8}$ alkyl, $C_{1-8}$ alkyloxy, $C_{1-8}$ alkylthio, $C_{1-8}$ alkylamino, $C_{1-4}$ alkoxyalkyl, $C_{1-4}$ alkylthioalkyl, $C_{1-4}$ alkylaminoalkyl, $C_{1-4}$ dialkylalkylaminoalkyl, carbocyclyl or heterocyclyl, optionally substituted with one or more halogen, —CN, —$NO_2$, $SO_2NH_2$, or $R_7$ where $R_7$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkylsulfinylalkyl, $C_{1-6}$ alkylsulfonylalkyl or $C_{2-6}$ alkynyl, optionally substituted with halogen, OH, alkyloxy, CN, COO-lower alkyl, —CONH-lower alkyl, —CON(lower alkyl)$_2$, dialkylamino, phenyl or heterocylcyl; $CO_2R_7$, —N($R_7$)$_2$, —NH($R_7$), —C(O)$R_7$, —$OR^7$, S(O)$_n$$R_7$ where n is 0, 1 or 2, —$SO_2NHR_7$, —$SO_2N(R_7)_2$.

DETAILED DESCRIPTION OF THE INVENTION

In order that the invention herein described may be more fully understood, the following detailed description is set forth. As used herein, the following abbreviations are used:

BOC or t-BOC is tertiary butoxycarbonyl

DMAP is 4-dimethylamino pyridine

Bu is butyl

DIBAL is diisobutylaluminum hydride

DMF is dimethylformamide

Et is ethyl

Me is methyl

Oxz is oxazole

Ph is phenyl

Pr is propyl

Py is pyridine

PyBOP is Benzotriazole-1-yl-oxy-tris-pyrrolidino-phosphonium hexafluorophosphate Th is thiophene THF is tetrahydrofuran Thz is thiazole Rt is room temperature EDC is 1-(3-dimethylaminopropyl)-3-ethylcarbodimide hydrochloride.

Also, as used herein, each of the following terms, used alone or in conjunction with other terms, are defined as follows (except where noted to the contrary):

The term "alkyl" refers to a saturated aliphatic radical containing from one to ten carbon atoms. "Alkyl" refers to both branched and unbranched alkyl groups. Preferred alkyl groups are straight chain alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms. "Alkyl", as used herein, includes unsubstituted alkyl radicals, those radicals that are partially or fully halogenated and those radicals substituted with one to four, preferably one or two, substituents selected from amino, cyano, nitro, methoxy, ethoxy and hydroxy. The term "cycloalkyl" refers to the cyclic analog of an alkyl group, as defined above. Preferred cycloalkyl groups are saturated cycloalkyl groups containing from three to eight carbon atoms, and more preferably three to six carbon atoms. "Alkyl" and "cycloalkyl", as used herein, include unsubstituted alkyl and cycloalkyl radicals, those radicals that are partially or fully halogenated and those radicals substituted with one to four, preferably one or two, substituents selected from halo, amino, cyano, nitro, methoxy, ethoxy and hydroxy. It should be understood that any combination term using an "alk" or "alkyl" prefix refers to analogs according to the above definition of "alkyl". For example, terms such as "alkoxy", "allkythio" refer to alkyl groups linked to a second group via an oxygen or sulfur atom.

The terms "alkenyl" and "alkynyl" refer to a mono- or polyunsaturated aliphatic hydrocarbon radical containing from two to twelve carbon atoms, containing at least one double or triple bond, respectively. "Alkenyl" and "alkynyl" refer to both ranched and unbranched alkenyl and alkynyl groups. Preferred alkenyl and alkynyl groups are straight chain alkenyl or alkynyl groups containing from two to eight carbon atoms and branched alkenyl or alkynyl groups containing from five to ten carbon atoms. More preferred alkenyl and alkynyl groups are straight chain alkenyl or alkynyl groups containing from two to six carbon atoms and branched alkenyl or alkynyl groups containing from five to eight carbon atoms. The term "cycloalkenyl" refers to the cyclic analog of an alkenyl group, as defined above. Preferred cycloalkenyls include cycloalkenyl rings containing from three to eight carbon atoms, and more preferably, from three to six carbon atoms. "Alkenyl", "alkynyl" and "cycloalkenyl", as used herein, include unsubstituted alkenyl or alkynyl radicals, those radicals that are partially or fully halogenated and those radicals substituted with one to four, preferably one or two, substituents selected from halo, amino, cyano, nitro, methoxy, ethoxy and hydroxy.

The term "aryl" refers to phenyl and naphthyl, phenyl and naphthyl that are partially or fully halogenated and phenyl and naphthyl substituted with halo, alkyl, hydroxyl, nitro, —COOH, —CO(lower alkoxy), —CO(lower alkyl), amino, alkylamino, dialkylamino, alkoxy, —NCOH, —NCO(lower alkyl), —$NSO_2$—Ph(halo)$_{0-3}$, Ph, —O—Ph; naphthyl, —O-naphthyl, pyrrolyl, pyrrolyl substituted with lower alkyl, pyridyl, pyridinyl, pyrazinyl, pyrimidinyl and pyridazinyl.

The term "carboxy alkyl" refers to an alkyl radical containing a —COOH substituent.

The term "halo" refers to a halogen radical selected from fluoro, chloro, bromo or iodo. Preferred halo groups are fluoro, chloro and bromo.

The term "carbocyclyl" refers to a stable 3–8 membered (but preferably, 5 or 6 membered) monocyclic or 7–11 membered bicyclic radical which may be either saturated or unsaturated, aromatic or non-aromatic. Preferred carbocycles include, for example, phenyl, naphthyl, cyclopropyl, cyclobutyl, cyclopentyl, cyclohexyl, cycloheptyl, cyclopentenyl, cyclohexenyl, cycloheptenyl, indanyl, indenyl, dihydronaphthyl and tetrahydronaphthyl. "Carbocyclyl" refers to unsubstituted carbocyclic radicals, those radicals that are partially or fiully halogenated and those radicals substituted with alkyl; hydroxyl; nitro; —COOH; —CO(lower alkoxy); —CO(lower alkyl); amino; alkylamino; dialkylamino; alkoxy, —NCHO; —NCO(lower alkyl); —$NSO_2$-Ph(halo)$_{0-3}$, Ph; —O—Ph; naphthyl; —O-naphthyl; pyrrolyl; pyrrolyl substituted with lower alkyl; pyridyl; pyridinyl; pyrazinyl; pyrimidinyl and pydazinyl.

The term "heterocycle" refers to a stable 5–8 membered (but preferably, 5 or 6 membered) monocyclic or 8–11 membered bicyclic heterocycle radical which may be either saturated or unsaturated, aromatic or non-aromatic, and which may be optionally benzo- or pyridofused if monocyclic. Each heterocycle consists of carbon atoms and from 1 to 4 heteroatoms selected from the group consisting of nitrogen, oxygen and sulfur. As used herein, “nitrogen” and “sulfur” include any oxidized form of nitrogen and sulfur and the quaternized form of any basic nitrogen. The heterocycle may be attached by any atom of the cycle, which results in the creation of a stable structure. Preferred heterocycles include, for example, benzimidazolyl, furyl; imidazolyl, imidazolinyl, imidazolidinyl, quinolinyl, isoquinolinyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiomorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazoyl, benzodioxolyl, tetrahydrothiophenyl and sulfolanyl. Most preferred heterocycles of this invention include imidazolyl, pyridyl, pyrrolyl, pyrazolyl, piperidinyl, morpholinyl, furyl, thienyl, thiazolyl and the benzo- and pyrido-flised derivatives thereof. “Heterocyclyl” refers to unsubstituted heterocycle radicals, those radicals that are partially or fully halogenated and those radicals substituted with alkyl; hydroxyl; nitro; —COOH; —CO(lower alkoxy); —CO(lower alkyl); amino; alkylamino; dialkylamino; alkoxy; —NCHO; —NCO(lower alkyl); —$NSO_2$—Ph $(halo)_{0-3}$, Ph; —O—Ph; naphthyl; —O-naphthyl; pyrrolyl; pyrrolyl substituted with lower alkyl; pyridyl; pyridinyl; pyrazinyl; pyrimidinyl and pyridazinyl.

The term “lower” used in conjunction with other terms (e.g., “alkyl”, “alkoxy” and the like) refers to a radical containing from one to six, preferably from one to five and more preferably, from one to four carbon atoms. For example, a “lower alkyl” group is a branched or unbranched alkyl radical containing from one to six carbon atoms.

The term “patient” refers to a warm-blooded animal, and preferably human.

The term “prevention” or “prophylaxis” refers to a measurable reduction in the likelihood of a patient acquiring a disease or disorder.

The term “treatment” refers to either the alleviation of the physical symptoms of a disease or an improvement in the physiological markers used to measure progression of a disease state.

The term “pharmaceutically acceptable carrier” or “pharmaceutically acceptable adjuvant” refers to a non-toxic carrier or adjuvant that may be administered to a patient together with a compound of this invention and which does not destroy the pharmacological activity of that compound.

The term “pharmaceutically effective amount” refers to an amount effective in suppressing the immunity of a patient in need of such treatment. Suppressed immunity can be readily measured by observing the degree of inhibition of IL-2 production in human T-cells (PBLS) by known techniques.

The term “prophylactically effective amount” refers to an amount effective in preventing or reducing the likelihood of initial onset or progression of an immune disorder in a patient susceptible to such disorder.

It should be understood that any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic center may be in the R or S configuration, or a combination of configurations.

The compounds of this invention are defined to include pharmaceutically acceptable derivatives thereof. A “pharmaceutically acceptable derivative” refers to any pharmaceutically acceptable salt, ester, or salt of an ester of a compound of this invention, or any other compound which, upon administration to a patient, is capable of providing (directly or indirectly) a compound of this invention, a pharmacologically active metabolite or pharmacologically active residue thereof.

Combinations of substituents and variables encompassed by this invention are only those that result in the formation of stable compounds. The term “stable” as used herein, refers to compounds which possess stability sufficient to permit manufacture and administration to a patient by conventional methods known in the art. Typically, such compounds are stable at a temperature of 40° C. or less, in the absence of moisture or other chemically reactive conditions, for at least a week.

The compounds of this invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, tosylate and undecanoate.

This invention relates to substituted 1-(4-aminophenyl) pyrazoles and analogs thereof that inhibit interleukin-2 (IL-2) production. In one embodiment, this invention relates to a novel class of substituted 1-(4-aminophenyl)pyrazoles and pharmaceutical compositions comprising these compounds. This invention also relates to methods for producing such novel substituted 1(4-aminophenyl)pyrazoles. Because of their selective immunomodulating properties, the compounds and pharmaceutical compositions of this invention are particularly well suited for preventing and treating immune disorders, including autoimmune disease, inflammatory disease, organ transplant rejection and other disorders associated with IL-2 mediated immune response.

The substituted 1(4-aminophenyl)pyrazoles of this invention are represented by Formula I Formula I

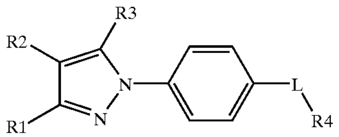

wherein:

$R_1$ and $R_3$ are the same or different and each is $CF_3$, halogen, CN, $C_{1-8}$ alkyl or branched alkyl or $C_{1-8}$ alkenyl or branched alkenyl or $C_{3-8}$ cycloalkyl optionally substituted with OH, CN or methoxy; $C_{1-8}$ alkoxy, $C_{1-4}$ alkyloxyalkyl, $C_{1-8}$ alkylthio, $C_{1-4}$ alkylthioalkyl, $C_{1-8}$ dialkylamino, $C_{1-4}$ dialkylaminoalkyl, $CO_2R_5$ where $R_5$ is $C_{1-4}$ alkyl or $C_{1-4}$ alkenyl optionally substituted with carbocyclyl or heterocyclyl; aryl or heterocyclyl connected to the pyrazole in any position that makes a stable bond, optionally substituted with halogen, $C_{1-4}$ alkyl, $C_{1-4}$ alkenyl, CN, $Me_2N$, $CO_2Me$, OMe, aryl, heterocyclyl or $R_5$.

$R_2$ is H, halogen or methyl.

L is —NHC(O)—, —NHC(O)O—, —NHC(O)C(O)—, —NHC(S)—, —NH—, —NHC(O)NH, NHC(S)NH, $NHCH_2$, —$NHCH(R_6)$—, where $R_6$ is H, CN, $C_{1-6}$ alkyl, $C_{1-6}$ alkyloxyoalkyl $C_{1-6}$ alkythioalkyl, $C_{1-6}$ alkylsulfinylalkyl, $C_{1-6}$ alkysulfonylalkyl, $C_{3-6}$ cycloalkyl, or heterocyclyl or aryl optionally substituted with a halogen, $C_{1-4}$ alkyl, CN, $Me_2N$, $CO_2Me$ or OMe, or —$NHC(R_6)$— lower alkyl.

$R_4$ is $C_{1-8}$ alkyl, $C_{1-8}$ alkyloxy, $C_{1-8}$ alkylthio, $C_{1-8}$ alkylamino, $C_{1-4}$ alkoxyalkyl, $C_{1-4}$ alkylthioalkyl, $C_{1-4}$ alkylaminoalkyl, $C_{1-4}$ dialkylalkylaminoalkyl, carbocyclyl or heterocyclyl, optionally substituted with one or more halogen, —CN, —$NO_2$, $SO_2NH_2$, or $R_7$ where $R_7$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkylsulfinylalkyl, $C_{1-6}$ alkylsulfonylalkyl or $C_{2-6}$ alkynyl, optionally substituted with halogen, OH, alkyloxy, CN, COO-lower alkyl, —CONH-lower alkyl, —CON(lower $alkyl)_2$, dialkylamino, phenyl or heterocylcyl; $CO_2R_7$, —$N(R_7)_2$, —$NH(R_7)$, —$C(O)R_7$, —$OR^7$, $S(O)_nR_7$ where n is 0, 1 or 2, —$SO_2NHR_7$, —$SO_2N(R_7)_2$.

Preferably, the novel substituted 1-(4-aminophenyl) pyrazoles of Formula I are those wherein:

$R_1$ is straight-chained, branched or cyclo-$C_{3-8}$ alkyl, alkenyl, or alkynyl; $C_{1-3}$ alkyloxyalkyl, $C_{1-5}$ alkyloxy, $C_{1-3}$alkylthioalkyl, $C_{1-5}$ alkylthio, $CF_3$; heterocyclyl or aryl optionally substituted with halogen, $C_{1-4}$ alkyl, CN, alkoxy or $Me_2N$;

$R_2$ is H; and $R_3$ is halogen, Me, Et, $CF_3$, CN, cyclopropyl, vinyl, SMe, OMe, heterocyclyl or aryl optionally substituted with halogen, $C_{1-4}$ alkyl, CN, alkoxy or $Me_2N$;

L is —NHC(O)—, —NH—, —NHC(O)NH, —C(O)NH, or —$NHCH(R_6)$—, where $R_6$ is H, $C_{1-4}$ alkyl, or CN and $R_4$ is $C_{1-6}$ alkyl, $C_{1-4}$ alkyloxyalkyl, $C_{1-4}$ alkylthioalkyl, cyclohexyl, cyclopentyl, indanyl, indolyl, phenyl, thienyl, naphthyl, isoxazolyl or pyridyl, optionally substituted with one or more halogen, —CN, —$NO_2$, $SO_2NH_2$, or $R_7$ where $R_7$ $C_{1-6}$ alkyl, $C_{2-6}$ alkenyl, $C_{1-6}$ alkyloxyalkyl, $C_{1-6}$ alkylthioalkyl, or $C_{2-6}$ alkynyl, optionally substituted with OH, CN, —COO-lower alkyl, —CONH-lower alkyl, —CON(lower $alkyl)_2$, dialkylamino, or heterocylcyl; $CO_2R_7$, —$N(R_7)_2$, —$NH(R_7)$, —$C(O)R_7$, —$OR_7$, $S(O)_nR_7$ where n is 0, 1 or 2, —$SO_2NHR_7$, —$SO_2N(R_7)_2$.

More preferred are novel substituted 1-(4-aminophenyl) pyrazoles of Formula I wherein:

$R_1$ is Et, i-Pr, t-Bu, cyclopentyl, $CF_3$, -OEt, $MeOCH_2$—, 2- or 3-tetrahydrofuranyl, 2-, 3-, or 4-pyridyl or 2-pyrazinyl;

$R_2$ is H;

$R_3$ is Halogen, CN, $CF_3$, Me, 5Me or Et;

L is —NHC(O)—, —NH— or —$NHCH_2$—; and $R_4$ is alkyl, cyclohexyl, cyclopentyl, indanyl, indolyl, phenyl, thienyl, naphthyl, or pyridyl, optionally substituted with one or more halogen, —CN, or $R_7$ where $R_7$ $C_{1-6}$ alkyl, $C_{2-6}$ alkenyl, $C_{1-6}$ alkyloxyalkyl, $C_{1-6}$ alkylthioalkyl, optionally substituted with OH, CN, or heterocylcyl; —$CO_2R_7$, —$N(R_7)_2$, —$NH(R_7)$, —C(O) $R_7$, or —$OR_7$.

Compounds of Formula I in which L is —NHC(O)— may be prepared by one of the methods outlined below. For example, a (4-aminophenyl)-3,5-disubstituted pyrazole 1 may be reacted with a carboxylic acid 2 under suitable coupling conditions known to one skilled in the art, for example EDC and a base catalyst such as N,N-dimethylaminopyridine in a suitable solvent such as methylene chloride acetonitrile or DMF (Method A). Alternatively, 1 could be coupled with an acid halide 3 in the presence of a suitable base such as triethylamine in a suitable solvent such as methylene chloride (Method B). In another alternative method, these compounds could be prepared by reacting a 4-(acetamido)phenylhydrazine 4 with a 1,5-disubstituted-2,4-pentanedione 5 in a suitable solvent such as acetic acid (Method C). If $R_1$ is different from $R_3$, then two different products may form using Method C, which may be separated by techniques such as chromatography known to those skilled in the art.

Method A

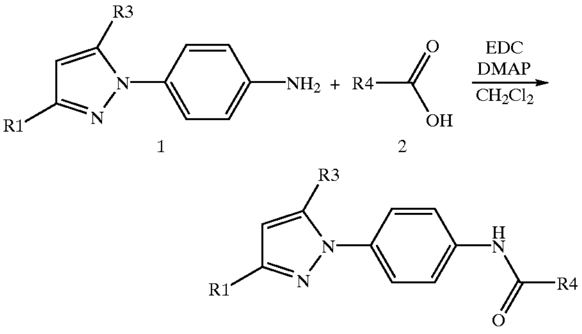

1
2

Method B

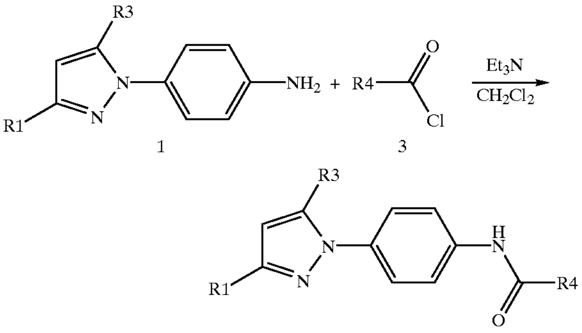

1
3

Method C

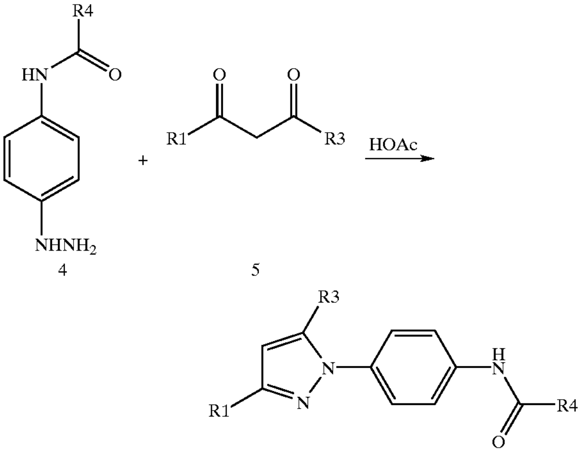

4
5

Compounds of Formula I in which L is —NH— and $R_4$ is a heteroaryl ring may be prepared, as illustrated below, by reaction of a (4-aminophenyl)-3,5-disubstituted pyrazole 1 with a heterocycle 6 containing a labile substituent such as a halogen, which may be displaced by nucleophilic substitution (Method D). The reaction may be carried out in a sealed tube or an open vessel, at ambient temperature or heated to 150° C. in a suitable solvent such as dioxane or THF. A base such as sodium bis-trimethylsilyl amide may be added to the reaction.

Method D

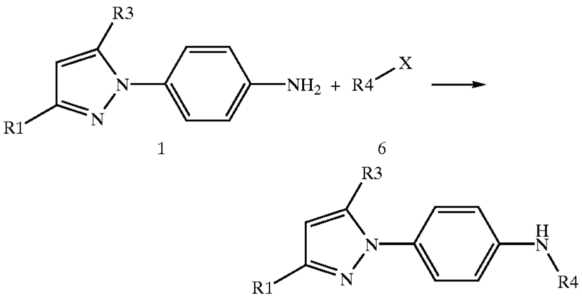

1 6

X is halogen or other leaving group

Compounds in which L is —NHC(O)NH— may be prepared by reaction of isocyanate 7 with an amine 8 in a suitable solvent such as methylene chloride or toluene (Method E). An amine such as triethylamine may be added. Alternatively, 1 could be reacted with an amine carbonyl chloride such as N-morpholine carbonyl chloride 9 in a suitable solvent such as methylene chloride (Method F).

Method E

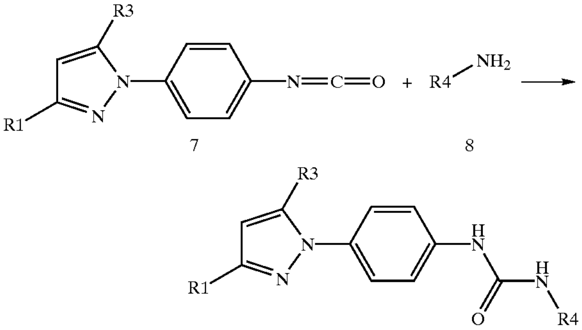

7 8

Method F

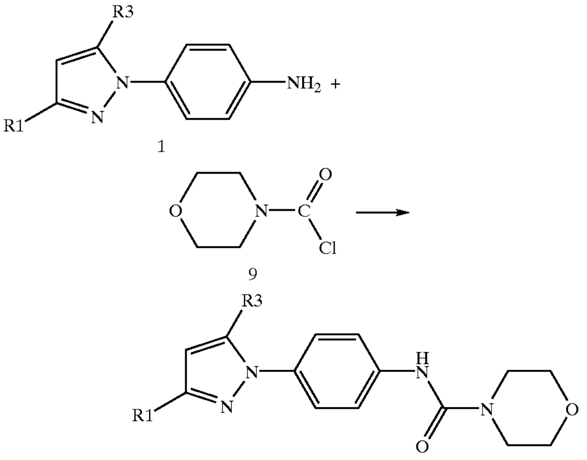

1

9

Methods by which compounds in which L is —NHCH($R_5$)— or —$NHCH_2$ may be prepared as illustrated below.

For example, these compounds may be prepared by reduction of the corresponding amide (L is —NHC(O)—) with a suitable reducing agent such as lithium aluminum hydride, in a suitable solvent such as THF or diethyl ether (Method G). Alternatively, amine 1 could react with an alkylating agent 10 (Method H) where X is a suitable leaving group such as a halogen. In another alternate procedure, amine 1 could react with an aldehyde 11, and the intermediate imine 12 reacted with a reducing agent such as sodium cyanoborohydride or sodium triacetoxyborohydride (Method I). Alternatively, 12 could be reacted with a nucleophile such as an alkyl or aryl lithium reagent (Method J).

Pyrazole intermediates used in the preparations of the compounds of the invention may be prepared by methods known in the chemical literature. Two general methods that may be used are illustrated below. For example, a disubstituted 1,3-dione 13 may be heated with 4-nitrophenylhydrazine in a suitable solvent such as ethanol to provide a 3,5-disubstituted 1-(4-nitrophenyl)pyrazole. If $R_1$ and $R_3$ are not equivalent, a mixture of two Method G

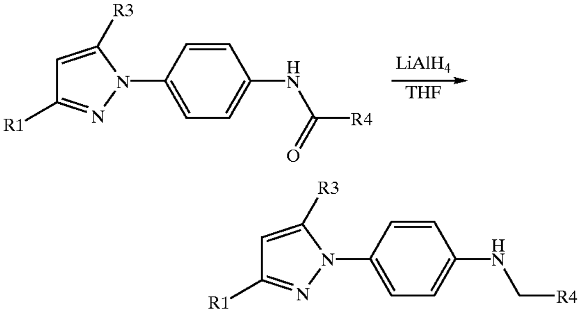

Method H

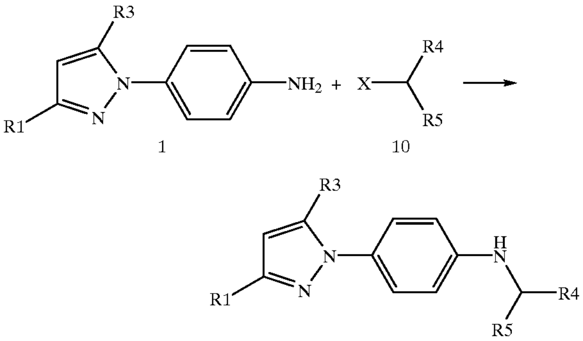

1 10

Methods I and J

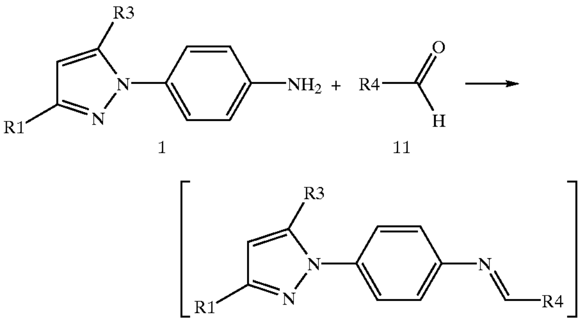

1 11

12

-continued

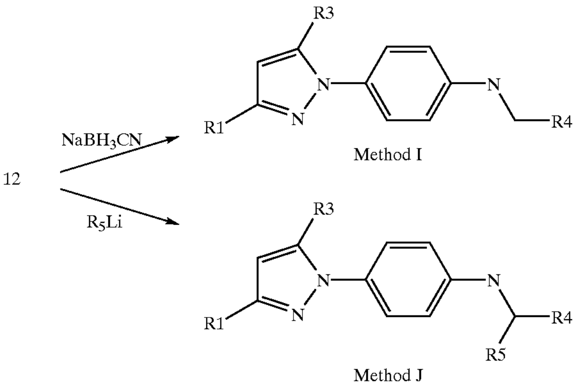

Method K

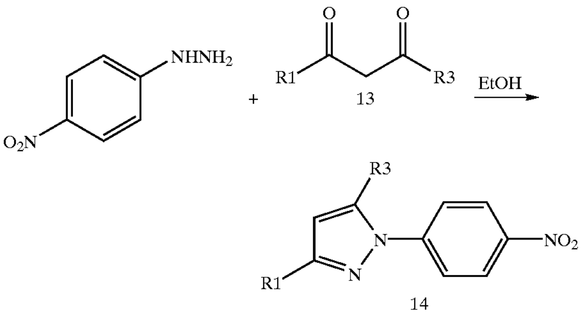

Method L

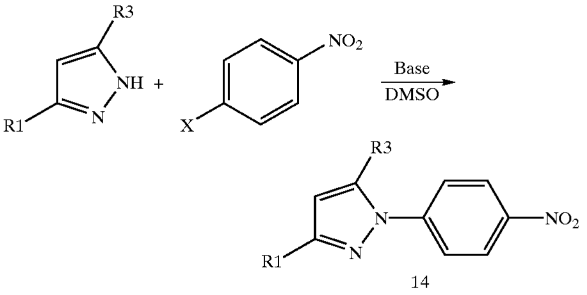

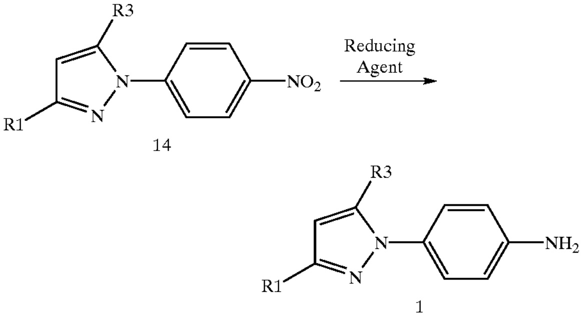

products may be obtained (Method K). Alternately, a 3,5-disubstituted pyrazole may be reacted with nitrobenzene substituted in the 4-position with a leaving group such as a halogen in the presence of a base (Method L). The nitrophenylpyrazoles produced by either method could then be reduced to aminophenyl pyrazoles by using a reducing agent such as $SnCl_2$ or hydrogen or a hydrogen source such as ammonium formate in the presence of a catalyst such as palladium.

Certain $R_1$ and $R_3$ can greatly enhance the regioselectivity of the reaction to produce 14 by Method L. If $R_1$ is aryl, and preferably an electron deficient aryl, such as pyridine, or a phenyl with an electron withdrawing group such as —CN or $NO_2$, and $R_3$ is alkyl, preferably ethyl or methyl, high regioselectivity to give 14 as the major product compared to regioisomer 14a can be obtained (Scheme I) by reacting the substituted pyrazole with a nitrobenzene substituted in the 4-position with a leaving group, preferably fluorine in a suitable solvent, preferably DMSO, with a suitable base, preferably t-BuOK at about 75° C. for about one hour.

Scheme I

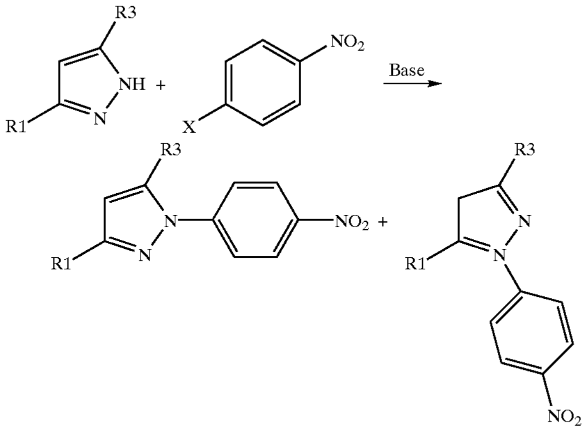

14 Major Product

14a Minor Product

One may obtain 14 where $R_1$ is alkyl in a regioselective manner using Method L, by employing a substituted pyrazole where $R_1$ contains a chelating group, preferably oxygen, and then converting $R_1$ in the resulting product 14 to an alkyl group. For example, as illustrated in Scheme I, reacting a substituted pyrazole where $R_1$ is an alkylcarbonyl, preferably —C(O)$CH_3$, or an ether such as CH(R)OR', where R is preferably hydrogen or methyl, and R' is a suitable protecting group, preferably tetrahydropyranyl (THP) with a nitrobenzene substituted in the 4-position with a leaving group, preferably fluorine, in a suitable solvent, such as THF or DMSO, preferably THF in the presence of a suitable base such as t-BuOK, n-BuLi, sodium hydride, or ethyl magnesium bromide, preferably t-BuOK, one obtains regioisomer 14 as the major product.

$R_1$ may be converted to an alkyl group as illustrated in Scheme II

Scheme II

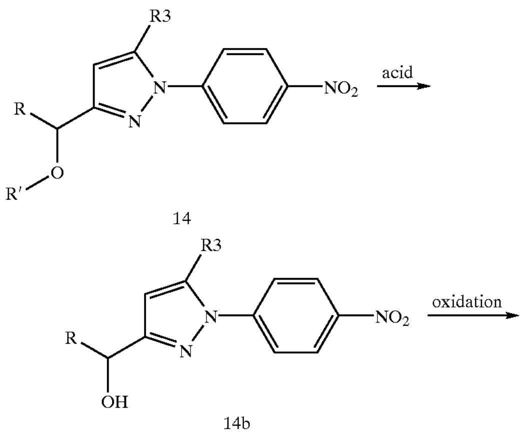

-continued

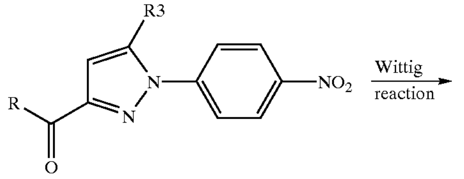

14c

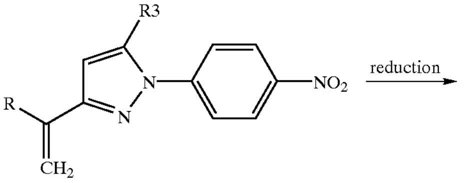

14d

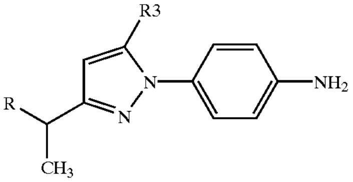

15

As shown for 14 where $R_1$ is an ether and R'=THP, reaction with an acid, such as p-toluenesulfonic acid in a suitable solvent such as aqueous methanol provides alcohol 14b. Treatment with a suitable oxidizing agent such as pyridinium chlorochromate provides ketone 14c. Wittig reaction with a phosphorous ylide derived from methyltriphenylphosphonium bromide provides olefin 14d. Reaction under reducing conditions, such as hydrogenation in the presence of a palladium catalyst provides 15. Starting with 14 where $R_1$ is an alkylcarbonyl, one would proceed beginning with 14c.

Other methods may also be used for synthesis of pyrazole intermediates. Some of these approaches are illustrated below. 5-Dimethylaminomethylpyrazole 16 may be prepared by a general method (Method M) described in the chemical literature (Tang and Method M

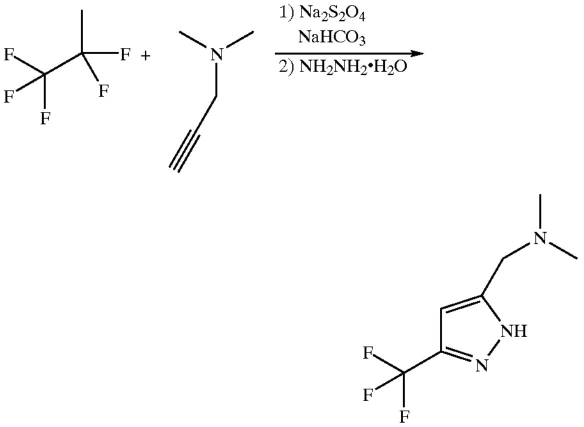

16

-continued

Method N

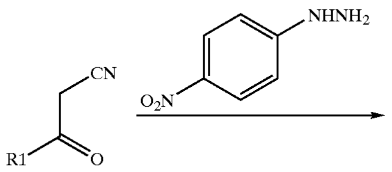

17

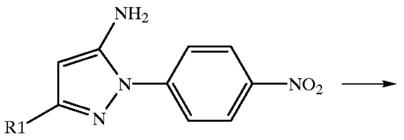

18

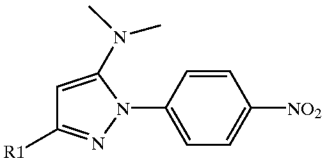

19

Method O

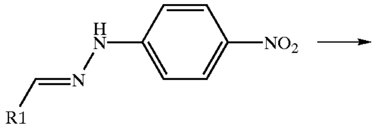

20

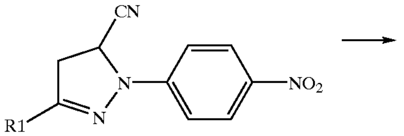

21

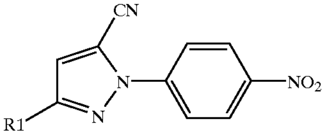

22

Hu, 1994, J. Chem. Soc. Chem. Commun., 631). The 1-(4-aminophenyl)pyrazole analog of 16 may then be prepared as described in Method L. Using nitrile 17 and 4-nitrophenylhydrazine, the 5-amino and 5-disubstituted aminopyrazoles 18 and 19 can be prepared (Method N). Reaction of hydrazone 20, with acrylonitrile and iodobenzene diacetate, followed by oxidation of pyrazoline 21 provides 5-cyanopyrazoles 22 (Method O). The nitrophenylpyrazoles described in Methods N and O can then be reduced to the aminophenylpyrazoles as described in Method L.

5-Cyanopyrazoles may also be obtained by method P below.

Method P

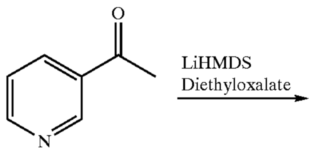

-continued

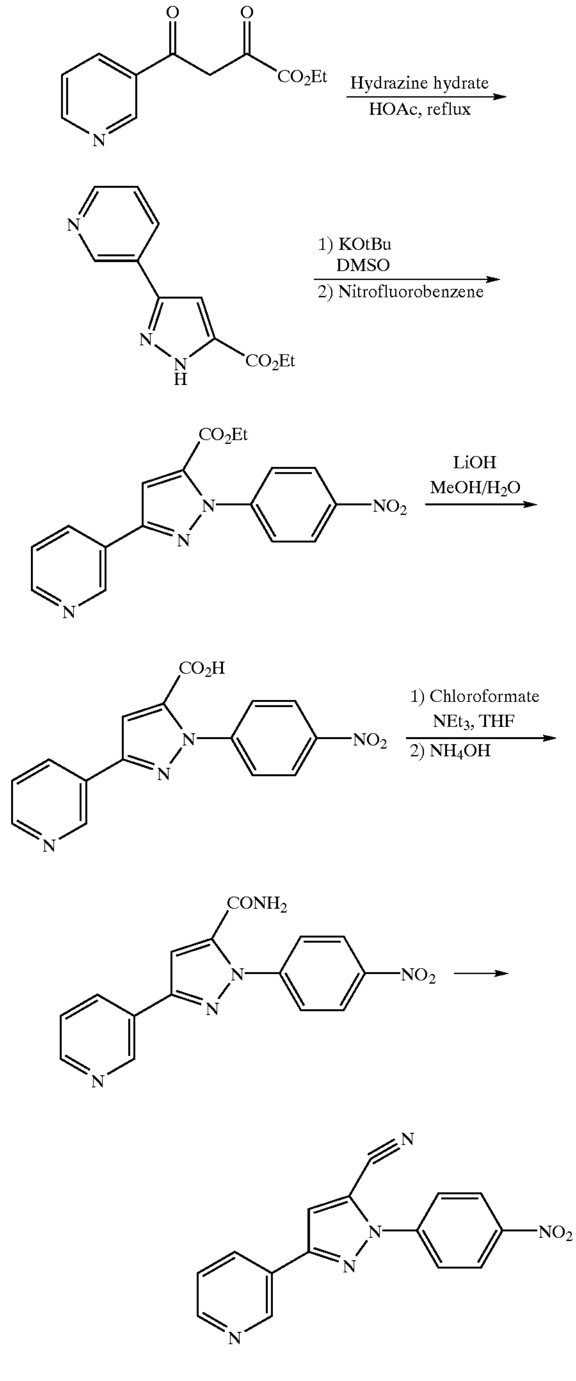

Another procedure where one may regioselectively prepare substituted arylpyrazoles is illustrated by Method Q.

Method Q

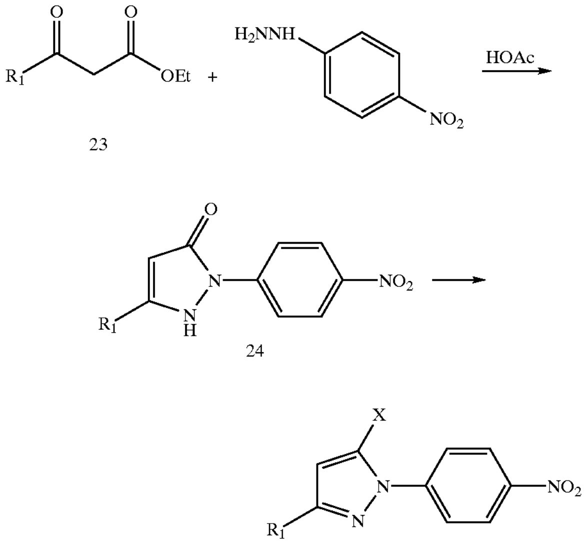

23

24

25

Reaction of ketoester 23 with 4-nitrophenylhydrazine in a suitable solvent, preferably acetic acid at about reflux temperature provides 24. Treatment with a halogenating agent such as phosphorous tribromide or phosphorous oxychloride provides 25 where X=Br or Cl respectively. If desired, 25 (preferably X=Br) may be elaborated further, for example by transition metal catalyzed cross coupling reactions.

For example, as illustrated in Method R, 25a may be cross coupled with a terminal acetylene 26, where W may be, for example, hydrogen, or an alkyl group or any other group not adversely affecting the reaction, using conditions described by T. Sakamoto et al., (Synthesis, 1983, 312) to provide an alkyne at $R_3$ (14a). Alternatively, reaction with vinylstannanes 27, W defined as above, under conditions described by J. W. Stille (Angew. Chem. Int. Ed. Engl., 1986, 25, 508), provides an alkene at $R_3$ (Method S). Reaction with substituted or unsubstituted aryl- or heteroarylboronic acids under conditions described by N. Miyaura et al. (Chem. Rev. 1995, 95, 2457) provides 14c with aryl or heteroaryl groups at $R_3$ (Method T). Alkynes 14a and alkenes 14b may be converted to the corresponding alkyl groups by reduction with a suitable reducing agent such as hydrogen in the presence of a suitable catalyst such as platinum or palladium to provide 1 (see Method L), with an alkyl group at $R_3$. Alternatively, reaction with a reducing agent that leaves alkenes and alkynes intact, such as $SnCl_2$ provides 1 with alkenes or alkynes at $R_3$.

Method R

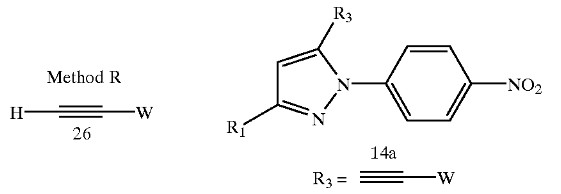

26

14a

-continued

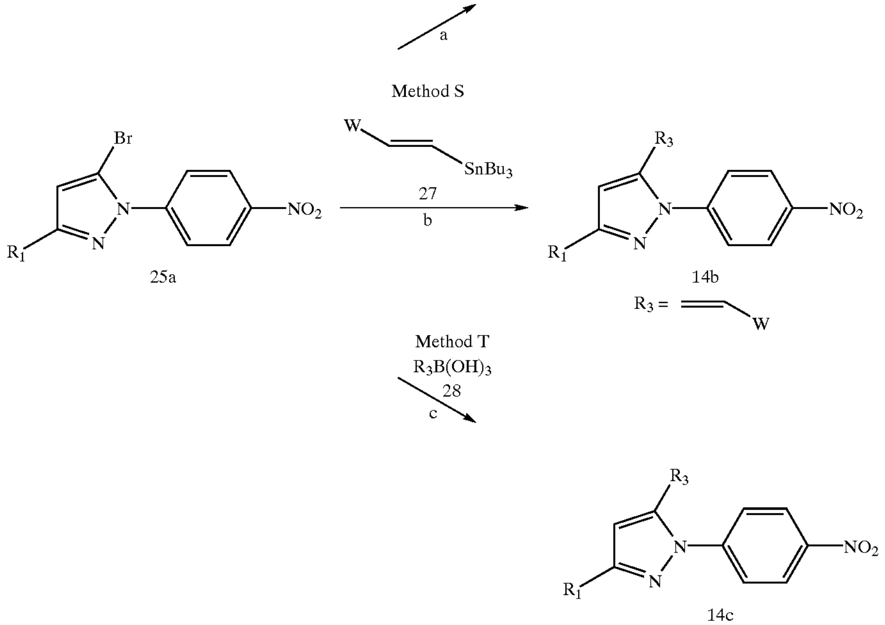

25a

14b

14c $R_3$ = aryl or heteroaryl a. $Pd(PPh_3)_4$, $CuBrSMe_2$, $Et_3N$
b. $Pd(PPh_3)_4$, THF
c. $Pd(PPh_3)_4$, 2M $Na_2CO_3$, THF Method U describes an alternate procedure for preparing compounds of Formula I where L is —NH—. Intermediate 1 may be heated at about 70° C. with an aryl bromide in the presence of a palladium catalyst, preferably $Pd_2(dba)_3$, 2,2'-bis(diphenylphosphino)-1,1'-binapthyl (BINAP), and a base, preferably NaOt-Bu, in a solvent such as toluene, as described by S. Buchwald et al.(J. Amer. Chem. Soc., 1993, 119, 8451). Alternately, one could employ the same conditions with the bromophenylpyrazole 29 and an amine, $R_4NH_2$.

Method U

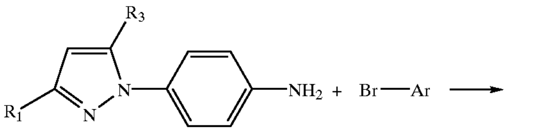

1

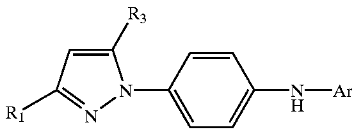

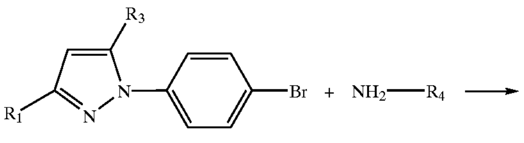

29

-continued

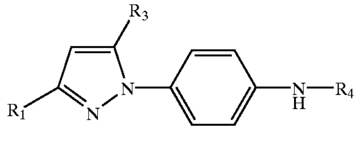

As can be appreciated by chemists possessing ordinary skill in the art, the synthetic schemes described above are for illustrative purposes only and may be modified using conventional synthetic methodology to produce any of the analogs of Formula I. Depending on precisely how the synthetic schemes are modified, the specific reaction conditions might also require modification. Such modifications may involve the use of higher or lower temperature or pressure, conditions other than those reported herein, or the addition of further synthetic steps such as functional group transformations. However, since progress of the reactions is easily monitored by techniques such as high performance liquid chromatography, gas chromatography, mass spectroscopy, thin layer chromatography, nuclear magnetic resonance spectroscopy and the like, such modifications are well within the skill of the art. Likewise, it should be appreciated that initial products from these Methods could be further modified to make additional compounds of this invention. Intermediates used in the Methods described above may be commercially available or could be prepared from commercially available materials by methods described in the chemical literature and known to people skilled in the art.

The 1-phenylpyrazole analogs of Formula I inhibit production of IL-2. Without wishing to be bound by theory, the compounds of this invention inhibit IL-2 production by T cells. This inhibition of IL-2 production is therapeutically useful for selectively suppressing immune function. The result of such selectively suppressed immunity includes reduced cell proliferation of peripheral blood lymphocytes and cellular immune response. Thus, the inhibition of IL-2 production is an attractive means for preventing and treating a variety of immune disorders, including inflammatory diseases, autoimmune diseases, organ and bone marrow transplant rejection and other disorders associated with IL-2 mediated immune response. In particular, the compounds of Formula I may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection) and lupus erythematosus. Other disorders associated with IL-2 mediated immune response will be evident to those of ordinary skill in the art and can also be treated with the compounds and compositions of this invention.

The compounds of this invention may be administered in any conventional dosage form in any conventional manner. Such methods of treatment, including their dosage levels and other requirements, may be selected by those of ordinary skill in the art from available methods and techniques. For example, a compound of this invention may be combined with a pharmaceutically acceptable carrier or adjuvant for administration to a patient in need of such treatment in a pharmaceutically acceptable manner and in an amount effective to treat (including lessening the severity of symptoms) the immune disorder.

The compounds of this invention may be administered alone or in combination with conventional therapeutics, such as conventional immunosuppressants. Advantageously, such combination therapies utilize lower dosages of the conventional therapeutics, thus avoiding possible toxicity and adverse side effects incurred when those agents are used as monotherapies. The compounds of this invention may be physically combined with the conventional therapeutics into a single pharmaceutical composition. Advantageously, the compounds may then be administered together in a single dosage form. Alternatively, the compounds may be administered separately (either serially or in parallel). Separate dosing allows for greater flexibility in the dosing regime.

According to this invention, the compounds of Formula I and the pharmaceutical compositions containing those compounds may be administered to a patient in any conventional manner and in any pharmaceutically acceptable dosage from, including, but not limited to, intravenously, intramuscularly, subcutaneously, intrasynovially, by infusion, sublingually, transdermally, orally, topically or by inhalation. The preferred modes of administration are oral and intravenous.

Dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger (1990)). Dosage levels and requirements are well-recognized in the art and may be selected by those of ordinary skill in the art from available methods and techniques suitable for a particular patient. Typically, dosage levels range from about 10–1000 mg/dose for a 70 kg patient. Although one dose per day may be sufficient, up to 5 doses per day may be given. For oral doses, up to 5000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto and the judgment of the treating physician.

SYNTHETIC EXAMPLES

In order that this invention be more fully understood, the following examples are set forth. These examples are for the purpose of illustrating preferred embodiments of this invention, and are not to be construed as limiting the scope of the invention in any way.

Example 1

Synthesis of N-{4-[3,5-bis(Trifluoromethyl)pyrazol-1-yl] phenyl}cyclohexanecarboxamide (Method A).

A mixture of cyclohexanecarboxylic acid (0.10 g, 0.8 mmol) and EDC (0.077 g, 0.4 mmol) in $CH_2Cl_2$ (1.5 mL) was stirred for 15 minutes. 1(4'-Aminophenyl)-3,5-bis (trifluoromethyl)pyrazole (0.059 g, 0.2 mmol) was added followed by dimethylaminopyridine (0.01 g, 0.1 mmol). After 3 hours the mixture was diluted with $CH_2Cl_2$ (50 mL), washed with 10% $NaHCO_3$ (2×50 mL), brine (3×25mL), and dried over anhydrous $Na_2SO_4$. Evaporation of the solvent gave the above-named compound as a solid that crystallized from benzene (0.075 g, 92%): mp 178–180° C.; $^1H$ NMR ($CDCl_3$) δ 1.35 (3H, m), 1.66 (2H, m), 1.75 (1H, m), 1.85 (2H, m), 2.0 (2H, m), 2.3 (1H, m), 7.08 (1H, s), 7.45 (1H, d, J=8.5 Hz), 7.75 (2H, d, J=8.5 Hz).

Example 2

Synthesis of N-{4-[3,5-bis(Trifluoromethyl)pyrazol-1-yl] phenyl}-2-methylbenzamide (Method B).

A mixture of 1-(4'-aminophenyl)-3,5-bis(trifluoromethyl) pyrazole (0.10 g, 0.34 mmol), o-toluoyl chloride (0.062 mL, 0.43 mmol), and triethylamine (0.06 mL, 0.43 mmol) in methylene chloride (7 mL) was stirred under argon for three days. The reaction mixture was diluted with methylene chloride, washed with 1N hydrochloric acid (2×50 mL), brine (2×40 mL), dried (magnesium sulfate) and concentrated to give an off-white solid. Recrystallization from methylene chloride/hexanes gave the above-named compound (0.065 g). m.p. 175° C. NMR ($CDCl_3$, 400 MHz): δ 7.83 (d, 2H), 7.64 (br s, 1H), 7.53 (m, 3H), 7.43 (m, 1H), 7.31 (m, 2H), 7.10 (s, 1H), 2.56 (s, 3H).

Example 3

Synthesis of N-[4-(3,5-Di-i-propylpyrazol-1-yl)phenyl] pyridine-3-carboxamide (Method C).

A solution of p-(3'-pyridinylcarboxamido) phenylhydrazine hydrochloride (1.5 g, 5 mmol) and 2,6-dimethyl-3,5-heptanedione (0.466 g, 3 mmol) in glacial acetic acid (16 mL) was refluxed for 6 hours. After cooling, the reaction mixture was diluted with water (100 mL) and extracted with EtOAc (2×30 mL), washed with aqueous bicarbonate, and water , and dried ($MgSO_4$). The residue obtained was purified by chromatography over silica gel ($MeOH/CH_2Cl_2$) to give the above-named compound as a white solid (0.240 g, 23%) m.p. 190–2° C. NMR 9.3 (br, 1H); 8.9 (s, 1H); 8.7 (br, 1H); 8.4 (m, 1H); 7.7 (d, 2H); 7.4 (br, 1H); 7.3 (d, 2H); 6.0 (s, 1H); 2.9 (m, 2H); 1.2 (d, 6H); 1.1 (d, 6H).

Example 4

Synthesis of 1-{4-[N-(4-Cyanopyridin-2-yl)amino]phenyl}-3,5-bis(trifluoromethyl)pyrazole (Method D)

A mixture of 1-(4'-aminophenyl)-3,5-bis(trifluoromethyl) pyrazole (0.36 g) and 2-chloro-4-cyanopyridine (0.14 g) in dioxane (1 mL) was heated at 125° C. in a sealed tube for 5 days. The mixture was diluted with ethyl acetate and washed with water. The organic phase was dried, filtered and evaporated. Chromatography of the residue over silica gel (methylene chloride to 2% ethanol/methylene chloride gradient gave the above-named compound (0.22 g) mp 152–153° C. NMR ($CDCl_3$) 8.45 (1H, m), 7.86 (3H, m), 7.48 (2H, d), 7.20 (1H, br s), 7.07 (1H, s), 6.91 (1H, m).

Example 5

Synthesis of Benzo[d]isoxazol-3-yl-{4-[3,5-bis (trifluoromethyl)pyrazol-1-yl]phenyl}amine (Method D)

To a stirred solution of 1-(4'-aminophenyl)-3,5-bis (trifluoromethyl)pyrazole (0.20 g, 0.68 mmol) and 3-chlorobenzisoxazole (0.10 g, 0.65 mmol) in tetrahydrofuran (2.5 mL) under argon was added sodium bis-trimethylsilyl amide (1.0 M in tetrahydrofuran, 0.68 mL, 0.68 mmol). After seven days, the mixture was diluted with water, and extracted with ethyl acetate. The organic layer was washed with brine, dried (magnesium sulfate) and concentrated. The residue was purified by flash chromatography (elution with ethyl acetate/hexanes) to give the above-named compound (0.050 g). m.p. 209–210° C. NMR ($CDCl_3$, 400 MHz): δ 7.77 (d, 1H), 7.64 (m, 3H), 7.53 (d, 2H), 7.37 (m, 1H), 7.09 (s, 1H), 6.68 (s, 1H).

Example 6

Synthesis of N-{4-[(3,5-bis(Trifluoromethyl)pyrazol-1-yl] phenyl}-N'-cyclohexylurea (Method E)

To morpholinomethyl polystyrene (Novabiochem, substitution=3.55 mmol/g, 1.02 g, 3.62 mmol) in methylene chloride (18.5 mL) under argon was added 1-(4'-aminophenyl)-3,5-bis(trifluoromethyl)pyrazole (0.555 g, 1.88 mmol). The mixture was cooled to 0° C. and phosgene (1.93M in toluene, Fluka, 1.95 mL, 3.76 mmol) was added. After thirty minutes the reaction mixture was filtered, washed with methylene chloride (2×30 mL) and concentrated to give 1-(4'-isocyanatophenyl)-3,5-bis (trifluoromethyl)pyrazole.

The solution of 1-(4'-isocyanatophenyl)-3,5-bis (trifluoromethyl)pyrazole (0.10 g. 0.31 mmol) in methylene chloride (2 mL) was added to cyclohexylamine (0.036 mL, 0.32 mmol) in a stoppered vial. The mixture was stirred at room temperature for two and a half days. The solid product was collected by filtration and washed with methylene chloride to give the title compound (0.061 g) m.p. 185–188° C. NMR (DMSO, 270 MHz): δ 8.84 (s, 1H), 7.79 (s, 1H), 7.58 (d, 2H), 7.44 (d, 2H), 6.34 (d, 1H), 3.49 (m, 1H), 1.71 (m, 4H), 1.24 (m, 6H).

Example 7

Synthesis of N-{4-[(3,5-bis(Trifluoromethyl)pyrazol-1-yl] phenyl}-N'-[(R)-tetrahydro-furan-3-yl]urea (Method E)

Triethylamine (0.05 mL, 0.36 mmol) was added to R-(+)-3-aminotetrahydrofuran toluene-4-sulfonate (Fluka, 0.082 g, 0.32 mmol) and 6–8 beads of 4 Å molecular sieves in an oven-dried sealed tube. 1-(4'-Isocyanatophenyl)-3,5-di (trifluoromethyl)pyrazole (0.10 g, 0.32 mmol) in toluene (3 mL) was added, and the mixture was capped and stirred at room temperature for two and a half days. The solid product was collected by filtration, and washed with toluene. Purification by preparative TLC (elution with 1:1 ethyl acetate/ hexanes) followed by recrystallization from ethyl acetate/ hexanes gave the above-named compound as a white solid (0.045 g). m.p. 198–200° C. NMR ($CDCl_3$, 270MHz): δ 8.74 (s, 1H), 7.79 (s, 1H), 7.58 (d, 2H), 7.46 (d, 2H), 6.60 (d, 1H), 4.23 (m, 1H), 3.76 (m, 3H), 3,57 (m, 1H), 2.15 (m, 1H), 1.75 (m, 1H).

Example 8

Synthesis of Morpholine-4-carboxylic Acid {4-[3.5-bis (trifluoromethyl)pyrazol-1-yl]phenyl}amide (Method F)

To a solution of 1-(4'-aminophenyl)-3,5-bis (trifluoromethyl)pyrazole (0.300 g, 1.02 mmol) in of methylene chloride (5 mL) was added diisopropylethyl amine (0.18 mL, 1.0 mmol) followed by 4-morpholine carbonylchloride (0.11 mL, 1.0 mmol). The mixture was stirred at rt for 6 days, and diluted with ethyl acetate. It was then washed twice with water, dried over sodium sulfate and evaporated. Chromatography of the residue over silica gel (50% EtOAc/ hexanes) gave the above-named compound (0.080 g, 19.6%) as a white solid: mp 185–186° C. NMR ($CDCl_3$) δ 7.56 (2H, d), 7.44 (2H, d), 7.07 (1H, s), 6.51 (1H, s), 3.79 (4H, m), 3.54 (4H, m).

Example 9

Synthesis of {4-[3,5-bis(Trifluoromethyl)pyrazol-1-yl] phenyl}-3,5-dimethylisoxazol-4-ylmethyl)amine (Method G)

A solution of N-[4-(3,5-bis(trifluoromethyl)pyrazol-1-yl) phenyl]-3,5-dimethylisoxazole-4-carboxamide (0.418 g, 1 mmol) in dry THF (15 mL) was refluxed at 80° C. with lithium aluminum hydride (1.5 mL of 1 M solution in THF). After 45 minutes the reaction mixture was cooled to room temperature, water (0.3 mL) was added, the mixture was stirred for 5 minutes, the precipitate was removed, and the solvent was evaporated. The residue was taken up in brine (50 mL), and extracted with $CH_2Cl_2$ (3×25 mL). The combined $CH_2Cl_2$ extract was washed with brine (3×25 mL), dried over anhydrous $Na_2SO_4$ and the solvent was evaporated. The residue was purified by flash column chromatography over silica gel (2% acetone in $CH_2Cl_2$) to give the above-named compound (0.200 g. 50%): mp 94–96° C. NMR (DMSO-d6) δ 2.2 (3H, s), 2.38 (3H, s), 4.05 (2H, d, J=5 Hz), 6.43 (1H, t, J=5 Hz), 6.7 (2H, d, J=8 Hz), 7.29 (2H, d, J=8 Hz) 7.7 (1H, s).

Example 10

Synthesis of {4-[3,5-bis(Trifluoromethyl)pyrazol-1-yl] phenyl}ethylamine (Method H)

A mixture of 1-(4'-aminophenyl)-3,5-bis(trifluoromethyl) pyrazole (0.15 g, 0.58 mmol), ethyl iodide (0.10 mL, 1.26 mmol), and Hunig's base (0.20 mL, 1.14 mmol) in N,N-dimethylformamide (10 mL) was heated to 50° C. under argon with stirring. After 24 hours the mixture was diluted with water, and extracted with ethyl acetate. The organic phase was washed with water (4×25 mL), brine, dried (magnesium sulfate) and concentrated. The residue was purified by flash chromatography (ethyl acetate/hexanes) followed by recrystallization from ethanol/water to give the above-named compound (0.045 g) as yellow crystals. mp 54° C. NMR ($CDCl_3$, 400 MHz): δ 7.26 (d, 2H), 7.02 (s, 1H), 6.64 (d, 2H), 3.93 (br s, 1H), 3.22 (q, 2H), 1.31 (t, 3H).

Example 11

Synthesis of N-{4-[3,5-bis(Trifluoromethyl)pyrazol-1-yl] phenyl}pyridin-4-ylmethylamine (Method I)

A mixture of 1-(4'-aminophenyl)-3,5-bis(trifluoromethyl) pyrazole (0.059 g, 0.2 mmol) and pyridine-4-carboxaldehyde (20 μL, 0.2 mmol) in methanol (0.8 mL) and acetic acid (0.2 mL) was stirred at room temperature for 15 minutes Sodium cyanoborohydride (0.032 g, 0.5 mmol) was added, and the reaction mixture stirred overnight. The reaction mixture was diluted with $CH_2Cl_2$ (50 mL), washed with brine (2×20 mL), dried over anhydrous $Na_2SO_4$ and evaporated. The residue was purified by flash column chromatography over silica gel (2% acetone in $CH_2Cl_2$) to give the above-named compound (0.060 g, 78%): mp 92–94° C. NMR (DMSO-d6) δ 4.40 (2H, d), 6.65 (2H, d), 6.97 (1H, t), 7.23 (2H, d), 7.35 (2H, d), 6.65 (2H, d), 7.7 (1H, s), 8.51 (2H, d).

Example 12

Synthesis of {4-[3,5-bis(Trifluoromethyl)pyrazol-1-yl]phenyl}-(1-phenylethyl)amine (Method J)

A mixture of 1-(4'-aminophenyl)-3,5-bis(trifluoromethyl)pyrazole (1.5 g), benzaldehyde (0.53 g) and tosic acid (0.03 g) in toluene (20 mL) was heated under a Dean Stark apparatus at 140° C. for 3 hours. The mixture was filtered and evaporated to dryness to give N-(benzylidene)-1-(4'-aminophenyl)-3,5-bis(trifluoromethyl)pyrazole as a solid (1.4 g) which was used without further purification.

To the stirred imine (0.19 g) in THF under argon at rt was added a solution of methyl lithium (1.6 M in ether, 0.8 mL). After 5 minutes, water (0.2 mL) was added. The mixture was extracted with hexane, and the organic phase was dried, filtered and evaporated. Chromatography of the residue over silica gel (methylene chloride/hexane) gave the above-named compound as an oil that solidified on trituration with cold hexane ((0.115 g): mp 58–61° C. NMR ($CDCl_3$) 7.35–7.21 (m, 5H), 7.15 (2H, d), 6.98 (1H, s), 6.53 (2H, d), 4.52 (1H, q), 4.38 (1H, br s), 1.55 (3H, s).

Example 13

Synthesis of 1-(4'-Aminophenyl)-3-t-butyl-5-trifluoromethylpyrazole and 1-(4'-aminophenyl)-5-t-butyl-3-trifluoromethylpyrazole (Method K)

A mixture of 1,1,1-trifluoro-5,5-dimethylhexane-2,4-dione (5.9 g, 30 mmol) and 4-nitrophenylhydrazine (5.1 g, 30 mmol) in ethanol (75 mL) was heated at 80° C. for 6 hours. The solvent was evaporated, and the residue was treated with neat trifluoroacetic acid (150 mL) for 2 hours. The residue, after evaporation of trifluoroacetic acid, was taken up in aqueous $NaHCO_3$ (250 mL), and extracted with $CH_2Cl_2$ (3×10 mL). The combined extract was washed with water, dried over anhydrous $Na_2SO_4$ and evaporated to give a 4:1 mixture of 1-(4'-nitrophenyl)-3-t-butyl-5-trifluoromethylpyrazole and 1-(4'-nitrophenyl)-5-t-butyl-3-trifluoromethylpyrazole (10 g).

To a stirred solution of the mixture of nitro compounds (1 g) in methanol (50 mL) and acetic acid (1 mL) was added 10% Pd/C (0.24 g) followed by ammonium formate (0.2 g). The mixture was stirred at room temperature for 30 minutes. The catalyst was removed by filtration, and the solvent was evaporated. The residue was taken up in 10% $NaHCO_3$ and the solid precipite was collected;,by filtration, washed with water, and dried under vacuum to give a mixture of 1-(4'-aminophenyl)-3-t-butyl-5-trifluoromethylpyrazole and 1-(4'-aminophenyl)-5-t-butyl-3-trifluoromethylpyrazole (0.87 g).

Example 14

Synthesis of 1-(4'-Nitrophenyl)-3-phenyl-5-ethyl-1H-pyrazole (Method L)

To a solution of 3-phenyl-5-ethylpyrazole (1.0 g, 5.8 mmol) in DMSO (5 mL) was added potassium t-butoxide (0.72 g, 6.4 mmol) followed by 4-fluoronitrobenzene (0.65 mL, 6.4 mmol). The mixture was heated at 90° C. for 1 hour, cooled to rt, and quenched with water (50 mL). The precipitate was collected by filtration, redissolved in ethyl acetate (50 mL), treated with active carbon (3 g), and filtered through diatomaceous earth. The mixture was concentrated to 5 mL, and hexane (25 mL) was added. The 1-(4'-nitrophenyl)-3-phenyl-5-ethylpyrazole was collected by filtration (1.70 g, 92%): mp 112–113° C. NMR 8.39 (2H, d), 7.79 (2H, d), 7.90 (2H, m), 7.45 (2H, m), 7.38 (1H, m), 6.66 (1H, s), 2.86 (2H, q), 1.38 (3H, t).

Example 15

Synthesis of 1-(4'-Aminophenyl)-5-dimethylamino-3-trifluoromethylpyrazole (Method M)

To a solution of N,N-dimethylpropargyl amine (20 mmol) and perfluoroethyl iodide (20 mmol) in $MeCN/H_2O$ (35 mL, 4:3), cooled to 0° C., was added slowly a solution of $Na_2S_2O_4$ (20 mmol) and $NaHCO_3$ (20 mmol) in $H_2O$ (10 mL). After 20 minutes, volatile material was removed, and the residue was extracted with $Et_2O$. The organic phase was washed with brine, dried over $MgSO_4$, and evaporated to give the crude iodoalkene as a yellow oil (2.85 g, 43%). A mixture of the iodoalkene (8.5 mmol) and $NH_2NH_2{*}H_2O$ (42.5 mmol) in EtOH (13 mL,) was heated under reflux for 5 hours. The solvent was removed, and the residue was partitioned between $NaHCO_3$ and $CH_2Cl_2$. The organic phase was washed with brine, dried over $MgSO_4$, and evaporated to give 5-dimethylamino-3-trifluoromethylpyrazole (0.65 g, 40%).

5-Dimethylamino-3-trifluoromethylpyrazole (2.9 mmol) was reacted with 4-nitrofluorobenzene (2.9 mmol), as described in Method L, to give 1-(4'-nitrophenyl)-5-dimethylamino-3-trifluoromethylpyrazole which was purified by chromatography over silica gel (hexanes/EtOAc, 8:2) (0.423 g, 46%). The nitrophenylpyrazole (1.35 mmol) was reduced by phase transfer hydrogenation, described generally in Method L, to give 1(4'-aminophenyl)-5-dimethylamino-3-trifluoromethylpyrazole as an off-white solid (0.321 g, 84%).

Example 16

Synthesis of 1-(4'-Aminophenyl)-3-t- butyl-5-dimethylaminopyrazole (Method N)

A mixture of t-butylacetoacetonitrile (10 mmol) and p-nitrophenylhydrazine (10 mmol) in EtOH (20 mL) was stirred at reflux overnight. The solvent was removed and the residue was partitioned between $CH_2Cl_2$ and brine. The organic phase was dried over $MgSO_4$, and evaporated. Chromatography over silica gel (hexanes/$CH_2Cl_2$/MeOH, 20:79:1) gave 1-(4'-nitrophenyl)-3-t-butyl-5-aminopyrazole (0.950 g, 36%).

A mixture of 1-(4'-nitrophenyl)-3-t-butyl-5-aminopyrazole (I mmol) and formaldehyde (10 mmol, 37% w/w in $H_2O$) in MeOH (7.5 mL) was stirred at rt for 30 minutes. Acetic acid (2.5 mL) and $NaCNBH_3$ (2 mmol) were added, and after 1 hour additional $NaCNBH_3$ (2 mmol) was added. After 1 hour, 1N $H_2SO_4$ was added, the solvent was removed and the residue was neutralized with $NaHCO_3$. The solid product was collected by filtration, washed with water and dried to give 1-(4'-nitrophenyl)-3-t-butyl-5-dimethylaminopyrazole (0.265 g, 92%). Transfer hydrogenation of the nitro compound (0.89 mmol) as described in general in Method L gave 1-(4'-aminophenyl)-3-t-butyl-5-dimethylaminopyrazole (0.228 g, 100%).

Example 17

Synthesis of 1-(4'-Aminophenyl)-5-pyridin-2-yl-3-cyanopyrazole (Method O)

To a suspension of the hydrazone (2.43 g) prepared from pyridine-2-carboxaldehyde and 4-nitrophenylhydrazine in acetonitrile (50 mL) and methylene chloride (30 mL) cooled to 0° C. was added dropwise a solution of iodobenzenediacetate (3.35 g) in methylene chloride (30 mL). The mixture was allowed to warm to rt and stirred overnight. Hexane (100 mL) was added and the solid product 1-(4'-nitrophenyl)-5-(2'-pyridinyl)-3-cyanopyrazoline (2.74 g) was collected by filtration.

To a suspension of the pyrazoline (1.52 g) in methylene chloride (60 mL) cooled on ice was added lead tetraacetate (85%, 2.6 g). The mixture was allowed to warm to rt and stirred for 3 days. The mixture was filtered through diatomaceous earth, and evaporated. Chromatography of the residue over silica gel (methylene chloride/ethanol 99:1–93:7) gave product 1-(4'-nitrophenyl)-5-(2'-pyridinyl)-3-cyanopyrazole (1.01 g).

A mixture of 1-(4'-nitrophenyl)-5-(2'-pyridinyl)-3-cyanopyrazole (0.50 g), 10% Pd/C (0.20 g) and ammonium formate (3.0 g) in ethanol (20 mL) was stirred under argon for 4 hours. The mixture was filtered through diatomaceous earth and the solvent was evaporated. The residue was taken up in chloroform/water, and the organic phase was separated, dried and evaporated to give the crude 1-(4'-aminophenyl)-5-(2'-pyridinyl)-3-cyanopyrazole which was used without further purification.

Example 18

5-Cyano-3-(3-Pyridyl)-1-(4'-aminophenyl)pyrazole (Method P)

A solution of 3-acetylpyridine (11 mL, 100 mmol) and diethyl oxalate (16.5 mL, 120 mmol) in anhydrous THF (200 mL), under an argon atmosphere, was cooled to −78° C. LiHMDS (110 mmol, 1 M in THF) was added and the reaction allowed to slowly warm to room temperature. After 3.5 hrs, volatiles were removed under reduced pressure and the residue was dried under high vacuum overnight. Crude solids were taken up in HOAc (200 mL), treated with hydrazine monohydrate (3.9 mL, 110 mmol) and heated overnight at 90° C. The reaction was allowed to cool to room temperature, volatiles were removed under reduced pressure and residue taken up in aqueous $NaHCO_3$. Solids were filtered, washed with water and dried to give a mixture of isomers containing 5-ethoxycarbonyl-3-(3-pyridyl)pyrazole (1 7.4 g, 80%).

KOt-Bu (9.9 g, 88 mmol), under argon atmosphere, was dissolved in DMSO (180 mL) and stirred for 5 minutes. The above pyrazole (17.4 g, 80 mmol) was added and reaction stirred for 10 min. 4-Nitro-1-fluorobenzene (9.4 mL, 88 mmol) was added and the reaction mixture was stirred and heated overnight at 80° C. After cooling to room temperature, DMSO was removed under reduced pressure and the residue was taken up in ice. Precipitated solids were filtered, washed with water and dried. Crude pyrazole was taken up in MeOH (320 mL) and water (80 mL) and treated with $LiOH.H_2O$ (5 g, 120 mmol). Reaction was complete after 1.5 hrs. Volatiles were removed and the aqueous layer neutralized to pH 5 with 1N $H_2SO_4$. Precipitated solids were filtered, washed with water and dried overnight in vacuum oven to yield 12.7 g (41%) of a mixture containing 5-carboxy-3-(3-pyridyl)-1-(4'-nitrophenyl)pyrazole.

5-Carboxy-3-(3-pyridyl)-1-(4'-nitrophenyl)pyrazole (12.7 g, 41 mmol) was suspended in THF (400 mL) and treated with triethylamine (6.9 mL, 49 mmol). The reaction mixture was cooled to −10° C., treated with isobutylchloroformate (6.4 mL, 49 mmol) and stirred for 45 minutes. Concentrated ammonium hydroxide (3.6 mL, 53 mmol) was added and the reaction mixture was allowed to slowly warm to room temperature and stirred overnight. Volatiles were removed under reduced pressure and the residue was taken up in water. Solids were filtered, washed with water, and dried in vacuum oven to give a mixture of isomers containing 5-carboxamido-3-(3-pyridyl)-1-(4'-nitrophenyl)pyrazole (9.6 g, 76%).

5-Carboxamido-3-(3-pyridyl)-1-(4'-nitrophenyl)pyrazole (9.6 g, 31 mmol) was suspended in DMF (300 mL), cooled to 0° C. and treated with $POCl_3$ (5.8 mL, 62 mmol). The mixture was heated at 80° C. 1 hr, then cooled to room temperature. The volatiles were removed under reduced pressure, the residue was taken up in aqueous $NaHCO_3$ and resulting solids were filtered, washed with water and dried. 5-Cyano-3-(3-pyridyl)-1-(4'-nitrophenyl)pyrazole (2.8 g) was eluted from a silica gel column with $CH_2Cl_2$/MeOH 95:5. Impure fractions were concentrated and washed with diethyl ether to give an additional 1.5 g, for a total of 4.3 g of product (48%).

5-Cyano-3-(3-pyridyl)-1-(4'-nitrophenyl)pyrazole (4.3 g, 15 mmol) was added to stirred slurry of $SnCl_2H_2O$ (20 g, 90 mmol) in HCl/HOAc (35 mL/35 mL). A thick suspension formed and was stirred overnight. The reaction mixture was carefully basified with 50% NaOH to pH 13. The resulting solids were filtered, washed with water and dried to give the title compound (3.9 g, 99%).

Example 18

Synthesis of 1-(4-Nitrophenyl)-3-hydroxymethyl-5-ethylpyrazole (Method L, Scheme I).

To a solution of 3-(tetrahydropyran-2-yloxy)methyl-5-ethylpyrazole (27.0 g, 0.13 mol) in dry THF (250 mL) was added tert-BuOK (14.4g, 0.13 mol) under nitrogen. After 10 min, 4-fluoronitrobenzene (18.1 g, 0.13 mol) was added. The mixture was heated to reflux for 10 hr, the solvent was then removed under vacuum The residue was taken up in ethyl acetate and washed with water, The organic layer was dried over $MgSO_4$ and filtered. The filtrate was treated with active carbon (3.0 g, norit A alkaline) at reflux for 10 min and filtered through a pad of diatomaceous earth. The filtrate was concentrated to give a crude 7:1 mixture of regioisomers, which was dissolved in a 101: mixture of methanol and water (175 mL) and p-toluenesulfonic acid (1.2 g, 6.4 mmol) was added. The solution was stirred at room temperature for 12 hours and concentrated. The residue was taken up in ethyl acetate and washed with water. The organic layer was dried over $MgSO_4$, filtered and concentrated to a crude solid. Recrystallization in a 1:1 mixture of hexane and ethyl acetate gave the title compound (15.6 g, 45%). mp: 151–152° C.

Example 19

Synthesis of 1-(4-Nitrophenyl)-3-isopropenyl-5-ethylpyrazole (Method L, Scheme II)

1(4-Nitrophenyl)-3-(1-hyroxyethyl)-5-ethylpyrazole was prepared by the method described in Example 18, yield: 62%. mp: 127–128° C. To a solution of this alcohol (3.30 g, 12.6 mmol) in $CH_2Cl_2$ (50 mL) was added diatomaceous earth (1.0 g) and pyridinium chlorochromate (3.26 g, 15.2 mmol) and the mixture was stirred at room temperature for 2 hours and filtered. The filtrate was concentrated. The light yellow solid was washed with 101: mixture of hexane and ethyl acetate to give 1-(4-nitrophenyl)-3-acetyl-5-ethylpyrazole (3.00 g, 91%) mp: 93–95° C.

To a solution of methyl triphenylphosphonium bromide (3.47 g, 9.72 mmol) in THF (20 mL) was added 1 M KOt-Bu in THF (9.73 mL, 9.73 mmol) followed by the above ketone (2.10 g, 8.10 mmol). The mixture was stirred at room temperature for 4 hrs, quenched with water and extracted with ethyl acetate. The extract was dried over $Na_2SO_4$ and concentrated. The residue was slurried with hexane and filtered. The filtrate was concentrated to give the title compound as a white solid (1.46 g, 70%). mp: 61–63° C.

Example 20

Synthesis of 1-(4'-Aminophenyl)-5-chloro-3-trifluoromethylpyrazole (Method Q)

A mixture of p-nitrophenylhydrazine (6.372 g) and ethyl trifluoroacetoacetate (6 mL) in acetic acid (40 mL) was heated at reflux for 3 hours. After cooling to room temperature, water (40 mL) was added and the 1(4'-nitrophenyl)-3-trifluoromethyl-5-pyrazolone (9.45 g) was collected by filtration. A mixture of 1-(4'-nitrophenyl)-3-trifluoromethyl-5-pyrazolone (1.43 g) and phosphorus oxychloride (2.8 g) in a sealed tube was heated at 150° C. for 10 hours. The mixture was cooled, and poured onto ethyl acetate/aqueous sodium bicarbonate. The organic phase was separated, washed with dilute HCl, dried, filtered and evaporated. Chromatography of the residue over silica gel (methylene chloride/hexane) gave 1-(4'-nitrophenyl)-5-chloro-3-trifluoromethylpyrazole (0.31 g). 1-(4'-Aminophenyl)-5-chloro-3-trifluoromethylpyrazole was obtained by stannous chloride reduction of the nitro compound as generally described in Method L.

Example 21

Synthesis of 1-(4'-Nitrophenyl)-5-(2-triisopropylsilylethynyl)-3-methylpyrazole (Method R)

To a solution of 1-(4'-nitrophenyl)-5-bromo-3-methylpyrazole (prepared as described for Example 19 except using ethyl acetoacetate instead of ethyl trifluoroacetoacetate and using $PBr_3$ in acetonitrile and refluxing for 72 hr for the halogenation step) (100 mg, 0.35 mmol) in triethylamine (5 mL) was added $Pd(PPh_3)_4$ (20 mg, 0.017 mmol) and $CuBrSMe_2$ (8 mg, 0.036 mmol), followed by triisopropylsilylacetylene (72 mg, 0.39 mmol). The mixture was heated to 70° C. for 1 hour and cooled to room temperature. The solid was filtered off and the filtrate was concentrated. The residue was purified by column chromatography on silica gel (hexane/acetate, 4:1) to give the title compound (127 mg, 95%). mp: 71–73° C.

Example 22

Synthesis of 1(4'-Nitrophenyl)-5-ethenyl-3-methylpyrazole (Method S)

To a solution of 1-(4'-nitrophenyl)-5-bromo-3-methylpyrazole (138 mg, 0.49 mmol) in THF (5 mL) was added $Pd(PPh_3)_4$ (21 mg, 0.018 mmol) followed by vinyl tributyltin (0.16 mL, 0.54 mmol). The mixture was heated at reflux for 6 hr under $N_2$, and was then quenched with saturated KF and extracted with EtOAc. The extract was dried over $MgSO_4$ and concentrated. The residue was purified by column chromatography on silica gel (hexane/acetate, 10:1) to give the title compound (103 mg, 92%).

Example 23

Synthesis of 1-(4'-Nitrophenyl)-5-(4-methoxyphenyl)-3-methylpyrazole (Method T)

To a solution of 1-(4'-nitrophenyl)-5-bromo-3-methylpyrazole (100 mg, 0.35 mmol) in THF (5 mL) was added $Pd(PPh_3)_4$ (20 mg, 0.017 mmol) and 4-methoxyphenylboronic acid (60 mg, 0.39 mmol), followed by 2 M $Na_2CO_3$ (0.35 mL, 0.70 mmol). The mixture was heated to reflux for 4 hr, and was then quenched with water and extracted with EtOAc. The extract was dried over $MgSO_4$ and concentrated. The residue was purified by column chromatography on silica gel (hexane/acetate, 15:1) to give the title compound (102 mg, 94%). mp: 155–158° C.

Example 24

Synthesis of {4-[5-Ethyl-3-(3-pyridyl)pyrazol-1-yl]phenyl}2-(R)-indanylamine Method U A solution of 1-(4-bromophenyl)-5-ethyl-3-(3-pyridyl) pyrazole (obtained by nucleophilic displacement on 1-fluoro-4-bromobenzene by the pyrazole) (100 mg, 0.3 mmol, (R)-1-aminoindane (46 μL, 0.36 mmol), $Pd_2(dba)_3$ (0.50 mg, 0.0006 mmol), (+/−)-BINAP (7.5 mg, 0.012mmol) and sodium t-:butoxide (41 mg, 0.42mmol) in toluene (3 mL) was heated in a sealed tube under argon atmosphere at 70° C. for 20 h. The reaction mixture was diluted with water, extracted with ethyl acetate, the organic extract with washed with brine and dried ($MgSO_4$). The oil obtained was flash chromatographed (40% ethyl acetate/hexane) to obtain the title compound as a yellow oil (0.096 g).

Example 25

Synthesis of 4-(3-cyanopropoxy)-N-[4-(5-cyano-3-pyridin-3-yl-pyrazol-1-yl)phenyl]benzamide

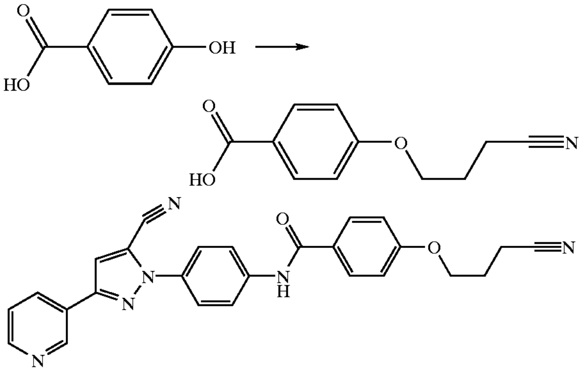

To a stirred solution of 4-hydroxybenzoic acid (40 mmol) in absolute EtOH (350 mL) was added solid NaOEt (84 mmol). After 15 minutes, 4-bromobutyronitrile (40 mmol) was added and the mixture was heated overnight at 90° C. on an oil bath. The mixture was cooled to room temperature, volatiles were removed, the residue was taken up in ice and adjusted to pH 6 with 1N sulfuric acid. Solids were collected by vacuum filtration, washed with water and dried to give 4-(cyanopropyloxy)benzoic acid (4.8 g, 58%).

The 4-(cyanopropyloxy)benzoic acid (0.75 mmol) was coupled with 3-(3-pyridyl)-5-cyano-1-(4'-aminophenyl)-pyrazole (0.5 mmol) under standard EDC mediated conditions (Method A). The crude product was recrystallized from hot benzene/methanol, m.p. 193–194° C. $^1H$ NMR($CDCl_3$): δ 2.04–2.11 (m, 2H), 2.68–2.71 (7, J=7.1 Hz, 2H), 4.14–4.17 (t, J=6 Hz, 2H), 7.11–7.13 (d, J=8.6 Hz, 2H), 7.53–7.56 (m, 1H), 7.79–7.82(d, J=8.7 Hz, 2H), 8.00–8.05 (m, 4H), 8.1 (s, 1H), 8.30–8.32 (d, J=8 Hz, 1H), 8.63–8.64(d, J=4.6 Hz, 1H), 9.15 (s, 1H), 10.4 (s, 1H).

Example 26

Synthesis of 6-[(3-Cyanopropoxy)]-N-[4-(5-cyano-3-pyridin-3-yl-pyrazol-1-yl)phenyl]nicotinamide

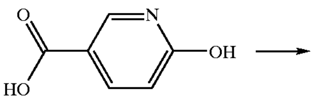

-continued

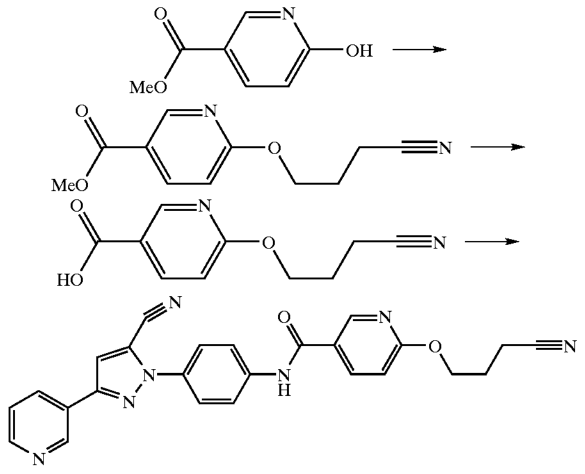

2-Hydroxynicotinic acid (72 mmol) was added to a solution of thionyl chloride (30 mmol) in MeOH (150 mL), cooled to 0° C. The reaction mixture was stirred at room temperature for 2 Edays but most solids did not dissolve. Sulfuric acid (concentrated, 5 mL) was added, and the reaction stirred at reflux overnight. Volatiles were removed and the residue was treated with ice. The solid product (6-hydroxynicotinic acid, methyl ester) was collected by filtration, washed with water and dried. Additional product was isolated upon concentration of aqueous washes. The combined product (8 g, 73%) was taken on without further purification To a stirred solution of this ester (10 mmol) in DMF (30 mL), was added cesium carbonate (10 mmol), After 30 minutes, 4-bromobutyronitrile (10 mmol) was added and the reaction mixture was heated at 65° C. on an oil bath. After 1.5 hours, the mixture was cooled to room temperature, volatiles were removed, the residue was taken up in water and extracted with dichloromethane. The organic phase was dried over magnesium sulfate and concentrated. Chromatography over silica gel (eluent, dichloromethane/ethyl acetate, 9:1) gave 6-(3-cyanopropyloxy)nicotinic acid, methyl ester (416 mg, 19%) as the faster eluting product. N-Alkylated material, 1.5 g (68%), was also obtained.

6-(3-cyanopropyloxy)nicotinic acid, methyl ester (1.8 mmol) was dissolved in methanol/water (16 mL:4 mL) and treated with LiOH monohydrate (2.7 mmol). After stirring overnight, volatiles were removed and reaction neutralized with 1N sulfuric acid. The solid product was collected by filtration, washed with water and dried to give 6-(3-cyanopropyloxy)nicotinic acid (315 mg, 85%).

6-(3-cyanopropyloxy)nicotinic acid (0.6 mmol) was coupled with 3-(3-pyridyl)-5-cyano-1-(4'-aminophenyl)-pyrazole (0.5 mmol) under standard EDC mediated conditions (Method A). Standard work-up gave the title compound (142 mg, 62%), m.p. 190–191° C. $^1$H NMR($CDCl_3$): δ 2.04–2.11 (m, 2H), 2.67–2.70 (7, J=7.1 Hz, 2H), 4.42–4.5 (t, J=6.2 Hz, 2H), 6.98–7.00 (d, J=8.7 Hz, 1H), 7.53–7.56 (m, 1H), 7.82–7.84 (d, J=8.9 Hz, 2H), 8.02–8.04 (d, J=8.9 Hz, 2H), 8.1 (s, 1H), 8.28–8.32 (m, 2H), 8.63–8.64 (m, 1H), 8.82–8.83 (m, 1H), 9.15–9.16 (m, 1H), 10.6 (s, 1H).

Example 27

Synthesis of 4-[(3-[1,3]Dioxolan-2-yl-propoxy)]-N-[4-(5-cyano-3-pyl-pyrazol-1-yl)phenyl]benzamide

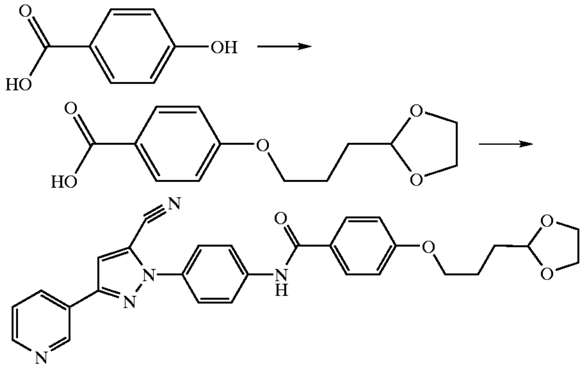

4-Hydroxybenzoic acid (22 mmol) was dissolved in absolute EtOH (120 mL) and treated with solid NaOEt (46 mmol). After stirring for 15 minutes, 2-(3-chloropropyl)-1,3-dioxolane (20 mmol) was added and the reaction mixture was heated overnight at 90° C. in an oil bath. An additional 40 mmol of 2-(3-chloropropyl)-1,3-dioxolane was added and the reaction was refluxed overnight. After letting the reaction mixture cool to room temperature, volatiles were removed, the residue was taken up in ice and the mixture was adjusted to pH 6 with 1N sulfuric acid. Solids were collected by vacuum filtration, washed with water and dried. Crude solids were taken up in warm hexanes, filtered and dried to give the acid (2.35 g, 46%) which was taken on without any further purification.

The acid from above (0.75 mmol) was coupled with 3-(3-pyridyl)-5-cyano-1-(4'-aminophenyl)-pyrazole (0.5 mmol) under standard EDC mediated conditions. Crude product was recrystallized from hot benzene/methanol solution m.p. 192–193° C. $^1$H NMR($CDCl_3$): δ 1.72–1.76 (m, 2H), 1.77–1.86 (m, 2H), 3.77–3.83 (m, 2H), 3.86–3.92 (m, 2H), 4.09–4.12 (t, J=6.2 Hz, 2H), 4.86–4.88 (t, J=4.6 Hz, 1H), 7.08–7.10 (d, J=8.7 Hz, 2H), 7.53–7.56 (m, 1H), 7.79–7.81 (d, J=8.8 Hz, 2H), 7.98–8.00 (d, J=8.7 Hz, 2H), 8.03–8.05 (d, J=8.9 Hz, 2H), 8.1 (s, 1H), 8.30–8.32(d, J=8 Hz, 1H), 8.63–8.64 (d, J=4.4 Hz, 1H), 9.15 (s, 1H), 10.4 (s, 1H).

Example 28

Synthesis of 6-[(3-[1,3]Dioxolan-2-yl-propoxy)]-N-[4-(5-cyano-3-pyridin-3yl-pyrazol-1-yl)phenyl]nicotinamide

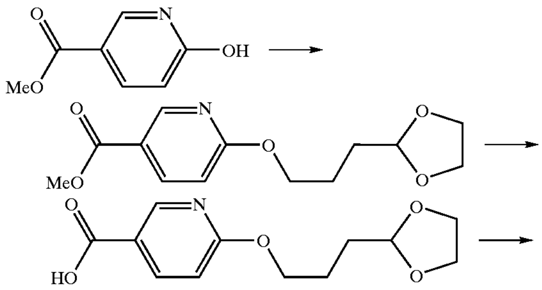

-continued

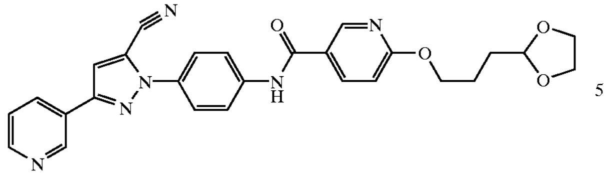

To a stirred solution of 6-hydroxynicotinic acid methyl ester (prepared as describrd in Example 25) (10 mmol) in DMF (30 mL) was added cesium carbonate (10 mmol). After 30 minutes, 2-(3-chloropropyl)-1,3-dioxolane (10 mmol) was added and the reaction mixture was heated at 65° C. on an oil bath. After 2 days, the mixture was cooled to room temperature, volatiles were removed, the residue was taken up in water, and extracted with dichloromethane. The organic phase was dried over magnesium sulfate and concentrated. Chromatography of the residue over silica gel (eluent dichloromethane/ethyl acetate 9:1) gave the desired product as the faster eluting product (311 mg, 12%).

This ester (1.1 mmol) was dissolved in methanol/water (8 mL:2 mL) and treated with LiOH monohydrate (1.7 mmol). After stirring overnight, volatiles were removed, and the mixture was neutralized with 1N sulfuric acid. The solid product was collected by filtration, washed with water and dried to give the free carboxylic acid (250 mg, 87%).

The carboxylic acid (0.46 mmol) was coupled with 3-(3-pyridyl)-5-cyano-1-(4'-aminophenyl)-pyrazole (0.38 mmol) under standard EDC mediated conditions (Method A) to give the title compound (118 mg, 63%) m.p. 197–198° C. $^1$H NMR($CDCl_3$): δ 1.70–1.75 (m, 2H), 1.80–1.86 (m, 2H), 3.76–3.82 (m, 2H), 3.85–3.92 (m, 2H), 4.37–4.40 (t, J=6.4 Hz, 2H), 4.85–4.87 (t, J=4.5 Hz, 1H), 6.96–6.99 (d, J=8.7 Hz, 1H), 7.53–7.56 (m, 1H), 7.81–7.84 (d, J=8.9 Hz, 2H), 8.01–8.04 (d, J=8.9 Hz, 2H), 8.1 (s, 1H), 8.25–8.32 (m, 2H), 8.63–8.64 (m, 1H), 8.81–8.82 (m, 1H), 9.15–9.16 (m, 1H), 10.6 (s, 1H).

Example 29

Synthesis of 6-[(3-Cyanopropoxy)napthalen-1-yl]-[4-(5-ethyl-3-pyridin-3-yl-pyrazol-1-yl)phenyl]amine

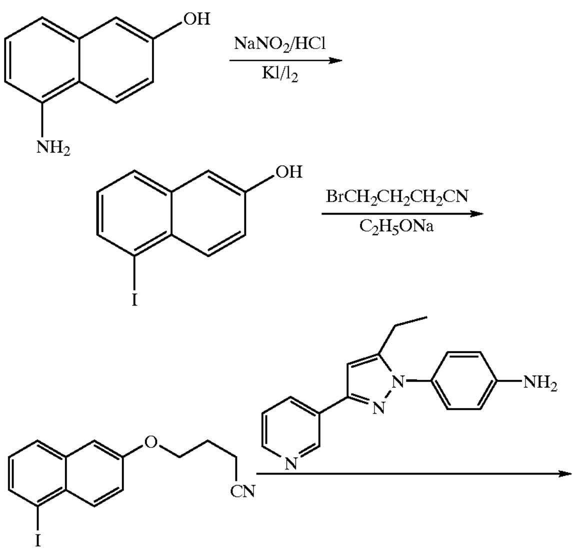

-continued

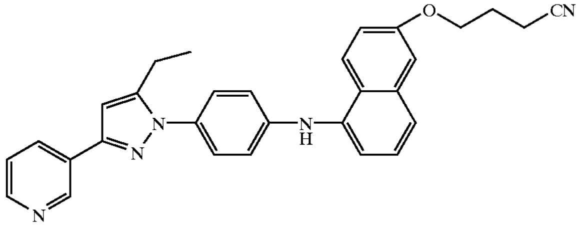

To a stirred mixture of 5-amino-2-naphthol (2.5 g, 15.7 mmol) in 17% HCl (50 mL) was added a solution of $NaNO_2$ (2.1 g, 30.4 mmol) in water (20 mL) at 0° C. After 15 minutes, a solution of urea (2.5 g, 41.6 mmol) in water (20 mL) was added and the mixture was stirred for 15 minutes. The reaction mixture was filtered and the filtrate was added to a solution of KI (18.0 g, 108.4 mmol) and 12 (5.0 g, 197.0 mmol) in water (30 mL) warmed to 70° C. The mixture was cooled overnight in the refrigerator. The black precipitate was filtered and treated with 10% $Na_2SO_4$ (35 mL) for 10 min. Then a solution of 1 N NaOH (60 mL) was added, and the pH was adjusted to 6.5 with 36% HCl. Filtration gave 5-iodo-2-naphthol (0.60 g, 14.2%).

To a stirred mixture of 5-iodo-2-naphthol (300 mg, 1.11 mmol) in EtOH (7 mL) was added $NaOC_2H_5$ (90.7 mg, 1.2 equiv) and, after 10 min, 4-bromobutyronitrile (0.22 mL, 2.0 equiv). The mixture was then heated at reflux for 2 h. It was diluted with water, extracted with dichloromethane, washed with brine and dried ($Na_2SO_4$). Concentration and chromatography on silica gel (hexane/ethyl acetate=4:1) gave 1-(cyanopropyloxy)-5-iodonaphthalene (77 mg, 20.6%).

A mixture of 2-(3-cyanopropoxy)-5-iodonaphthalene (77.0 mg, 0.228 mmol), with 5-ethyl-3-(3-pyridyl)-1-(4'-aminophenyl)pyrazole (72.4 mg, 1.2 equiv.), NaO-t-Bu (40.8 mg, 1.86 equiv.), $Pd_2(dba)_3$ (5.2 mg, 2.5% equiv.) and (–)B1NAP (10.6 mg, 7.5% equiv.) in toluene (1 mL) was heated at 80° C. for 18 h. The mixture was diluted with ethyl acetate, filtered through diatomaceous earth and concentrated. Chromatography on silica gel gave the title compound (98.0 mg, 90.8%). $^1$H-NMR ($CDCl_3$): 1.30 (t, J=7.4 Hz, 3H), 2.20–2.25 (m, 2H), 2.62–2.74 (m, 4H), 4.22 (t, J=5.4 Hz, 2H), 6.31 (bs, 1H), 6.59 (s, 1H), 6.99 (d, J=8.6 Hz, 2H), 7.17 (d, J=9.1 Hz, 1H), 7.20 (s, 1H), 7.29–7.34 (m, 4H), 7.43 (t, J=8.0 Hz, 1H), 7.56 (d, J=8.2 Hz, 1H), 7.98 (d, J=9.2 Hz, 1H), 8.21 (d, J=7.9 Hz, 1H), 8.56 (d, J=4.2 Hz, 1H), 9.11 (s, 1H).

Example 30

Synthesis of [4-(5-Ethyl-3-pyridin-3-yl-pyrazol-1-yl)phenyl]-(2-methylbenzyl)amine

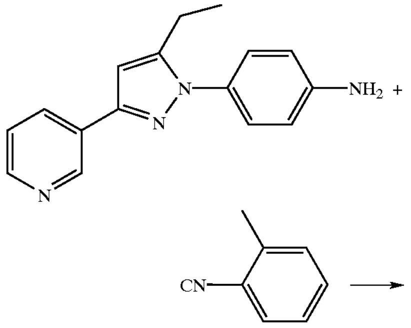

-continued

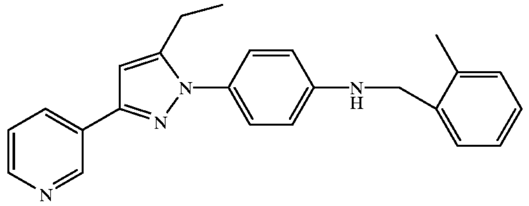

A slurry of Raney Ni (200 mg, 50% in water) was added to a solution 5-ethyl-3-(3-pyridyl)-1-(4'-aminophenyl) pyrazole (500 mg, 1.89 mmol) and o-tolunitrile (0.27 mL, 1.2 equiv.) in glacial acetic acid (20 mL), and the mixture was stirred under hydrogen at 40 psi for 7.5 h. The reaction mixture was filtered through diatomaceous earth, diluted with water, extracted with ethyl acetate, washed with brine, dried ($Na_2SO_4$) and concentrated. Chromatography on silica gel (hexane/ethyl acetate=1:1) gave the title compound (595 mg, 85%). $^1$H-NMR ($CDCl_3$): 1.30 (t, J=7.5 Hz, 3H), 2.42 (s, 3H), 2.69 (q, J=7.5 Hz, 2H), 3.95–4.25 (bs, 1H), 4.36 (s, 2H), 6.58 (s, 1H), 6.72 (d, J=8.7 Hz, 1H), 7.21–7.41 (m, 6H), 8.21 (dd, J=1.6, 6.3 Hz, 1H), 8.56 (d, J=4.1 Hz, 1H), 9.10 (d, J=1.6 Hz, 1H).

Example 31

Synthesis of N-[4-(5-Ethyl-3-pyridin-3-yl-pyrazol-1-yl)phenyl]-1-methylindole-2-carboxamide

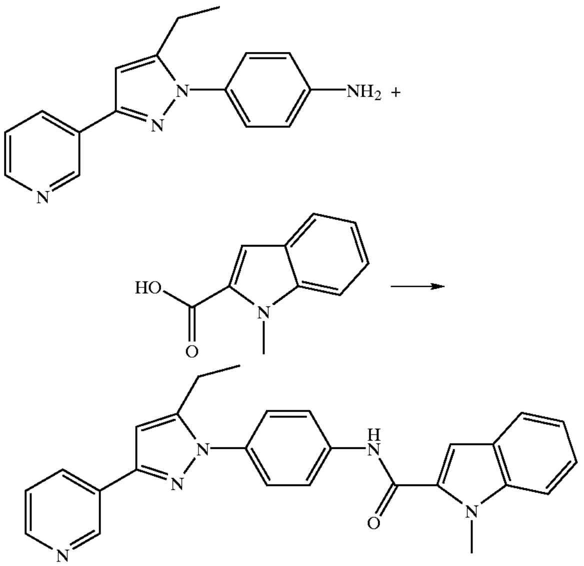

A DMF (2 mL) solution of 3-(3-pyridyl)-5-ethyl-1-(4'-aminophenyl)pyrazole (264 mg, 1 mmol), N-methylindole-2-carboxylic acid (192.5 mg, 1.1 mmol), PyBOP (570 mg, 1.1 mmol) and N,N-diisopropylethylamine (0.21 mL, 1.2 mmol) was stirred at room temperature. for 18 hr. The reaction mixture was poured into crushed ice, and extracted with methylene chloride (3x50 mL). The combined extracts were washed with water, dried over anhydrous sodium sulfate, and the solvent was evaporated. Chromatography of the residue over silica gel (4% methanol/methylene chloride) followed by preparative TLC (silica gel, developer 5% methanol/methylene chloride) gave the title compound as a light, cream colored solid, m.p. 178–179° C. $^1$H NMR (DMSO-d6) δ 1.2 (3H, t, J=7.5), 2.73 (2H, q, J=7.5 Hz), 4.05 (3H, s), 6.93 (1H, s), 7.16 (1H, t, J=7.5), 7.34 (1H, t, J=7.5), 7.37 (1H, s), 7.44–7.48 (1H, dd, J=3.1 & 4.7 Hz), 7.57–7.61 (3H, m), 7.74 (1H, d, J=7.9 Hz), 7.98 (2H, d, J=8.8 Hz), 8.2–8.22 (1H, m), 8.53–8.54 (1H, m), 9.07 (1H, d, J=1.8 Hz), 10.56 (1H, s).

Example 32

Synthesis of [4-(5-ethyl-3-pyridin-3-yl-pyrazol-1-yl) phenyl]-(2-indanylmethyl)amine

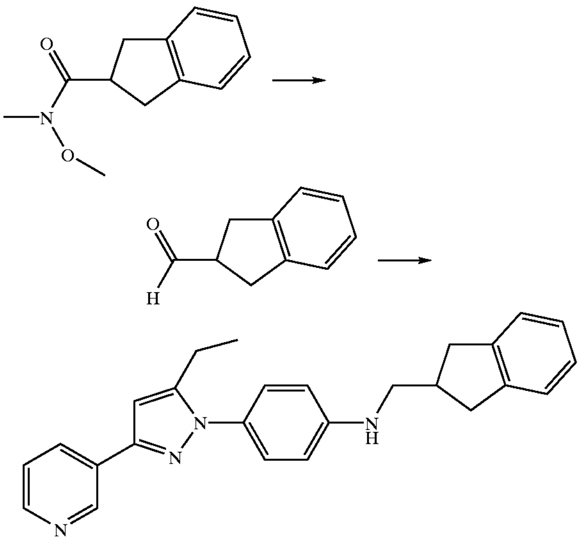

A solution of indane 2-carboxylic acid (324 mg, 2 mmol) and carbonyldiimidazole (299 mg, 2.2 mmol) in DMF (5 mL) was stirred at room temperature for 30 min. N,N-diisopropylethylamine (0.522 mL, 3 mmol) was added followed by N-methoxymethyl amine hydrochloride (195 mg, 2 mmol). The reaction mixture was stirred at room temperature for 18 h, and then treated with 1N sulfuric acid (100 mL). The mixture was extracted with methylene chloride (3x50 mL), and the combined extracts were washed with water, dried over anhydrous sodium sulfate, and evaporated to give N-methoxy-N-methyl-indane-2-carboxamide as a light brownish oil which was used without further purification in the next step.

To a stirred ice-cold solution of the above amide (400 mg, 1.9 mmol) in ether (20 mL), was added lithium aluminium hydride (1 M in THF, 4 mL). After stirring the ice-cold mixture for 1 h, excess reducing agent was quenched by the careful addition of 1N sulfuric acid (10 mL). The reaction mixture was stirred for 5min, the ether layer was decanted and the remaining solid was washed with ether (100 mL). The combined ether extract was washed with water, dried over anhydrous sodium.sulfate, and evaporated to give indane 2-carboxaldehyde as a light brownish oil which was used without further purification in the next step.

A solution of 3-(3-pyridyl)-5-ethyl-1-(4'-aminophenyl) pyrazole (185 mg, 0.7 mmol) and indane 2-carboxaldehyde (0.96 mmol, 140 mg) in methanol (9 mL) and acetic acid (1 mL) was stirred at room temperature for 30 min. Sodium cyanoborohydride (124 mg, 2 mmol) was added and stirring continued at room temperature. After 3 h the solvent was evaporated under vacuum, the residue was taken up in sodium bicarbonate solution (50 mL), and extracted with methylene chloride (3x50 mL). The combined organic extracts were washed with water, dried over anhydrous sodium sulfate, and evaporated. Chromatography of the residue over silica gel (eluant, 35% ethyl acetate in methylene chloride) gave the title compound which was taken up in 50% aqueous acetonitrile containing 1% trifluoroacetic acid and lyophilized to give a light yellow solid. $^1H$ NMR ($DMSO-d_6$) δ 1.2 (3H, t, J=7.5 Hz), 2.63 (2H, q, J=7.5 Hz), 2.7–2.76 (3H, m), 3.05–3.12 (4H, m), 6.71 (2H, d, J=8.7 Hz), 6.98 (1H, s), 7.12–7.14 (2H, m), 7.21–7.24 (4H, m), 7.84–7.88 (1H, m), 8.65 (1H, br, d, J=8.2 Hz), 8.71 (1H, d, J=5.1 ),9.2 (1H, s).

Example 33

Synthesis of [4-(5-Cyano-3-pyridin-3-yl-pyrazol-1-yl) phenyl]-(2-indanylmethyl)amine

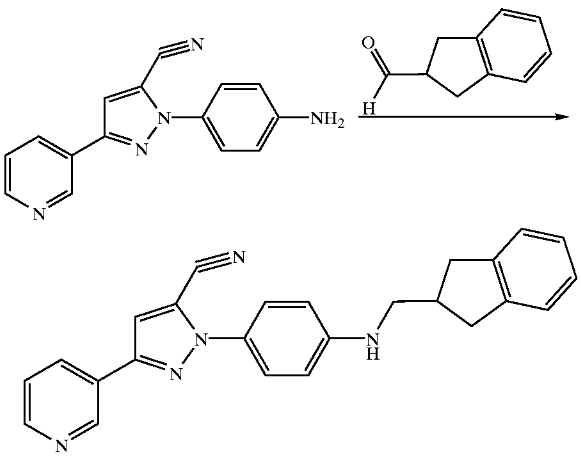

A solution of 5-cyano-3-(3-pyridyl)-1-(4'-aminophenyl) pyrazole (185 mg, 0.7 mmol) and indane 2-carboxaldehyde (0.96 mmol, 140 mg) in methanol (9 mL) and acetic acid (1 mL) was stirred at room temp for 30 min. Sodium cyanoborohydride (124 mg, 2 mmol) was added and stirring continued at room temperature. After 3 h the solvent was evaporated under vacuum, and the residue was taken up in sodium bicarbonate solution (50 mL) and extracted with methylene chloride (3×50 mL). The combined extract was washed with water, dried over anhydrous sodium sulfate and evaporated. Chromatography of the residue over silica gel (eluant, 15% ethyl acetate in methylene chloride) gave the title compound as a cream colored solid, m.p. 156–158° C. $^1H$ NMR (DMSO-d6): δ 2.68–2.82 (3H, m), 3.05–3.15 (4H, m), 6.36–6.42 (1H, br. t), 6.75–6.77 (2H, d, J=8.9 Hz), 7.09–7.15 (2H, m), 7.21–7.24 (4H, m), 7.45–7.47 (2H, d, J=8.8 Hz), 7.51–7.54 (1H, m), 7.98 (1H, s), 8.21–8.28 (1H, br. d.), 8.6–8.62 (1H, br. d.), 9.1 (1H, d, J=1.9 Hz).

Example 34

Synthesis of (2-Chloro-6-fluorobenzyl)-[4-(5-cyano-3-pyridin-3-yl-pyrazol-1-yl)phenyl]amine

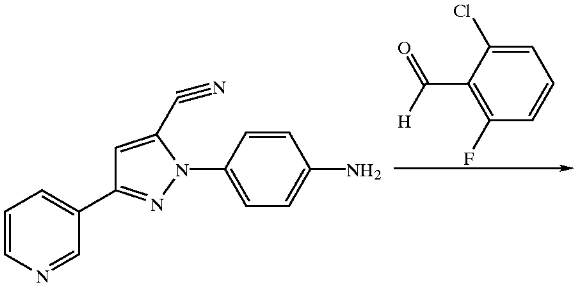

-continued

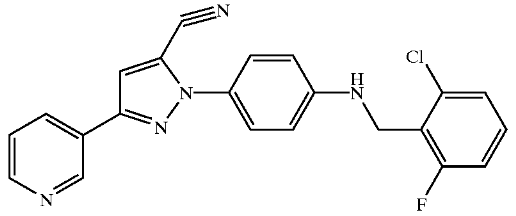

To a stirred solution of 1-(4-aminophenyl)-3-(3-pyridyl)-5-cyanopyrazole (130 mg, 0.5 mmol) in acetic acid (2 mL) and MeOH (6 mL) at room temperature was added 2-chloro-6-fluorobenzaldehyde (79 mg, 0.5 mmol), followed by sodium cyanoborohydride (79 mg, 1.25 mmol). The reaction mixture was stirred at room temperature for 16 h and then concentrated under a stream of nitrogen. The residue was diluted with water, extracted into ethyl acetate, washed with sodium bicarbonate solution and water, and dried ($MgSO_4$). The residue obtained on concentration was flash chromatographed on silica gel (eluent, gradient of 20–30% EtOAc in $CH_2Cl_2$) to provide the title compound (103 mg, 51%). NMR ($CDCl_3$, 400 MHz): 9.1 (s, 1H); 8.7 (br, 1H); 8.3 (d, 1H); 7.6–7.5 (overlapping m, 3H), 7.6–7.5 (overlapping m, 4H), 7.05 (m, 1H); 6.9 (d, 2H), 4.6 (s, 2H).

Example 35

Synthesis of [4-(5-Cyano-3-pyridin-3-yl-pyrazol-1-yl) phenyl]-(2,6-dimethylbenzyl)-amine To a stirred solution of 2,6-dimethylbenzonitrile (1 g, 7.6 mmol) in THF (15 mL) under argon at 0° C. a solution of DIBAL (1 M in THF, 8 mL, 8 mmol) was added dropwise over 5 minutes. After 3 hr at 0° C., the reaction mixture was brought to room temperature and stirred overnight. The reaction was quenched with 5% sulfuric acid at 0° C., extracted with ether, washed with brine and dried ($MgSO_4$). Concentration provided 2,6-dimethylbenzaldehyde (0.9 g) which was used without further purification.

To a stirred solution of 1-(4-aminophenyl)-3-(3-pyridyl)-5-cyanopyrazole (130 mg, 0.5 mmol) and 2,6-dimethylbenzaldehyde (0.9 g) in acetic acid (2 mL) and MeOH (5 mL) at room temperature was added sodium cyanoborohydride (79 mg, 1.25 mmol). The reaction mixture was stirred at room temperature for 18 hr and then concentrated under a stream of nitrogen, diluted with water, extracted into ethyl acetate, washed with sodium bicarbonate solution, water and dried ($MgSO_4$). The residue obtained on concentration was flash chromatographed on silica gel (elution with a gradient of 15–25% EtOAc in $CH_2Cl_2$) providing the title compound (142 mg, 75%). NMR ($CDCl_3$, 400 MHz): 9.1 (s, 1H); 8.7 (br, 1H); 8.3 (d, 1H); 7.6 (d, 2H), 7.5 (m, 1H), 7.35 (s, 1H); 7.2 (m, 1H), 7.1 (overlapping m, 2H), 6.8 (d, 2H), 4.3 (s, 2H), 2.4 (s, 6H).

Example 36

Synthesis of [4-(5-Cyano-3-pyridin-3-yl-pyrazol-1-yl) phenyl]-(2-chloro-6-methylbenzyl)amine To a stirred solution of 2-chloro-6-methylbenzonitrile (1 g, 6.6 mmol) in THF (15 mL) under argon at 0° C. a solution of DIBAL (1 M in THF, 7 mL, 7 mmol) was added dropwise over 5 minutes. After 3 hr at 0° C., the reaction mixture was brought to room temperature and further stirred overnight. The reaction mixture was quenched with 5% sulfuric acid at 0° C., extracted with ether, washed with brine and dried ($MgSO_4$). Concentration provided 2-chloro-6-methylbenzaldehyde (0.92 g) which was used without further purification.

To a stirred solution of 1-(4-aminophenyl)-3-(3-pyridyl)-5-cyanopyrazole (130 mg, 0.5 mmol) and 2-chloro-6-methylbenzaldehyde (0.9 g) in acetic acid (4 mL) and MeOH (7 mL) at room temperature was added sodium cyanoborohydride (79 mg, 1.25 mmol). The reaction mixture was stirred at room temperature for 16 h and then concentrated under a stream of nitrogen, diluted with water, extracted into ethyl acetate, washed with sodium bicarbonate solution, water and dried ($MgSO_4$). The residue obtained on concentration was chromatographed on silica gel (eluant, gradient of 15–25% EtOAc in $CH_2Cl_2$) to provide the title compound (152 mg, 76%). NMR ($CDCl_3$, 400 MHz): 9.2 (s, 1H); 8.7(br, 1H); 8.4(br, 1H); 7.6–7.5 (overlapping m, 3H), 7.4–7.1(overlapping m, 5H), 6.8 (d, 2H), 4.5 (s, 2H), 2.5 (s, 3H).

Example 37

Synthesis of [4-(5-Ethyl-3-pyridin-3-yl-pyrazol-1-yl) phenyl]-(2-chloro-6-fluorobenzyl)amine To a stirred solution of 1(4-aminophenyl)-3-(3-pyridyl)-5-ethylpyrazole (300 mg, 1.14 mmol) and 2-chloro-6-fluorobenzaldehyde (360 mg, 2.27 mmol) in 5% HOAc/MeOH (6 mL) at room temperature under argon was added sodium cyanoborohydride (180 mg, 2.86 mmol). The reaction mixture was stirred at room temperature for 4 h and then concentrated, diluted with water, extracted into ethyl acetate and washed with brine. The residue obtained on concentration was chromatographed on silica gel (eluant, gradient of 25–50% EtOAc in hexane) to provide the title compound as an oil which solidified on trituration with ether/petroleum (152 mg, 32%). m.p. 123–5° C. NMR ($CDCl_3$, 400 MHz): 9.1 (s, 1H); 8.6 (br, 1H); 8.2 (br, 1H); 7.4–7.2 (overlapping m, 5H), 7.05 (m, 1H), 6.8 (d, 2H), 6.6 (s, 1H), 4.6 (s, 2H), 4.4 (br, 1H), 2.7 (q, 2H), 1.2 (t, 3H).

Example 38

Synthesis of [4-(5-Ethyl-3-pyridin-3-yl-pyrazol-1-yl) phenyl]-(2-methylbenzyl)-amine To a stirred solution of 1-(4-aminophenyl)-3-(3-pyridyl)-5-ethylpyrazole (300 mg, 1.14 mmol) and o-tolualdehyde (260 mg, 2.25 mmol) in 5% HOAc/MeOH (6 mL) at room temperature under argon, sodium cyanoborohydride (200 mg, 3.18 mmol) was added. The reaction mixture was stirred at room temperature for 4 h and then concentrated, diluted with water, extracted into ethyl acetate, washed with brine. The residue obtained on concentration was chromatographed on silica gel (eluant, gradient of 25–50% EtOAc in hexane) to provide the title compound as an oil that solidified on trituration with ether/petroleum ether (97 mg, 23%), m.p. 117–9° C. NMR ($CDCl_3$, 400 MHz): 9.1 (s, 1H); 8.5 (br, 1H); 8.1 (br, 1H); 7.4–7.2 (overlapping m, 7H), 6.7 (d,2H), 6.5 (s, 1H), 4.4 (s, 2H), 4.1 (br, 1H), 2.7 (q, 2H), 2.4 (s, 3H), 1.3 (t, 3H).

Example 39

Synthesis of [4-(5-Ethyl-3-pyridin-3-yl-pyrazol-1-yl) phenyl]-[4-(3-cyanopropoxy)benzyl]-amine

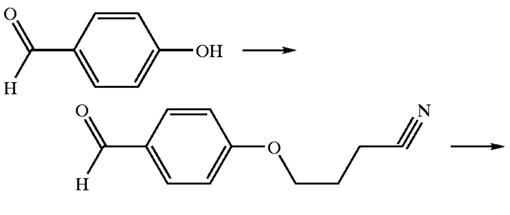

-continued

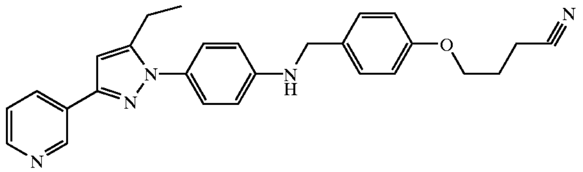

4-Hydroxybenzaldehyde (20 mmol) was dissolved in absolute EtOH (150 mL) and treated with solid NaOEt (24 mmol). After stirring for 15 minutes, 4-bromobutyronitrile (24 mmol) was added and reaction mixture was heated overnight at 90° C. in an oil bath. After letting the reaction cool to room temperature, volatiles were removed, the residue was taken up in ice, adjusted to pH 6 with 1N sulfuric acid, and extracted with methylene chloride. The organic phase was washed with brine, dried over $MgSO_4$ and concentrated. Chromatography over silica gel (eluant, 5% EtOAc in hexanes) gave the 4-(3-cyanopropoxy) benzaldehyde (4.8 g, 58%).

3-(3-Pyridyl)-5-ethyl-1(4'-aminophenyl)-pyrazole (0.5 mmol) was dissolved in MeOH (4 mL) and treated with HOAc (0.5 mL). The reaction was treated with the solution of aldehyde from above (0.75 mmol) in MeOH (1 mL) and stirred at room temperature for 30 minutes. $NaCNBH_3$ (1.25 mmol) was added in one portion. After 2 hrs, volatiles were removed, the residue was taken up in water, neutralized with $NaHCO_3$ (aq) and extracted with dichloromethane. The organic phase was dried over $MgSO_4$ and concentrated. Chromatography over silica gel (eluant, 50% dichloromethane in EtOAc) gave the title compound as an off-white solid (178 mg, 78%), m.p. 131–132° C. $^1H$ NMR ($CDCl_3$): δ 1.15–1.18 (t, J=7.5 Hz, 3H), 1.98–2.04 (m, 2H), 2.56–2.67 (m, 4H), 4.00–4.04 (t, J=6 Hz, 2H), 4.24–4.26 (d, J=5.8 Hz, 2H), 6.72–6.79(m, 3H), 6.53–6.56(t, J=5.8 Hz, 1H), 6.66–6.68 (d, J=8.7 Hz, 2H), 6.80 (s, 1H), 6.92–6.94 (d, J=8.4 Hz, 2H), 7.16–7.18 (d, J=8.6 Hz, 2H), 7.30–7.32 (d, J=9.4 Hz, 2H), 7.40–7.43 (m, 1H), 8.13–8.15(d, J=8 Hz, 1H), 8.48–8.50 (d, J=4.6 Hz, 1H), 9.0 (s, 1H).

Example 40

Synthesis of [4-(5-Cyano-3-pyridin-3-yl-pyrazol-1-yl) phenyl]-[4-(3-cyanopropoxy)benzyl]-amine

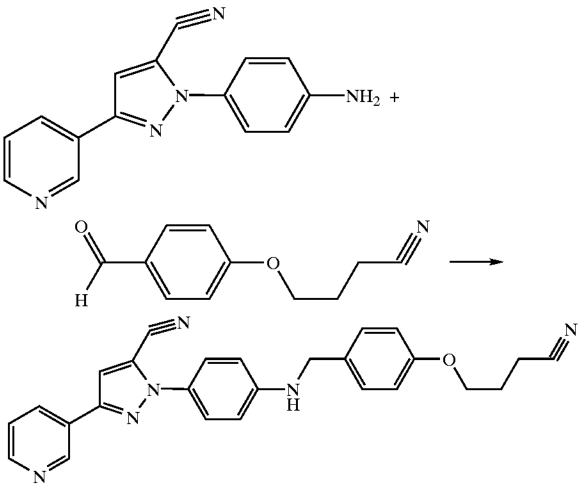

3-(3-Pyridyl)-5-cyano-1-(4'-aminophenyl)pyrazole (0.5 mmol) was dissolved in MeOH (4 mL) and treated with HOAc (4 mL). The reaction was treated with a solution of 4-(3-cyanobutoxy)benzaldehyde (from Example above) (0.75 mmol) in MeOH (1 mL) and stirred at room temperature for 30 minutes. $NaCNBH_3$ (1.25 mmol) was added in one portion. After 2 hr, volatiles were removed, the residue taken up in water, neutralized with $NaHCO_3$ (aq) and extracted with dichloromethane. Organic extracts were combined, dried over $MgSO_4$ and concentrated to leave a clear oil. Pure product was eluted from silica gel column using 50% dichloromethane in EtOAc giving a light yellow solid (140 mg, 64%), m.p. 128–129° C. $^1H$ NMR ($CDCl_3$): δ 1.98–2.04 (m, 2H), 2.63–2.66 (t, J=7.1 Hz, 2H), 4.00–4.04 (t, J=6 Hz, 2H), 4.27–4.29 (d, J=5.8 Hz, 2H), 6.72–6.79 (m, 3H), 6.92–6.94 (d, J=8.5 Hz, 2H), 7.31–7.33 (d, J=8.5 Hz, 2H), 7.42–7.44 (d, J=8.7 Hz, 2H), 7.50–7.53 (m, 1H), 7.96 (s, 1H), 8.24–8.26 (d, J=8 Hz, 1H), 8.60–8.61 (d, J=4.6 Hz, 1H), 9.10 (s, 1H).

Example 41

Synthesis of [4-(5-Ethyl-3-pyridin-3-yl-pyrazol-1-yl)phenyl]-(2-fluoro-6-methylbenzyl)amine A mixture of 2-chloro-6-methylbenzonitrile (5 g, 33.0 mmol) and CsF (14 g, 92.2 mmol) in DMSO (30 ml) was heated at 140° C. for 15 hr and then allowed to cool to room temperature. It was diluted with water, extracted with dichloromethane, washed with brine, dried ($Na_2SO_4$) and concentrated to give 2-fluoro-6-methylbenzonitrile (2.93 g, 66%). A mixture of the above nitrile (250 mg), 1-(4-aminophenyl)-3-(3-pyridyl)-5-ethylpyrazole (200 mg, 0.76 mmol) and Raney Ni (50% in water, 100 mg) in glacial acetic acid (15 ml) was shaken in a Parr apparatus under $H_2$ (40 psi) for 7 hr. The catalyst was removed by filtration and the solvent was evaporated. Chromatography on silica gel (hexane/ethyl acetate=2:1) afforded the title compound (146 mg). $^1H$-NMR ($CDCl_3$): 1.30 (t, J=7.5 Hz, 3H), 2.46 (s, 3H), 2.67 (q, J=7.5 Hz, 2H), 3.92 (bs, 1H), 4.38 (s, 2H), 6.58 (s, 1H), 6.78 (d, J=8.6 Hz, 2H), 6.99 (t, J=6.8Hz, 1H), 7.05 (d, J=7.8 Hz, 1H), 7.19–7.38 (m, 4 H), 8.20 (d, J=7.8 Hz, 1H), 8.56 (d, J=3.7Hz, 1H), 9.10 (s, 1H).

Example 42

Synthesis of N-[4-(5-Ethyl-3-pyridin-3-yl-pyrazol-1-yl)phenyl]nicotinamide

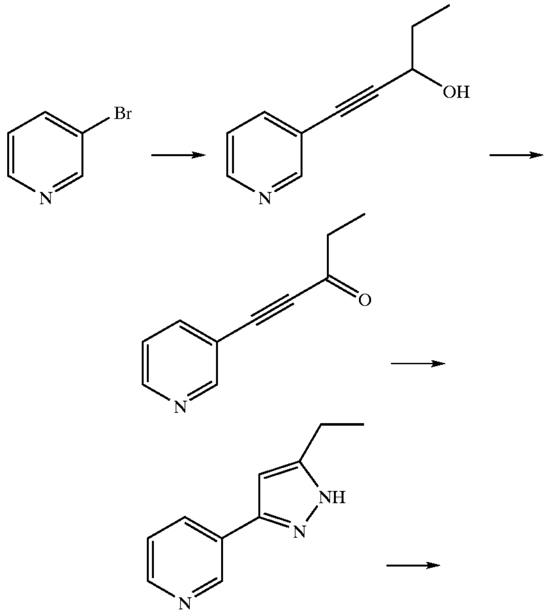

-continued

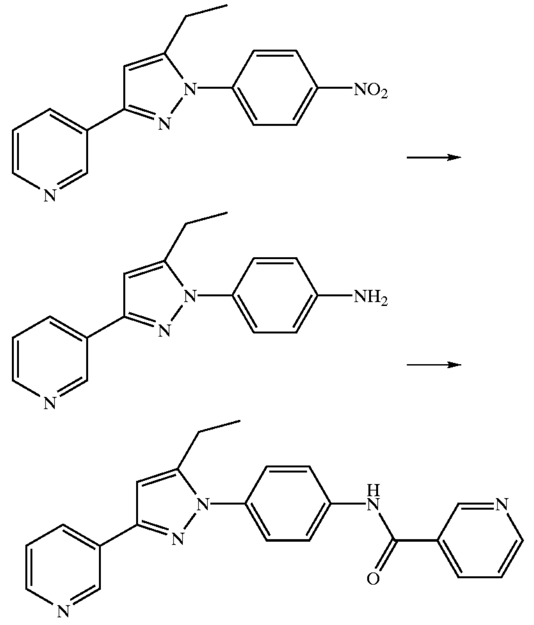

To a solution of 3-bromopyridine (12.0 g, 75.6 mmol) and 1-pentyn-3-ol (7.0 mL, 83.2 mmol) in triethylamine (150 mL) were added $Pd(PPh_3)_4$ (88 mg, 0.076 mmol) and copper(I) bromide dimethylsulfide (31 mg, 0.15 mmol). The mixture was heated at 70° C. for 5 hr, cooled to room temperature and filtered. The filter cake was washed with EtOAc (30 mL). The combined filtrate was concentrated to give 1-(3-pyridinyl)-1-pentyn-3-ol (12.2 g, 99%) as a dark oil.

To a solution of $(COCl)_2$ (7.9 mL, 91.0 mmol) in $CH_2Cl_2$ (300 mL) was added DMSO (11.0 mL, 151 mmol) at −78° C., followed by 1-(3-pyridinyl)-1-pentyn-3-ol (12.2 g, 75.6 mmol) in $CH_2Cl_2$ (100 mL). The mixture was stirred at −78° C. for 1 hr, and then quenched with triethylamine (32 mL, 227 mmol). After being warmed to 0° C., the mixture was diluted with water and the layers were separated. The organic phase was dried over $MgSO_4$ and concentrated to give 1(3-pyridinyl)-1-pentyn-3-one (12.2 g, 99%) as an oil. $^1H$ NMR ($CDCl_3$, 400 MHz) 8.81 (bs, 1H), 8.68 (bs, 1H), 7.87 (m, 1H), 7.32 (m, 1H), 2.73 (q, J=7.4Hz, 2H), 1.24 (t, J=7.4 Hz, 3H).

To a solution of the above propargyl ketone (12.2 g, 75.6 mmol) in EtOH (200 mL) at room temperature hydrazine monohydrate (4.2 mL, 83.2 mmol) was added over 15 min. The mixture was stirred at room temperature for 3 hr and concentrated. The residue was taken up in EtOAc and washed with water. The organic phase was dried over $MgSO_4$ and concentrated to give 3-(3-pyridinyl)-5-ethylpyrazole (13.2 g, 99%) as a solid. $^1H$ NMR ($CDCl_3$, 400 MHz) 9.00 (s, 1H), 8.85 (d, J=4.6Hz, 1H), 8.07 (d, J=7.9 Hz, 1H), 7.32 (m, 1H), 6.43 (s, 1H), 2.75 (q, J=7.6 Hz, 2H), 1.24 (t, J=7.6 Hz, 3H).

To a solution of 3-(3-pyridinyl)-5-ethylpyrazole (13.2 g, 75.6 mmol) in DMSO (70 mL) was added t-BuOK (9.3 g, 83.2 mmol), and then 4-fluoronitrobenzene (8.8 mL, 83.2 mmol). The mixture was heated to 80° C. for 1 hr. After being cooled to room temperature, the mixture was quenched with water (300 mL). The resulting slurry was stirred for 30 min and filtered. The cake was washed with water and dried in oven under house vacuum at 40° C. overnight. The solid was then treated with a 1:2 mixture of ethyl acetate and hexane (150 mL) and the slurry was filtered. The solid was washed with the same solvent system and dried in an oven under house vacuum to give 1-(4-nitrophenyl)-3-(3-pyridinyl)-5-ethylpyrazole (18.5 g, 82%). $^1$H NMR ($CDCl_3$, 400 MHz) 9.09 (s, 1H), 8.60 (d, J=4.0 Hz, 1H), 8.38, 7.76 (ABq, J=9.04 Hz, 4H), 8.17(m, 1H), 7.36 (m, 1H), 6.67 (s, 1H), 2.84 (q, J=7.5Hz, 2H), 1.36 (t, J=7.5 Hz, 3H).

1-(4-Nitrophenyl)-3-(3-pyridinyl)-5-ethylpyrazole (18.0 g, 61.2 mmol) was dissolved in dioxane (200 mL) and MeOH (200 mL). The solution was treated with ammonium formate (38.6 g, 612 mmol) and 5% Pd/C (1.8 g) at room temperature for 6 hr. It was then filtered through a pad of diatomaceous earth and the cake was washed with $CH_3CN$. The filtrate was concentrated and the residue was treated with water (200 mL). The resulting slurry was stirred at room temperature for 3 hr, and collected by filtration. The solid was washed with water and dried in an oven under house vacuum to give 1-(4-aminophenyl)-3-(3-pyridinyl)-5-ethylpyrazole (15.5 g, 95%). %). $^1$H NMR ($CDCl_3$, 400 MHz) 9.05 (s, 1H), 8.53 (d, J=4.7 Hz, 1H), 8.16 (d, J=7.2 Hz, 1H), 7.30 (m, 1H), 7.23, 6.75 (ABq, J=8.1 Hz, 4H) 6.54 (s, 1H), 3.83 (bs, 2H), 2.63 (q, J=7.6 Hz, 2H), 1.25 (t, J=7.6 Hz, 3H).

The pyrazole from above (16.2 g, 61.3 mmol) was dissolved in 1:1 mixture of THF and $CH_2Cl_2$ (300 mL), and nicotinic acid (8.3 g, 67.4 mmol) and EDC (14.1 g, 73.5 mmol) were added. The resulting mixture was stirred at room temperature for 5 hr. The resulting solution was concentrated and the residue was treated with water (300 mL). The slurry was stirred for 2 hr and then filtered. The cake was washed with water, dried in an oven at 40° C. under house vacuum overnight. The dried solid (22.6 g) was recrystallized from an 8:1 mixture of EtOAc and MeOH to give the title compound (20.5 g, 91%), m.p. 188–190° C. 1H NMR ($CDCl_3$, 400 MHz): 9.13 (s, 1H), 9.06 (s, 1H), 8.79 (d, J=4.8 Hz, 1H), 8.53 (d, J=4.6 Hz, 1H), 8.31 (s, 1H, NH), 8.17(m, 1H), 8.15(m, 1H), 7.80, 7.51 (ABq, J=7.2 Hz, 4H), 7.50(m, 1H), 7.26 (m, 1H), 6.59 (s, 1H), 2.73 (q, J=7.4Hz, 2H), 1.29(t, J=7.4 Hz, 3H).

Example 43

Synthesis of [4-(5-Methylthio-3-pyridin-3-yl-pyrazol-1-yl)phenyl]-(2-chloro-6-fluorobenzyl)amine.

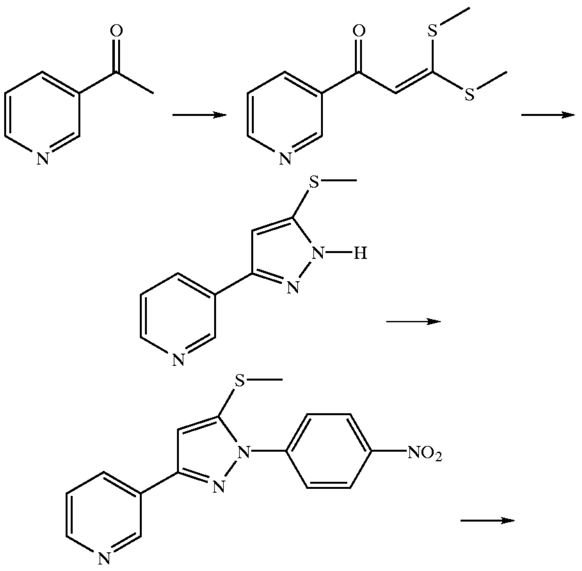

-continued

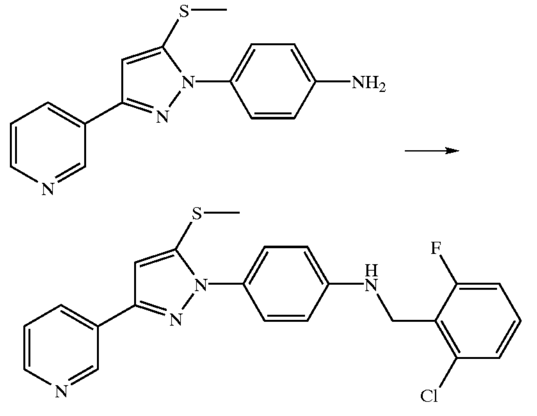

A mixture of 3-acetylpyridine (5g, 41.2 mmol), sodium hydride (60%, 0.3.g, 82.5 mmol), carbon disulfide (3.72 mL, 61.9 mmol) and methyl iodide (7.71 mL, 123.8 mmol) in dry benzene (70 mL) was stirred at 0° C. in an ice-bath under argon atmosphere. Dimethylacetamide (8 mL) was carefully added which initiated a vigorous reaction. The reaction mixture was further stirred for 1 h. The reaction mixture was diluted with ice-water, the aqueous layer was extracted with ethyl acetate and the combined organic extracts were washed with water and dried ($MgSO_4$). The resulting dimethylthiovinyl ketone (5.2 g) was used directly in the next step.

A mixture of the above ketone (4.2 g, 41.2 mmol) and hydrazine hydrate (1 mL, 20.5 mmol) in EtOH (50 mL) was refluxed for 14 h. The reaction mixture was concentrated, diluted with water, extracted with ethyl acetate, the combined organic extracts were washed with water and dried ($MgSO_4$). The crude solid obtained on concentration was recrystallized from EtOAc/hexane to give 5-methylthio-3-(3-pyridinyl)pyrazole (2.0g).

A solution of the above pyrazole(1.94 g, 10.15 mmol) and potassium t-butoxide (1.2 g, 10.6 mmol) in anhydrous DMSO (15 mL) was stirred at room temperature for 5 min and then 4-flouronitrobenzene (1.08 mL, 10.15 mmol) was added. The reaction mixture was heated to 100° C. in an oil bath for 5 h under argon. The reaction mixture was cooled, diluted with water, the yellow solid obtained was filtered, washed with water and dried. The residue obtained was recrystallized from ethyl acetate to give 5-methylthio-1-(4-nitrophenyl)-3-(3-pyridinyl)pyrazole (2.4 g).

To a stirred suspension of the above nitro compound (1.2 g, 3.85 mmol) in glacial acetic acid (40 mL) was added a solution of $SnCl_2.2H_2O$ (6.07 g, 26.9 mmol) in conc. HCl (10 mL) and the reaction was stirred overnight at room temperature. The reaction mixture was diluted with water and brought to pH ~12 by the addition of 5N KOH solution, extracted with EtOAc. The organic layer was washed with water (4×), dried over $MgSO_4$ and concentration to give the corresponding amine (0.7 g).

A solution of the above amine (100 mg, 0.35 mmol) and 2-chloro-6-fluorobenzaldehyde (56 mg, 0.35 mmol) in acetic acid (0.5 mL) and MeOH (4 mL) was stirred at room temperature. Sodium cyanoborohydride (56 mg, 0.88 mmol) was added and the reaction mixture was stirred an additional 24 hr at room temperature. The reaction mixture was concentrated, diluted with EtOAc, washed with water and $NaHCO_3$ solution, and dried ($MgSO_4$). The residue obtained on concentration was flash chromatographed on silica gel to give the title compound (55 mg).

Using Methods analogous to those described above, the following compounds of this invention (Tables 1–6) were prepared.

TABLE 1

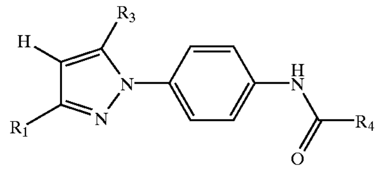

| Cpd. # | $R_1$ | $R_3$ | $R_4$ | m.p. ° C. |
|---|---|---|---|---|
| 529 | $CF_3$ | $CF_3$ | 2-ClPh | 179.5–180 |
| 532 | $CF_3$ | $CF_3$ | 2,4-diClPh | 153.5–154 |
| 533 | $CF_3$ | $CF_3$ | 2,5-diClPh | 165–166 |
| 534 | $CF_3$ | $CF_3$ | 2,3-diClPh | 188.5–190 |
| 535 | $CF_3$ | $CF_3$ | 2,6-diClPh | 220–220.5 |
| 536 | $CF_3$ | $CF_3$ | 3,4-diClPh | 177–178 |
| 538 | $CF_3$ | $CF_3$ | Ph | 243–245 |
| 539 | $CF_3$ | $CF_3$ | 3-ClPh | 160–165 |
| 542 | $CF_3$ | $CF_3$ | 3,5-diClPh | 209–210 |
| 552 | $CF_3$ | $CF_3$ | 4-MePh | 228–230 |
| 553 | $CF_3$ | $CF_3$ | 4-MeOPh | 213.5–215 |
| 567 | $CF_3$ | $CF_3$ | 3-MeOPh | 189–190 |
| 576 | $CF_3$ | $CF_3$ | 3-MePh | 144 |
| 577 | $CF_3$ | $CF_3$ | 2-MeOPh | 101–102 |
| 581 | $CF_3$ | $CF_3$ | 3,4-$(OCH_2O)$Ph | |
| 590 | $CF_3$ | $CF_3$ | 4-(1-imidazolyl)Ph | |
| 607 | $CF_3$ | $CF_3$ | 4-$Me_2N$Ph | |
| C5374 | $CF_3$ | $CF_3$ | 4-ClPh | |
| 696 | $CF_3$ | $CF_3$ | 4-MeSPh | 224–225 |
| 703 | $CF_3$ | $CF_3$ | 4-MeS(O)Ph | 187–188 |
| 710 | $CF_3$ | $CF_3$ | 4-$MeSO_2$Ph | 221–222 |
| 716 | $CF_3$ | $CF_3$ | 4-$Me_2NCH_2$Ph | 159–160 |
| 719 | $CF_3$ | $CF_3$ | 2-$(H_2NSO_2)$Ph | |
| 730 | $CF_3$ | $CF_3$ | 3-$Me_2N$Ph | 181–184 |
| 748 | $CF_3$ | $CF_3$ | 4-CNPh | 177–179 |
| 755 | $CF_3$ | $CF_3$ | 2-$(NO_2)$Ph | |
| 759 | $CF_3$ | $CF_3$ | 3-$MeSO_2$Ph | 209–210 |
| 543 | $CF_3$ | $CF_3$ | 3-Py | 163–166 |
| 544 | $CF_3$ | $CF_3$ | 4-Py | 163–166 |
| 545 | $CF_3$ | $CF_3$ | 2-Py | 167–168 |
| 549 | $CF_3$ | $CF_3$ | 2-Th | 232–234 |
| 574 | $CF_3$ | $CF_3$ | (6-Cl)-3-Py | 209–210 |
| 575 | $CF_3$ | $CF_3$ | (2-Cl)-4-Py | 188–190 |
| 591 | $CF_3$ | $CF_3$ | (2,5-diMe)-2-Thz | |
| 597 | $CF_3$ | $CF_3$ | (2,5-diMe)-3-Furyl | |
| 669 | $CF_3$ | $CF_3$ | (2-Cl)3-Py | 155–156 |
| 676 | $CF_3$ | $CF_3$ | (S)-2-Pyrrolidinyl | 90–91 |
| 687 | $CF_3$ | $CF_3$ | (R)-2-Pyrrolidinyl | 91–92 |
| 688 | $CF_3$ | $CF_3$ | 3-Piperidinyl | 231–233 |
| 698 | $CF_3$ | $CF_3$ | 2-Pyrazinyl | 188–189 |
| 705 | $CF_3$ | $CF_3$ | (2,6-diMeO)-3-Py | 128.5–130 |
| 711 | $CF_3$ | $CF_3$ | 4-Quinolinyl | 204–205 |
| 712 | $CF_3$ | $CF_3$ | 2-Quinoxalinyl | 196 |
| 723 | $CF_3$ | $CF_3$ | (S)-2-Pyrrolidinone-5-yl | 184–185 |
| 725 | $CF_3$ | $CF_3$ | 3-(N—Me)-Piperidinyl | 115–116 |
| 726 | $CF_3$ | $CF_3$ | N-Morpholinyl | 185–186 |
| 727 | $CF_3$ | $CF_3$ | 3-Py(N-oxide) | >275 |
| 728 | $CF_3$ | $CF_3$ | 4-Py(N-oxide) | 235–238 |
| 731 | $CF_3$ | $CF_3$ | (S)-3-Tetrahydroisoquinolinyl | 81–85 |
| 790 | $CF_3$ | $CF_3$ | (2-Cl-5-Br)3Py | 182–184 |
| 530 | $CF_3$ | $CF_3$ | $(CH_2)_2$4ClPh | 169.5–171 |
| 531 | $CF_3$ | $CF_3$ | $CH_2$4-ClPh | 168.5–170 |
| 546 | $CF_3$ | $CF_3$ | $(CH_2)_2$4-(PhC(O))Ph | |
| 547 | $CF_3$ | $CF_3$ | Me | 175–176 |
| 584 | $CF_3$ | $CF_3$ | n-Pentyl | 107–109 |
| 660 | $CF_3$ | $CF_3$ | $C(Cl){=}C(Cl)_2$ | |
| 670 | $CF_3$ | $CF_3$ | 3-(N-Boc)piperidinyl | 81–82 |
| 673 | $CF_3$ | $CF_3$ | $CH_2$4-Py | 217–218 |
| 713 | $CF_3$ | $CF_3$ | $CH_2NHPh$ | 142–144 |
| 715 | $CF_3$ | $CF_3$ | $CH_2$(2-Pyrrolidinone-N-yl) | 168–170 |
| 744 | $CF_3$ | $CF_3$ | $(CH_2)_2C(O)NH_2$ | 227–228 |
| 749 | $CF_3$ | $CF_3$ | $CH_2NMe_2$ | 105–107 |
| 555 | $CF_3$ | Ph | 4-ClPh | 209–210 |
| 561 | t-Bu | t-Bu | 4-ClPh | 208–209.5 |
| 568 | Ph | $CF_3$ | 4-ClPh | 235.5–238 |
| 571 | Me | $CF_3$ | 4-ClPh | 190–192 |
| 572 | $CF_3$ | Me | 4-ClPh | 178–180 |

TABLE 1-continued

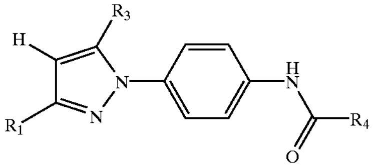

| Cpd. # | $R_1$ | $R_3$ | $R_4$ | m.p. ° C. |
|---|---|---|---|---|
| 602 | $CF_3$ | 2-Furyl | 4-ClPh | 223–224 |
| 603 | 2-Furyl | $CF_3$ | 4-ClPh | 198–199 |
| 604 | $CF_3$ | Cl | 4-ClPh | 175–177 |
| 628 | 2-Thienyl | $CF_3$ | 4-ClPh | 174—174 |
| 629 | $CF_3$ | 2-Thienyl | 4-ClPh | 258–259 |
| 630 | t-Butyl | $CF_3$ | 4-ClPh | |
| 631 | $CF_3$ | t-Butyl | 4-ClPh | |
| 633 | $CO_2Et$ | Me | 4-ClPh | |
| 649 | Me | Ph | 4-ClPh | |
| 650 | $CF_3$ | $CH_2NMe_2$ | 4-ClPh | |
| 652 | t-Butyl | $CF_3$ | 4-ClPh | |
| 661 | $CF_3$ | $CH_2OH$ | 4-ClPh | |
| 662 | $CF_3$ | i-Pr | 4-ClPh | 133–134.5 |
| 664 | Me | 3-Py | 4-ClPh | 181–184 |
| 668 | i-Pr | $CF_3$ | 4-ClPh | 201–203 |
| 674 | 2-Furyl | $CF_3$ | 3-Py | 174–175 |
| 677 | $CF_3$ | $CH_2O$-t-Bu | 4-ClPh | |
| 678 | 2-Furyl | 2-Furyl | 4-ClPh | 215–217 |
| 682 | 3-Py | $CF_3$ | 4-ClPh | 238–241 |
| 684 | t-Bu | $Me_2N$ | 4-ClPh | |
| 685 | $CF_3$ | 3-Py | 4-ClPh | 215–218 |
| 686 | Me | 2-Furyl | 4-ClPh | 193–194.5 |
| 697 | Et | $CF_3$ | 3-Py | 196–198 |
| 706 | $CF_3$ | Et | 3-Py | 197–199 |
| 707 | 2-THF | $CF_3$ | 3-Py | 135–137 |
| 708 | $CF_3$ | $CH_2OMe$ | 4-ClPh | |
| 709 | $CF_3$ | $CH_2OMe$ | 3-Py | |
| 722 | 3-Py(N-oxide | $CF_3$ | 4-ClPh | 143–150 |
| 724 | $CF_3$ | Me | 3-Py | 164–166 |
| 733 | $CF_3$ | 2-Oxazolidinyl | 3-Py | 230–231 |
| 736 | $CF_3$ | 2-Thiazolyl | 3-Py | 238–240 |
| 737 | $CF_3$ | 4-$Me_2$NPh | 3-Py | 114–116 |
| 739 | 3-Py | $CF_3$ | 3-Py | 182–184 |
| 743 | 2-Pyrazinyl | Et | 3-Py | 199–202 |
| 746 | 2-Thiazolyl | $CF_3$ | 3-Py | 225–227 |
| 756 | $CH_2OMe$ | Me | 4-ClPh | 180–181 |
| 760 | EtO | $CF_3$ | 4-ClPh | 189–190 |
| 761 | EtO | $CF_3$ | 3-Py | 174–175 |
| 763 | 3-Py | $CF_3$ | (5-Br)-3-Py | 207–209 |
| 768 | $CF_3$ | 4-Py | 3-Py | 191–193 |
| 776 | 3-Py | $CF_3$ | (2-Cl)-3-Py | 150–151 |
| 777 | 3-Py | $CF_3$ | 4-Py | 220–221 |
| 779 | $CF_3$ | Me | 4-t-BuPh | 195–197 |
| 780 | $CF_3$ | Me | Cyclopentyl | 176–178 |
| 781 | $CF_3$ | Me | 3-THF | |
| 782 | 3-Py | $CF_3$ | 4-Imidazolyl | 205–210 |
| 784 | $CF_3$ | CN | 4-ClPh | 186–187 |
| 786 | Et | Ph | 3-Py | 194–195 |
| 787 | Et | Ph | 4-Py | 219–221 |
| 788 | Et | i-Pr | 4-Py | 195–196 |
| 789 | Et | i-Pr | 3-Py | 194–196 |
| 792 | $CF_3$ | Me | $(CH_2)_2SO_2Ph$ | |
| 793 | $CF_3$ | Me | 2-Indanyl | |
| 794 | $CF_3$ | Me | 2-Indolyl | |
| 795 | $CF_3$ | Me | $(CH_2)_2$-3-indolyl | |
| 799 | t-Bu | Me | 4-ClPh | 203–204 |
| 800 | t-Bu | Me | 3-Py | 161–163 |
| 805 | $CF_3$ | Me | CH═CH(3,4-diOMePh) | |
| 807 | 3-Py | $CF_3$ | (2-MeS)3-Py | 205–206 |
| 808 | i-Pr | Ph | 3-Py | 167–168 |
| 813 | i-Pr | Me | 3-Py | 149–151 |
| 814 | Me | i-Pr | 3-Py | 88–90 |
| 816 | $CF_3$ | Me | 4-$NO_2$Ph | |
| 820 | $CF_3$ | Me | i-Pr | |
| 821 | Et | Et | 3-Py | 182–184 |
| 823 | $CH_2OMe$ | $CF_3$ | 4-ClPh | 173–174 |
| 824 | $CH_2OMe$ | $CF_3$ | 3-Py | 134–135 |

TABLE 1-continued

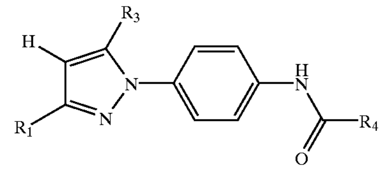

| Cpd. # | $R_1$ | $R_3$ | $R_4$ | m.p. ° C. |
|---|---|---|---|---|
| 825 | 3-Py | $CF_3$ | (2-MeSO)3-Py | 243–244 |
| 826 | i-Pr | Et | 3-Py | 178–179 |
| 832 | $CF_3$ | Me | 4-i-PrPh | |
| 833 | $CF_3$ | Me | 4-EtPh | |
| 836 | $CF_3$ | Me | (2-Me)3-Py | |
| 837 | $CF_3$ | Me | (6-Me)3-Py | |
| 838 | $CF_3$ | Me | (2-MeO)3-Py | |
| 843 | 3-THF | $CF_3$ | 4-Py | 141–143 |
| 844 | 3-THF | $CF_3$ | (2-MeS-5-Br)4-pyrimidinyl | 131–134 |
| 845 | $CF_3$ | Me | 4-$CF_3$Ph | |
| 846 | $CF_3$ | Me | 4-$CO_2$MePh | |
| 847 | $CF_3$ | Me | 4-i-PrOPh | |
| 848 | $CF_3$ | Me | (4-Ph)Ph | |
| 850 | $CF_3$ | Me | 4-n-PentylPh | |
| 852 | $CF_3$ | Me | 3-Thienyl | |
| 854 | $CF_3$ | Me | (3-Me)2-Furyl | |
| 856 | $CF_3$ | Me | 2-MeCyclohexyl | |
| 857 | $CF_3$ | Me | 3-MeCyclohexyl | |
| 858 | $CF_3$ | Me | 4-MeCyclohexyl | |
| 859 | $CF_3$ | Me | 4-(MeO)Cyclohexyl | |
| 861 | $CF_3$ | Me | 4-n-PentylCyclohexyl | |
| 871 | $CF_3$ | Me | (2-Me-6-Cl)4-Py | |
| 872 | $CF_3$ | Me | 4-FPh | |
| 873 | $CF_3$ | Me | 4-MeC(O)NHPh | |
| 874 | $CF_3$ | Me | $CH_2$4-ClPh | |
| 875 | $CF_3$ | Me | $CH_2$(7-$Me_2$N Coumarin-4-yl) | |
| 876 | $CF_3$ | Me | N-MePyrrolidin-2-One-4-yl | |
| 878 | 3-Py | $CF_3$ | (2-OMe)-3-Py | 163–4 |
| 879 | 3-Py | $CF_3$ | 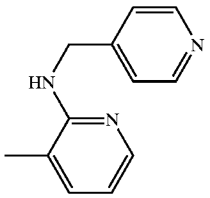 | 107–8 |
| 880 | 3-Py | $CF_3$ | (2-DImethylamino)-3-Py | 188–189 |
| 881 | 3-Py | $CF_3$ | (2-Cl)-4-Py | 193–194 |
| 882 | 3-Py | $CF_3$ | 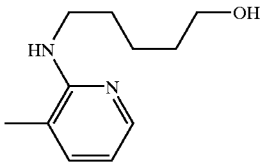 | 95–96 |
| 883 | 3-Py | $CF_3$ | 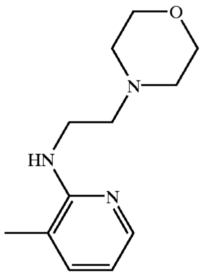 | 85–87 |
| 888 | $CF_3$ | Me | 2-Napthyl | |

TABLE 1-continued
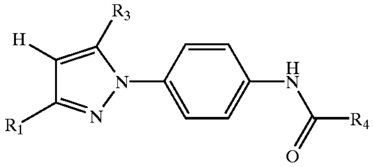
| Cpd. # | $R_1$ | $R_3$ | $R_4$ | m.p. ° C. |
|---|---|---|---|---|
| 889 | $CF_3$ | Me | 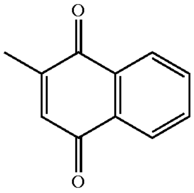 | |
| 890 | $CF_3$ | Me | 6-Quinolinyl | |
| 891 | $CF_3$ | Me | 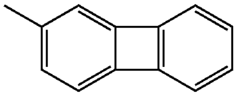 | |
| 892 | $CF_3$ | Me | 1-Napthyl | |
| 893 | $CF_3$ | Me | 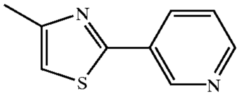 | |
| 894 | $CF_3$ | Me | 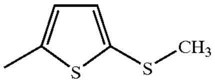 | |
| 896 | $CF_3$ | Me | 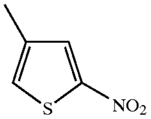 | |
| 897 | $CF_3$ | Me | 3-Quinolinyl | |
| 899 | $CF_3$ | Me | (1-Et-3-Me)Pyrazol-5-yl | |
| 902 | $CF_3$ | Me | (1-Me)Pyrrol-2-yl | |
| 903 | $CF_3$ | Me | 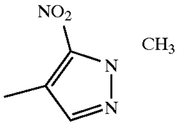 | |
| 909 | $CF_3$ | Me | 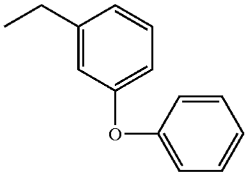 | |
| 910 | $CF_3$ | Me | Cyclohexen-1-yl | |
| 911 | $CF_3$ | Me | 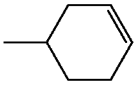 | |

TABLE 1-continued
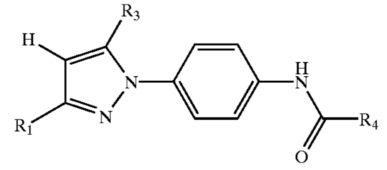
| Cpd. # | $R_1$ | $R_3$ | $R_4$ | m.p. ° C. |
|---|---|---|---|---|
| 912 | $CF_3$ | Me | 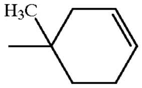 | |
| 913 | $CF_3$ | Me | (1-Me)cyclohexyl | |
| 914 | $CF_3$ | Me | 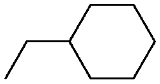 | |
| 915 | $CF_3$ | Me | 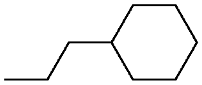 | |
| 915 | $CF_3$ | Me | 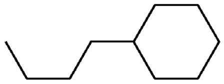 | |
| 917 | $CF_3$ | Me | 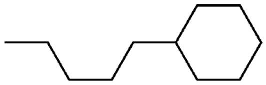 | |
| 918 | $CF_3$ | Me | 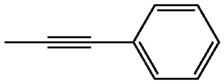 | |
| 919 | $CF_3$ | Me | 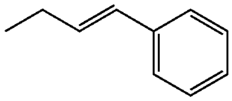 | |
| 920 | $CF_3$ | Me | 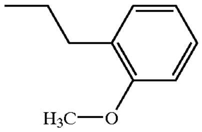 | |
| 921 | $CF_3$ | Me | 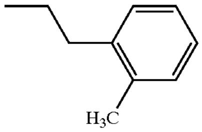 | |
| 922 | $CF_3$ | Me | 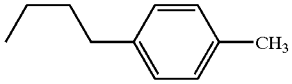 | |
| 923 | $CF_3$ | Me | 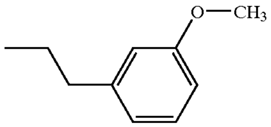 | |

TABLE 1-continued

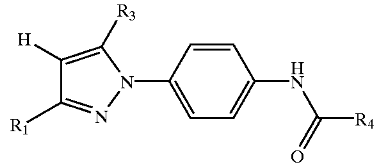

| Cpd. # | $R_1$ | $R_3$ | $R_4$ | m.p. ° C. |
|---|---|---|---|---|
| 924 | $CF_3$ | Me | 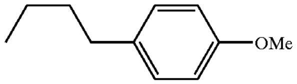 | |
| 925 | $CF_3$ | Me | 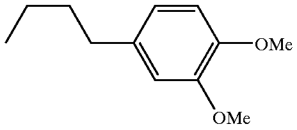 | |
| 927 | 2-Furyl | 2-Furyl | 3-Py | oil |
| 928 | i-Pr | 3-Py | 4-Py | oil |
| 931 | $CF_3$ | Me | CH(Me)Et | |
| 932 | $CF_3$ | Me | $CH_2CH{=}CHEt$ | |
| 933 | $CF_3$ | Me | $CH(Me)CH_2CH{=}CH_2$ | |
| 934 | $CF_3$ | Me | CH(Et)Et | |
| 935 | $CF_3$ | Me | $CH2C(Me)_3$ | |
| 936 | $CF_3$ | Me | $(CH_2)_2CH(Me)Me$ | |
| 937 | $CF_3$ | Me | $CH_2CH_2NO_2$ | |
| 938 | $CF_3$ | Me | $C(Me)_2CH_2CH{=}CH_2$ | |
| 939 | $CF_3$ | Me | $C(Me)_2(CH_2)_2Me$ | |
| 940 | $CF_3$ | Me | (1-Methyl)cyclopropyl | |
| 941 | $CF_3$ | Me | 2-(Methyl)cyclopropyl | |
| 942 | $CF_3$ | Me | (2,2,3,3-tetramethyl)cyclopropyl | |
| 943 | $CF_3$ | Me | Cyclobutyl | |
| 944 | $CF_3$ | Me | 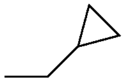 | |
| 945 | $CF_3$ | Me | Cycloheptyl | |
| 946 | $CF_3$ | Me | 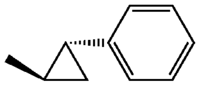 | |
| 947 | $CF_3$ | Me | Cyclopenten-1-yl | |
| 949 | $CF_3$ | Me | 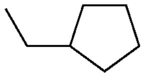 | |
| 950 | $CF_3$ | Me | $(CH_2)_2$Cyclopentyl | |
| 951 | $CF_3$ | Me | 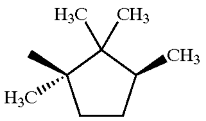 | |
| 952 | $CF_3$ | Me | 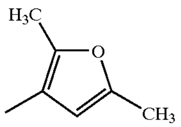 | |
| 954 | $CF_3$ | Me | (5-Me)-2-Thienyl | |
| 955 | Et | 3-Py | | |
| 956 | n-Heptyl | 3-Py | 3-Py | |

TABLE 1-continued
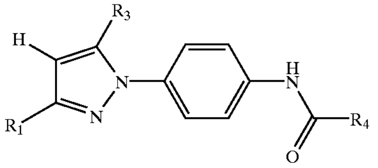
| Cpd. # | $R_1$ | $R_3$ | $R_4$ | m.p. ° C. |
|---|---|---|---|---|
| 958 | $CF_3$ | Me | 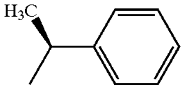 | |
| 959 | $CF_3$ | Me | 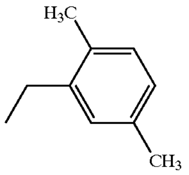 | |
| 962 | $CF_3$ | Me | 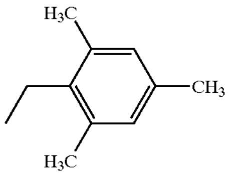 | |
| 963 | $CF_3$ | Me | 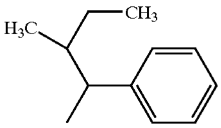 | |
| 964 | $CF_3$ | Me | 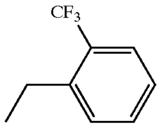 | |
| 969 | $CF_3$ | Me | 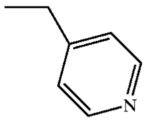 | |
| 970 | $CF_3$ | Me | 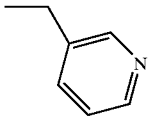 | |
| 971 | $CF_3$ | Me | 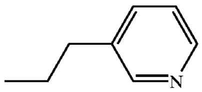 | |
| 972 | $CF_3$ | Me | 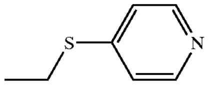 | |
| 973 | $CF_3$ | Me | (4-vinyl)Ph | |
| 974 | $CF_3$ | Me | (4-Acetyl)Ph | |
| 975 | $CF_3$ | Me | (4-n-Pr)Ph | |
| 976 | $CF_3$ | Me | (4-$CF_3$O)Ph | |
| 977 | 2-THF | Et | 3-Py | 119–121 |

TABLE 1-continued
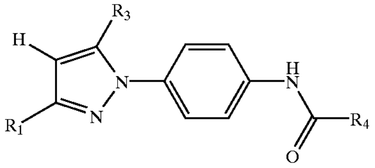
| Cpd. # | $R_1$ | $R_3$ | $R_4$ | m.p. ° C. |
|---|---|---|---|---|
| 978 | $CF_3$ | Me | 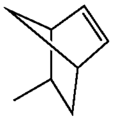 | |
| 979 | $CF_3$ | Me | 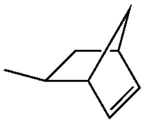 | |
| 980 | $CF_3$ | Me | 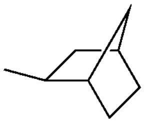 | |
| 981 | $CF_3$ | Me | 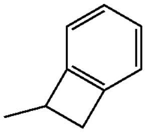 | |
| 982 | $CF_3$ | Me | 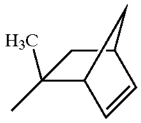 | |
| 983 | $CF_3$ | Me | 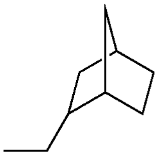 | |
| 984 | $CF_3$ | Me | 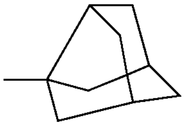 | |
| 985 | $CF_3$ | Me | 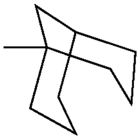 | |
| 988 | $CF_3$ | Me | 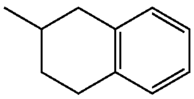 | |
| 991 | $CF_3$ | Me | 2-Quinolinyl | |
| 992 | $CF_3$ | Me | 4-Quinolinyl | |

TABLE 1-continued
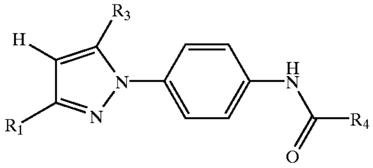
| Cpd. # | $R_1$ | $R_3$ | $R_4$ | m.p. ° C. |
|---|---|---|---|---|
| 993 | $CF_3$ | Me | 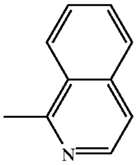 | |
| 994 | $CF_3$ | Me | 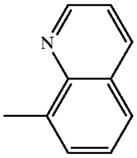 | |
| 995 | $CF_3$ | Me | 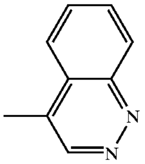 | |
| 996 | $CF_3$ | Me | 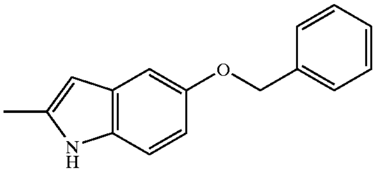 | |
| 997 | $CF_3$ | Me | 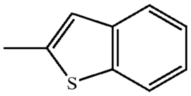 | |
| 998 | $CF_3$ | Me | (5-n-Bu)-3-Py | |
| 999 | $CF_3$ | Me | [2-(1-Pyrrolyl)]Ph | |
| 1000 | $CF_3$ | Me | 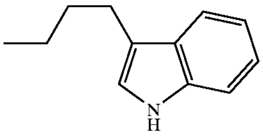 | |
| 1001 | $CF_3$ | Me | 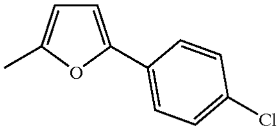 | |
| 1002 | $CF_3$ | Me | 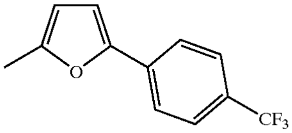 | |

TABLE 1-continued
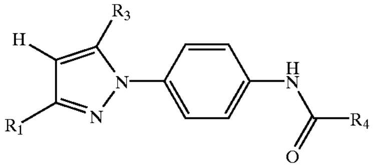
| Cpd. # | $R_1$ | $R_3$ | $R_4$ | m.p. ° C. |
|---|---|---|---|---|
| 1003 | $CF_3$ | Me | 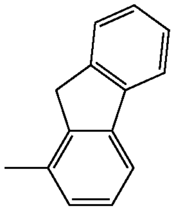 | |
| 1004 | $CF_3$ | Me | 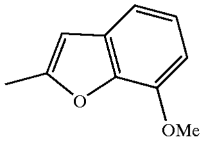 | |
| 1005 | $CF_3$ | Me | 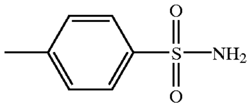 | |
| 1006 | $CF_3$ | Me | 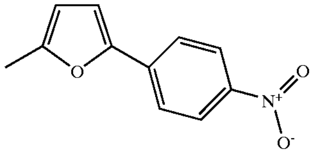 | |
| 1008 | $CF_3$ | Me | 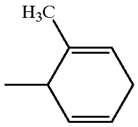 | |
| 1010 | $CF_3$ | Me | 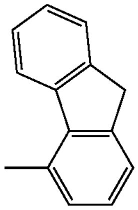 | |
| 1011 | n-Pr | $CF_3$ | 3-Py | 122–123 |
| 1012 | $CF_3$ | n-Propyl | 3-Py | 178–179 |
| 1013 | $CF_3$ | Me | 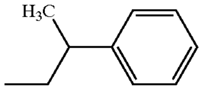 | |
| 1014 | $CF_3$ | Me | 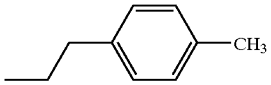 | |
| 1015 | $CF_3$ | Me | (2-Ethoxy)Phenyl | |

TABLE 1-continued
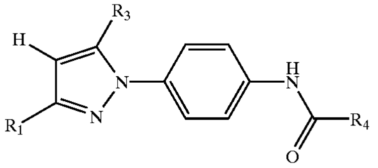
| Cpd. # | $R_1$ | $R_3$ | $R_4$ | m.p. ° C. |
|---|---|---|---|---|
| 1017 | $CF_3$ | Me | 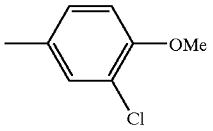 | |
| 1018 | $CF_3$ | Me | 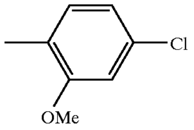 | |
| 1019 | $CF_3$ | Me | 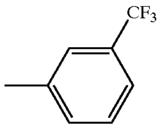 | |
| 1021 | [5-(3-Py)]-2-Furyl | $CF_3$ | 3-Py | 218–219 |
| 1022 | [5-(4-Py)]-2-Furyl | $CF_3$ | 3-Py | 175–180 |
| 1023 | [5-(5-Pyrimidinyl)]-2-Furyl | $CF_3$ | 3-Py | 247–249 |
| 1024 | 3-Py | Et | (6-Cl)-3-Py | |
| 1026 | $CF_3$ | Me | 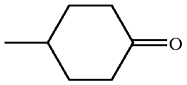 | |
| 1027 | $CF_3$ | Me | 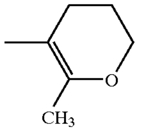 | |
| 1028 | $CF_3$ | Me | 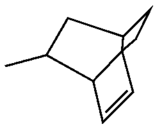 | |
| 1029 | $CF_3$ | Me | 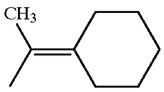 | |
| 1030 | $CF_3$ | Me | 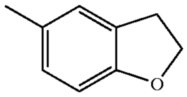 | |
| 1031 | $CF_3$ | Me | 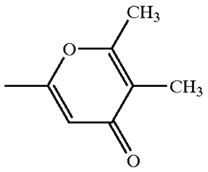 | |

TABLE 1-continued
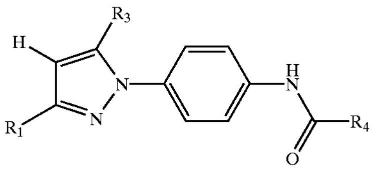
| Cpd. # | $R_1$ | $R_3$ | $R_4$ | m.p. ° C. |
|---|---|---|---|---|
| 1032 | $CF_3$ | Me | 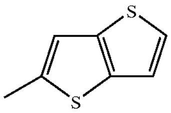 | |
| 1033 | $CF_3$ | Me | 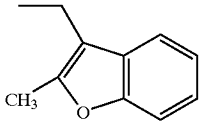 | |
| 1034 | $CF_3$ | Me | 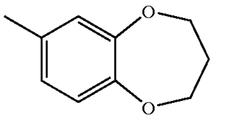 | |
| 1035 | $CF_3$ | Me | 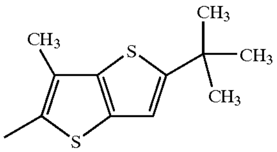 | |
| 1036 | $CF_3$ | Me | 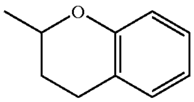 | |
| 1037 | $CF_3$ | Me | 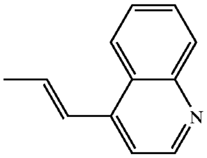 | |
| 1040 | $CF_3$ | Me | 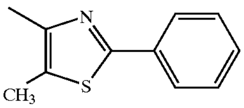 | |
| 1041 | $CF_3$ | Me | 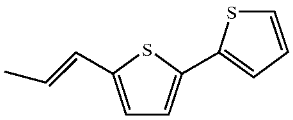 | |

TABLE 1-continued
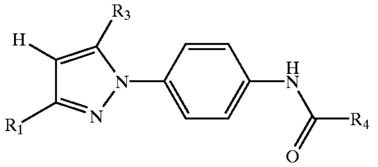
| Cpd. # | $R_1$ | $R_3$ | $R_4$ | m.p. ° C. |
|---|---|---|---|---|
| 1042 | $CF_3$ | Me | 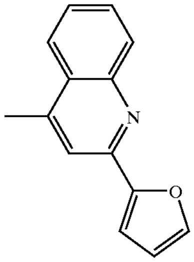 | |
| 1043 | $CF_3$ | Me | 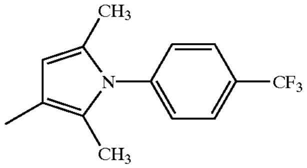 | |
| 1047 | $CF_3$ | Me | 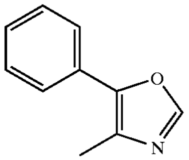 | |
| 1048 | $CF_3$ | Me | 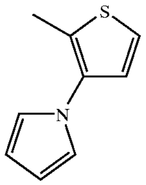 | |
| 1050 | $CF_3$ | Me | 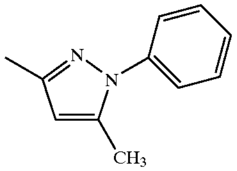 | |
| 1051 | $CF_3$ | Me | 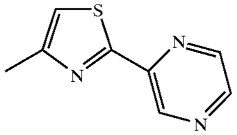 | |
| 1052 | $CF_3$ | Me | 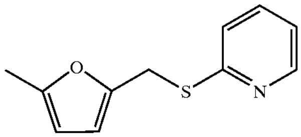 | |

TABLE 1-continued
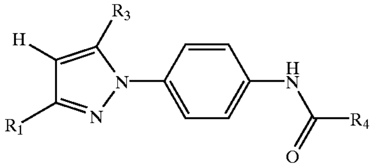
| Cpd. # | $R_1$ | $R_3$ | $R_4$ | m.p. ° C. |
| --- | --- | --- | --- | --- |
| 1053 | $CF_3$ | Me | 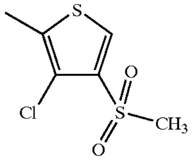 | |
| 1054 | $CF_3$ | Me | 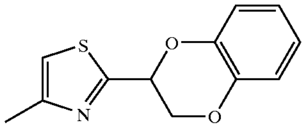 | |
| 1055 | $CF_3$ | Me | 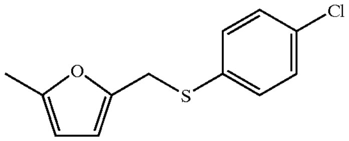 | |
| 1056 | (5-Br)-2-furyl | $CF_3$ | 3-Py | 206–209 |
| 1057 | 2-Py | $CF_3$ | 3-Py | 190–192 |
| 1058 | $CF_3$ | 2-Py | 3-Py | 168–170 |
| 1061 | $CF_3$ | Me | 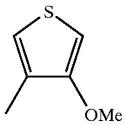 | |
| 1062 | $CF_3$ | Me | 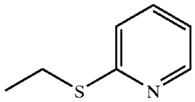 | |
| 1065 | $CF_3$ | Me | 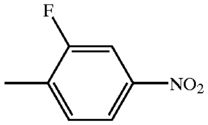 | |
| 1066 | $CF_3$ | Me | 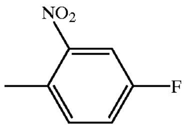 | |
| 1069 | (4-Fluoro)Ph | MeS | 3-Py | 208–210 |
| 1070 | 2-THF | $CF_3$ | (4-Cyano)Phenyl | |
| 1071 | 2-THF | $CF_3$ | 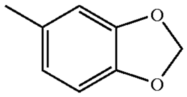 | 185–6 |
| 1072 | 4-Py | $CF_3$ | 3-Py | 210–212 |
| 1075 | $CF_3$ | 2-Furyl | 3-Py | 219–220 |

TABLE 1-continued
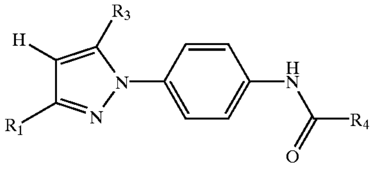
| Cpd. # | $R_1$ | $R_3$ | $R_4$ | m.p. ° C. |
|---|---|---|---|---|
| 1076 | 2-THF | $CF_3$ | (3,5-Dimethyl)-4-Isoxazolyl | 132–134 |
| 1077 | 2-Furyl | MeS | (4-Chloro)Phenyl | 176–178 |
| 1079 | (2-OMe)-3-Py | Et | 3-Py | |
| 1080 | (4-Cyano)Phenyl | Et | 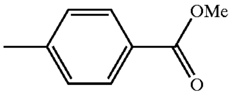 | |
| 1081 | Et | Et | 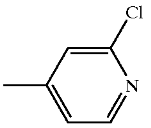 | 198–200 |
| 1083 | 3-Py | i-Pr | 3-Py | 90–92 |
| 1084 | $CF_3$ | (5-Bromo)-2-furanyl | 3-Py | 205–207 |
| 1087 | $CF_3$ | (5-(5-pyrimidinyl)-2-furanyl | 3-Py | 239–243 |
| 1088 | MeS | 2-Furyl | 4-ClPh | 186–188 |
| 1089 | Et | Et | 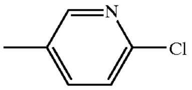 | 170–172 |
| 1090 | 3-Py | $CF_3$ | 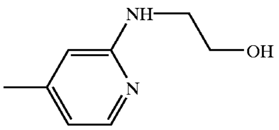 | 113–115 |
| 1091 | 3-Py | $CF_3$ | 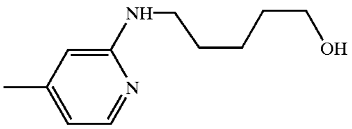 | 93–95 |
| 1092 | 3-Py | $CF_3$ | 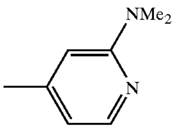 | 183–185 |
| 1093 | 3-Py | Et | 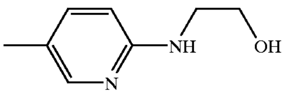 | 95–97 |
| 1094 | 3-Py | Et | 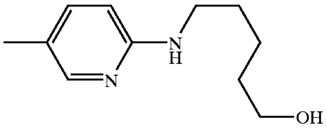 | 68–70 |

TABLE 1-continued
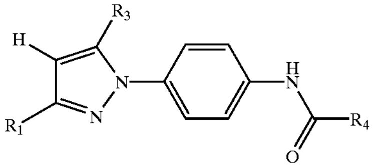
| Cpd. # | $R_1$ | $R_3$ | $R_4$ | m.p. ° C. |
|---|---|---|---|---|
| 1095 | 3-Py | Et | 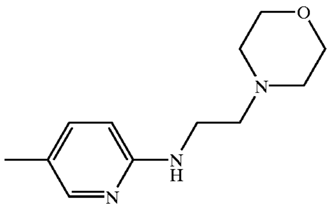 | 72–75 |
| 1096 | 3-Py | Et | 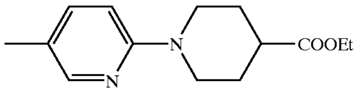 | |
| 1097 | 3-Py | Et | 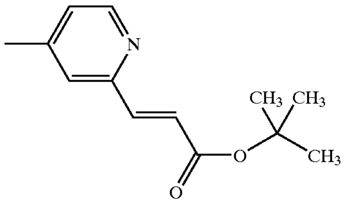 | 85–87 |
| 1100 | 2-THF | $CF_3$ | 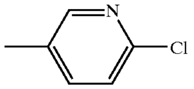 | |
| 1101 | 2-furanyl | S(O)Me | (4-Chloro)Phenyl | 110—110 |
| 1102 | (5-Bromo)-3-Py | Et | 3-Py | 220–222 |
| 1103 | 2-THF | $CF_3$ | (5-Nitro)-n-Pentyl | 98-100 |
| 1106 | MeO | Et | 3-Py | |
| 1107 | $CF_3$ | Me | 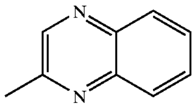 | |
| 1108 | $CF_3$ | Me | 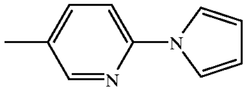 | |
| 1109 | $CF_3$ | Me | 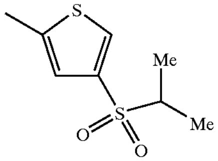 | |
| 1110 | $CF_3$ | Me | 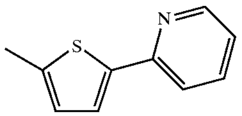 | |
| 1111 | $CF_3$ | Me | (5-Methylsulfonyl)-2-thienyl | |

TABLE 1-continued
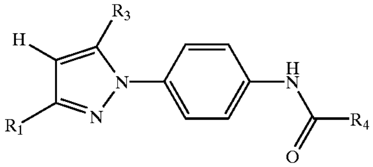
| Cpd. # | $R_1$ | $R_3$ | $R_4$ | m.p. ° C. |
|---|---|---|---|---|
| 1112 | $CF_3$ | Me | 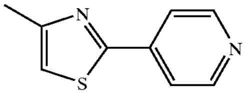 | |
| 1113 | $CF_3$ | Me | 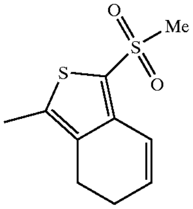 | |
| 1114 | $CF_3$ | Me | 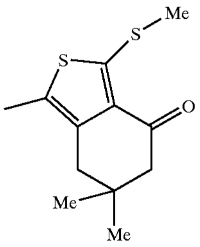 | |
| 1115 | $CF_3$ | Me | 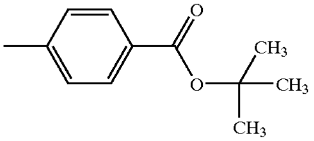 | |
| 1117 | $CF_3$ | Me | (4-n-Butyl)Phenyl | |
| 1118 | $CF_3$ | Me | (3-Methoxycarbonyl)Phenyl | |
| 1119 | $CF_3$ | Me | (4-n-Propyloxy)Phenyl | |
| 1120 | $CF_3$ | Me | (4-n-Butyloxy)Phenyl | |
| 1121 | $CF_3$ | Me | 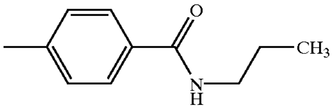 | |
| 1122 | $CF_3$ | Me | 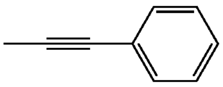 | |
| 1123 | $CF_3$ | Me | (4-Ethoxycarbonyl)Phenyl | |
| 1126 | 2-Py | CN | 3-Py | 237–239 |
| 1128 | Dimethylaminomethyl | CF3 | (4-Chloro)Phenyl | 177–178 |
| 1130 | (2-Chloro)-3-Pyridinyl | Et | 3-Py | 203–205 |
| 1131 | (6-Chloro)-3-Pyridinyl | Et | 3-Py | 228–230 |
| 1134 | 2-THF | CF3 | (2,4-Dinitro)Phenyl | 180–182 |
| 1138 | $CF_3$ | Me | 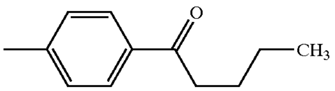 | |

TABLE 1-continued
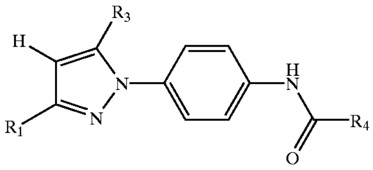
| Cpd. # | $R_1$ | $R_3$ | $R_4$ | m.p. ° C. |
|---|---|---|---|---|
| 1139 | $CF_3$ | Me | 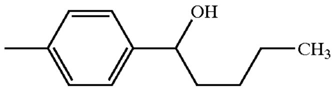 | |
| 1140 | $CF_3$ | Me | 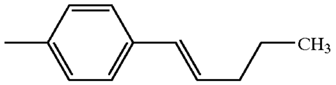 | |
| 1142 | 3-Py | SMe | 3-Py | 183–185 |
| 1149 | $CF_3$ | $CH_3$ | (N-Methyl)-2-indolyl | |
| 1150 | $CF_3$ | $CH_3$ | (2-Nitro-4-chloro)phenyl | |
| 1151 | $CF_3$ | $CH_3$ | (2-phenethyl)phenyl | |
| 1152 | $CF_3$ | $CH_3$ | R-N-Methyl-2-pyrrolidinyl | |
| 1162 | 3-py | Et | $CH{=}CH_2$ | |
| 1163 | $NMe_2$ | c-Pr | 3-Py | |
| 1165 | MeS(O) | 2-Furanyl | (4-Chloro)phenyl | |
| 1167 | i-Pr | Et | (6-Chloro)-3-Py | 166–168 |
| 1169 | 4-Py | Et | 3-Py | 249–251 |
| 1170 | 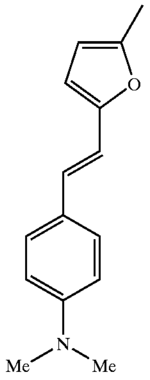 | $CF_3$ | 3-Py | 232 |
| 1171 | 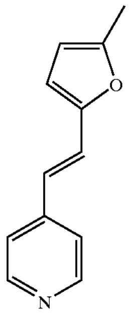 | $CF_3$ | 3-Py | 210–212 |

TABLE 1-continued
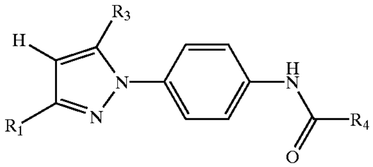
| Cpd. # | $R_1$ | $R_3$ | $R_4$ | m.p. ° C. |
|---|---|---|---|---|
| 1172 | 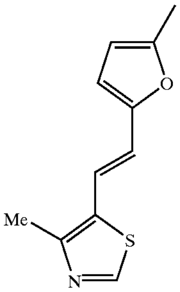 | $CF_3$ | 3-Py | 193–6 |
| 1173 | 3-Py | Et | 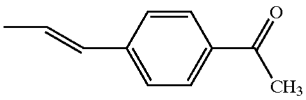 | 245–7 |
| 1174 | 2-furanyl | $NMe_2$ | 3-Py | |
| 1175 | $NMe_2$ | 2-furanyl | 3-Py | |
| 1177 | i-Pr | $CH{=}CH_2$ | 3-Py | 132–134 |
| 1178 | c-Pr | $CF_3$ | 3-Py | 185–186 |
| 1179 | 3-Py | Et | (6-Propyloxy)-3-Py | 70–72 |
| 1180 | 3-Py | Et | 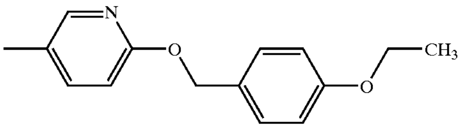 | 200–202 |
| 1183 | 3-Py | Et | 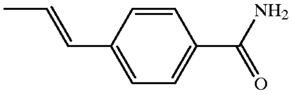 | 263–266 |
| 1184 | 3-Py | Et | 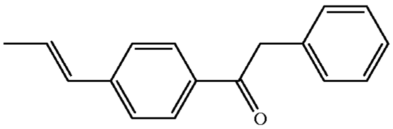 | 196–199 |
| 1185 | 3-Py | Et | 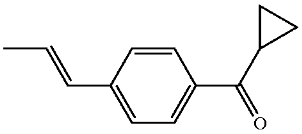 | 215–218 |
| 1189 | $CF_3$ | Me | 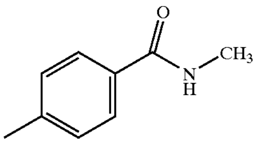 | 273–274 |

TABLE 1-continued
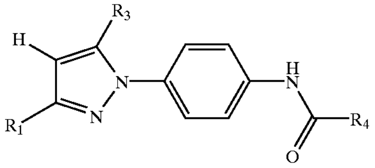
| Cpd. # | $R_1$ | $R_3$ | $R_4$ | m.p. ° C. |
|---|---|---|---|---|
| 1192 | 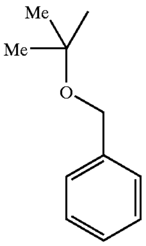 | Et | 3-Py | 123–125 |
| 1193 | $CF_3$ | c-Pr | 3-Py | 181–183 |
| 1194 | 3-py | Et | 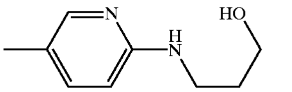 | 180–182 |
| 1195 | 3-py | Et | 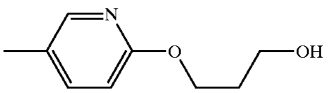 | 153–155 |
| 1196 | 3-py | Et | 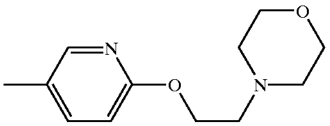 | |
| 1197 | 3-py | Et | 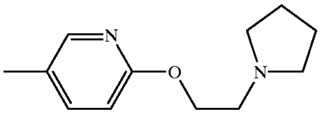 | |
| 1199 | i-Pr | Et | (2-methyl)-3-dihydropyranyl | 133–134 |
| 1200 | i-Pr | Et | (3,5-dimethyl)-4-isoxazolyl | 173–175 |
| 1207 | $CF_3$ | Et | (1,4-dimethyl)-5-imidazolyl | 179–182 |
| 1211 | 3-py | Et | 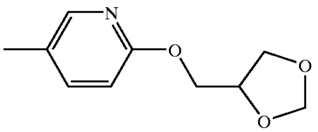 | |
| 1212 | 3-Py | Et | 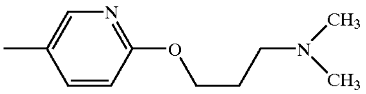 | |
| 1213 | 3-Py | Et | 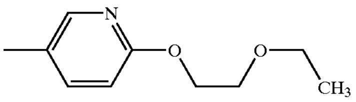 | |
| 1215 | i-Pr | Et | 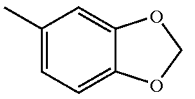 | 214–216 |

TABLE 1-continued
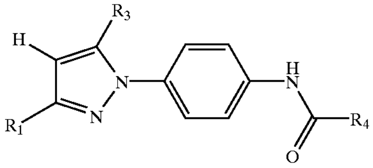
| Cpd. # | $R_1$ | $R_3$ | $R_4$ | m.p. ° C. |
|---|---|---|---|---|
| 1240 | $CF_3$ | Et | 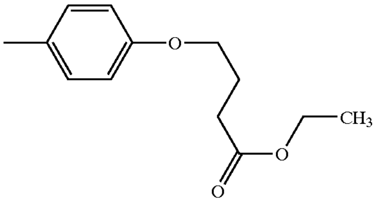 | 169–170 |
| 1241 | $CF_3$ | Et | 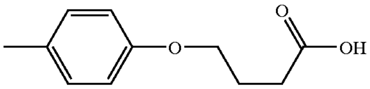 | 183–185 |
| 1242 | $CF_3$ | Et | 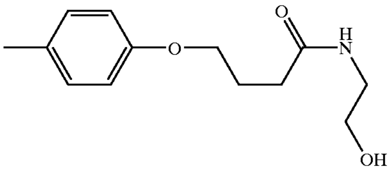 | 236–238 |
| 1243 | $CF_3$ | Et | 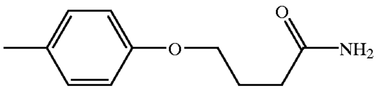 | 208–209 |
| 1244 | 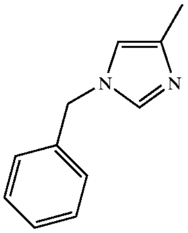 | Me | 3-Py | |
| 1245 | $CF_3$ | $CH_2CN$ | 3-Py | 168–169 |
| 1249 | N-pyrrolidinyl | Et | 3-Py | 188–191 |
| 1265 | $CF_3$ | Et | 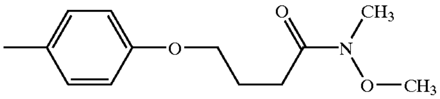 | |
| 1266 | $CF_3$ | Et | 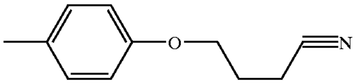 | 151–153 |
| 1267 | 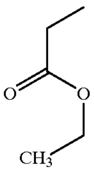 | $CH{=}CH_2$ | 3-Py | |
| 1272 | i-Pr | Et | 4-Py | |

TABLE 1-continued
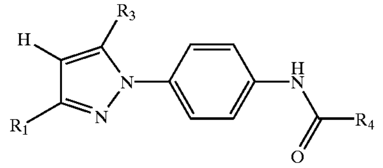
| Cpd. # | $R_1$ | $R_3$ | $R_4$ | m.p. ° C. |
|---|---|---|---|---|
| 1275 | 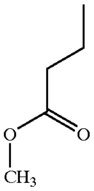 | CH=$CH_2$ | 3-Py | |
| 1277 | EtO— | Et | 3-Py | 127–130 |
| 1278 | EtO(C=O)— | Et | 3-Py | 168–170 |
| 1279 | $CF_3$ | Et | 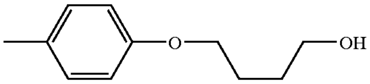 | 179–180 |
| 1280 | $CF_3$ | Et | 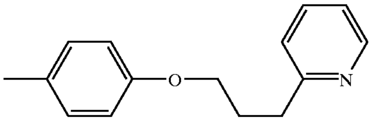 | 181–182 |
| 1284 | $CF_3$ | Et | 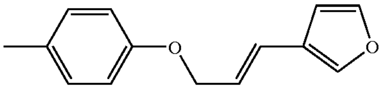 | 193–194 |
| 1285 | i-Pr | Et | 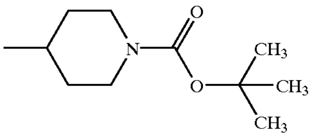 | |
| 1286 | i-Pr | Et | 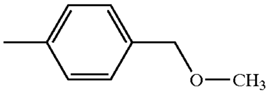 | 144–146 |
| 1304 | i-Pr | Et | 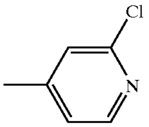 | 213–215 |
| 1306 | 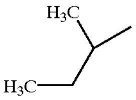 | Et | 3-Py | |
| 1307 | i-Pr | Et | 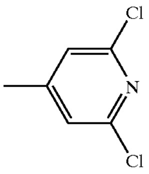 | 88–91 |

TABLE 1-continued
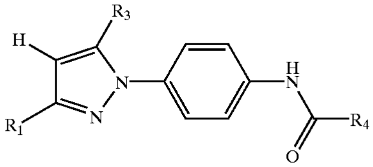
| Cpd. # | $R_1$ | $R_3$ | $R_4$ | m.p. ° C. |
|---|---|---|---|---|
| 1308 | $CF_3$ | Et | 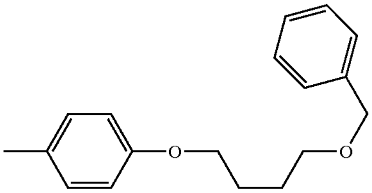 | 92–93 |
| 1309 | $CF_3$ | Et | 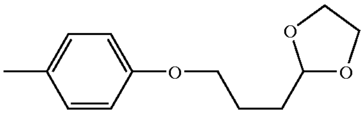 | 158–159 |
| 1310 | $CF_3$ | Et | 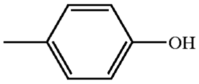 | 282–283 |
| 1311 | 3-Py | Et | 2-Pyrazinyl | 191–192 |
| 1312 | i-Pr | Et | 2-Pyrazinyl | 169–171 |
| 1313 | 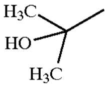 | Et | 3-Py | 81–83 |
| 1316 | i-Pr | Et | 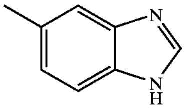 | 128–130 |
| 1317 | i-Pr | Et | 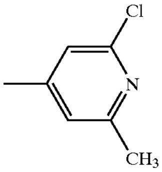 | |
| 1320 | $CF_3$ | Et | 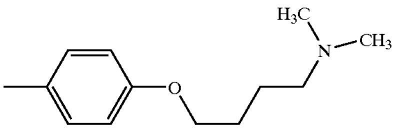 | |
| 1321 | $CF_3$ | Et | 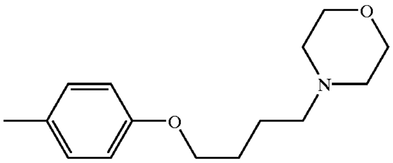 | |

TABLE 1-continued
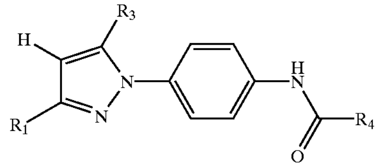
| Cpd. # | $R_1$ | $R_3$ | $R_4$ | m.p. ° C. |
|---|---|---|---|---|
| 1322 | $CF_3$ | Et | 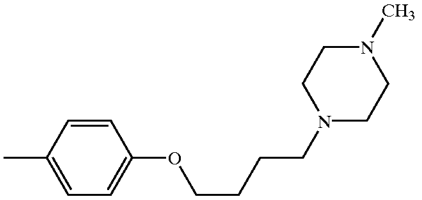 | |
| 1323 | 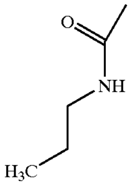 | Et | 3-Py | |
| 1330 | $CF_3$ | Et | 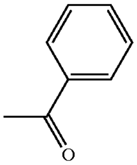 | 125–126 |
| 1334 | 3-Py | Et | 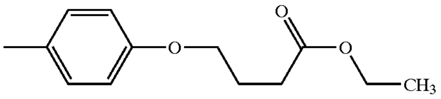 | 161–163 |
| 1335 | 3-Py | Et | 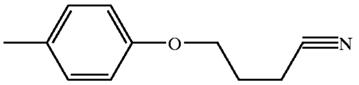 | 144–145 |
| 1336 | 3-Py | Et | 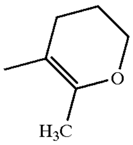 | 157–158 |
| 1338 | CF3 | Et | 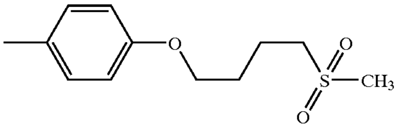 | 169–171 |
| 1339 | c-Pentyl | CF3 | 3-Py | 143–145 |
| 1340 | i-Pr | Et | 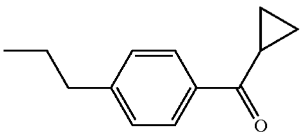 | 130–134 |

TABLE 1-continued
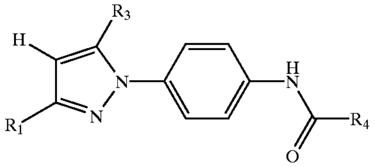
| Cpd. # | $R_1$ | $R_3$ | $R_4$ | m.p. ° C. |
|---|---|---|---|---|
| 1345 | 3-Py | Et | 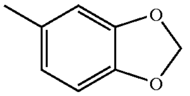 | |
| 1346 | i-Pr | Et | 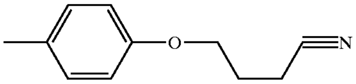 | |
| 1347 | 3-Py | Et | 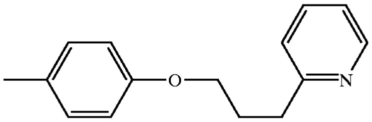 | 143–144 |
| 1348 | 3-Py | Et | 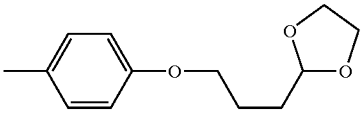 | 136–137 |
| 1349 | 3-Py | Et | 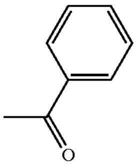 | 136–137 |
| 1350 | 3-Py | Et | 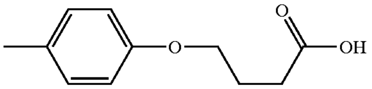 | 219–221 |
| 1352 | 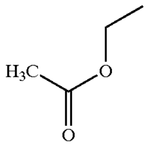 | Et | Py | 105–106 |
| 1360 | 3-Py | Et | 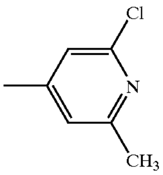 | |
| 1362 | i-Pr | CN | 3-Py | |
| 1363 | i-Pr | Et | 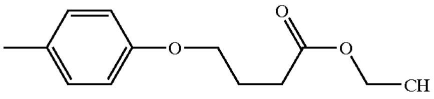 | |

TABLE 1-continued
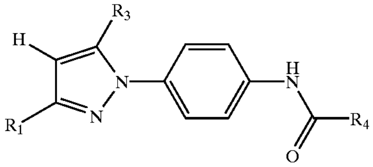
| Cpd. # | $R_1$ | $R_3$ | $R_4$ | m.p. ° C. |
|---|---|---|---|---|
| 1368 | 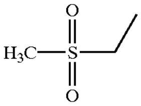 | Et | 3-Py | |
| 1370 | 3-Py | Et | 2-thienyl | |
| 1371 | 3-Py | Et | 3-thienyl | |
| 1372 | 3-Py | Et | 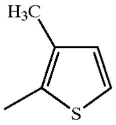 | |
| 1374 | 2-naphthyl | CF3 | 3-Py | 225 |
| 1375 | CF3 | 2-naphthyl | 3-Py | 203 |
| 1378 | 3-Py | Et | 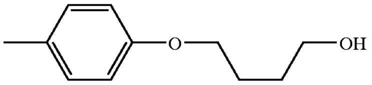 | |
| 1380 | $—CH_2CN$ | Et | 3-Py | |
| 1381 | 3-Py | Et | 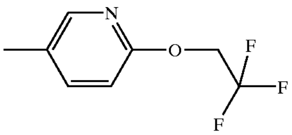 | |
| 1383 | 3-Py | Et | 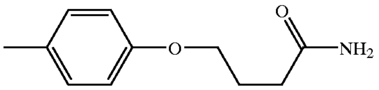 | |
| 1384 | 3-Py | Et | 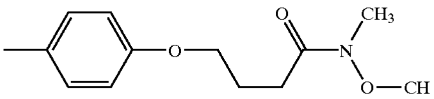 | 161–163 |
| 1385 | $CF_3$ | Et | 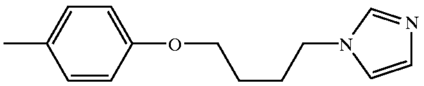 | 201–203 |
| 1394 | 3-Py | Et | 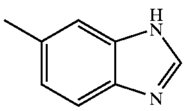 | |
| 1395 | 3-Py | Et | (2-Methyl)-3-Py | |
| 1397 | i-Pr | Et | 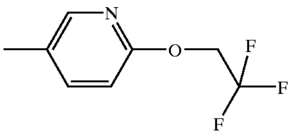 | |

TABLE 1-continued
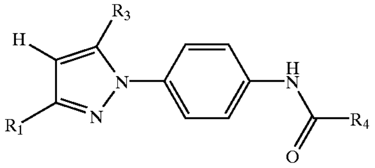
| Cpd. # | $R_1$ | $R_3$ | $R_4$ | m.p. ° C. |
|---|---|---|---|---|
| 1403 | 3-Py | Et | 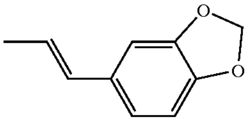 | |
| 1404 | 3-Py | Et | 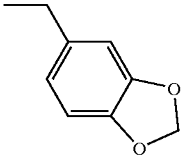 | |
| 1408 | 3-py | Et | (3,5-dimethyl)-5-isoxazolyl | |
| 1412 | 3-py | Et | (2-chloro)-3-py | |
| 1414 | 3-py | Et | (2-methyl)-3-furanyl | |
| 1422 | 3-py | Et | 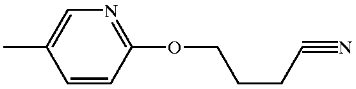 | |
| 1423 | 3-py | Et | 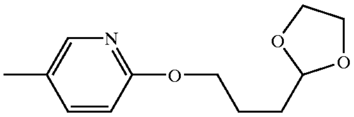 | 150–152 |
| 1426 | 3-py | Et | (2-ethyl)phenyl | |
| 1428 | 3-Py | Et | 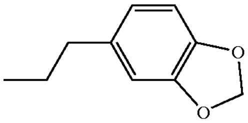 | 157–159 |
| 1429 | 3-py | CN | 3-Py | 230–232 |
| 1432 | 3-Py | Et | (5-Methyl)-4-isoxazolyl | |
| 1448 | CN | 3-Py | 3-Py | 211–212 |
| 1451 | 3-py | Et | (3-methyl-4-vinyl-5-methylthio)-2-thienyl | |
| 1465 | 3-Py | Et | 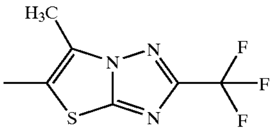 | |
| 1467 | 3-py | Et | (1-methyl)cyclohexyl | 89–90 |
| 1468 | 3-py | Et | (2-methyl)cyclohexyl | 91–92 |
| 1469 | 3-py | Et | cyclohexyl | 152–153 |
| 1473 | 3-py | Et | Cyclopentyl | 134–135 |
| 1484 | 3-py | Et | (2-methyl)phenyl | 179–180 |
| 1494 | i-Pr | Et | 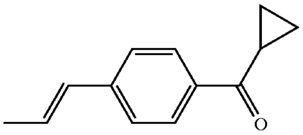 | 210–214 |
| 1502 | 3-py | Et | (6-CF3)-3-py | |

TABLE 1-continued

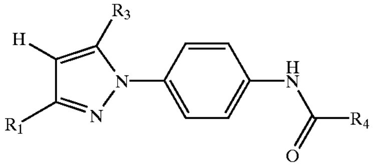

| Cpd. # | $R_1$ | $R_3$ | $R_4$ | m.p. ° C. |
|---|---|---|---|---|
| 1506 | 3-py | Et | (4-CF3)-3-py | |
| 1511 | 3-py | $CH{=}CH_2$ | 3-py | |

TABLE 2

Compounds with L is —NH—

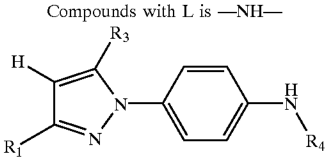

| Cpd. # | $R_1$ | $R_3$ | $R_4$ | m.p. ° C. |
|---|---|---|---|---|
| 580 | $CF_3$ | $CF_3$ | (7-Trifluoromethyl)-4-quinolyl | 230 |
| 615 | $CF_3$ | $CF_3$ | 2-Py | 117–119 |
| 616 | $CF_3$ | $CF_3$ | (3-$NO_2$)-2-Py | 118–120 |
| 644 | $CF_3$ | $CF_3$ | 2-benzimidazolyl | 220–222 |
| 648 | $CF_3$ | $CF_3$ | 1-isoquinolinyl | 205–220 |
| 654 | $CF_3$ | $CF_3$ | 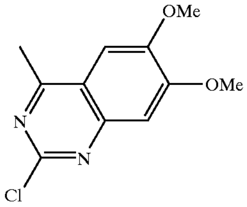 | 240–242 |
| 655 | $CF_3$ | $CF_3$ | (3-Cl)-2-Py | 92–93 |
| 656 | $CF_3$ | $CF_3$ | (3-CN)-2-Py | 133–135 |
| 657 | $CF_3$ | $CF_3$ | 2-Quinolyl | |
| 679 | $CF_3$ | $CF_3$ | (3-Chloro-5-trifluoromethyl)-2-pyridyl | 104–105 |
| 683 | $CF_3$ | Cl | 1-isoquinolinyl | 244–254 |
| 694 | $CF_3$ | $CF_3$ | 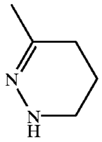 | |
| 699 | $CF_3$ | $CF_3$ | 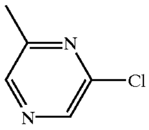 | 167–168 |

TABLE 2-continued

Compounds with L is —NH—

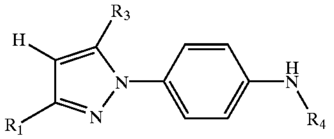

| Cpd. # | $R_1$ | $R_3$ | $R_4$ | m.p. ° C. |
|---|---|---|---|---|
| 702 | $CF_3$ | $CF_3$ | (6-Cl)-Pyrimidin-4-yl | 149–150 |
| 718 | $CF_3$ | $CF_3$ | 2-Pyrazinyl | |
| 720 | $CF_3$ | $CF_3$ | 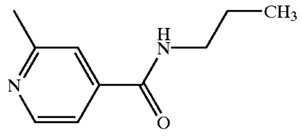 | |
| 732 | 1-Furyl | $CF_3$ | 1-isoquinolinyl | 191–193 |
| 783 | 3-Py | $CF_3$ | 1-isoquinolinyl | 204–205 |
| 1158 | 3-Py | Et | 1-isoquinolinyl | 136–138 |
| 1159 | i-Pr | Et | 1-isoquinolinyl | |
| 1160 | i-Pr | Et | (3-cyano)-2-pyridyl | 123–124 |
| 1333 | i-Pr | Et | cyclohexyl | |
| 1398 | 3-Py | Et | phenyl | |
| 1430 | 3-Py | Et | 3-pyridyl | |
| 1436 | 3-Py | Et | R-1-indanyl | |
| 1437 | 3-Py | Et | S-1-indanyl | |
| 1438 | 3-Py | Et | 3-phenylphenyl | |
| 1439 | 3-Py | Et | 2-phenylphenyl | |
| 1440 | 3-Py | Et | 3-methylphenyl | |
| 1441 | 3-Py | Et | 2-methylphenyl | |
| 1442 | 3-Py | Et | 3-methoxyphenyl | |
| 1443 | 3-Py | Et | 2-methoxyphenyl | |
| 1444 | 3-Py | Et | 1-naphthyl | |
| 1449 | 3-Py | Et | 4-[4,5,6,7-tetrahydrobenzothiopenyl] | 145–146 |
| 1456 | 3-Py | Et | 4-methyl-7-bromo-1-indanyl | |
| 1457 | 3-Py | Et | 8-bromo-1-indanyl | 68–72 |
| 1464 | 3-Py | Et | 2-nitrophenyl | 135–137 |
| 1466 | 3-Py | Et | 2-cyanophenyl | 148–150 |
| 1476 | 3-Py | Et | Cyclohexyl | |
| 1478 | 3-Py | Et | S-1-(1,2,3,4-tetrahydronaphthyl) | 147–149 |
| 1479 | 3-Py | Et | R-1-(1,2,3,4-tetrahydronaphthyl) | 150–152 |
| 1485 | 3-Py | Et | 2-methoxy-6-methylphenyl | |
| 1486 | 3-Py | Et | 2-chloro-6-methylphenyl | |
| 1492 | 3-Py | Et | 4-tetrahydropyranyl | |
| 1493 | 3-Py | Et | 4-ethoxycarbonylcyclohexyl | |
| 1495 | 2-tetrahydrofuranyl | $CF_3$ | 1-isoquinolinyl | |
| 1501 | 3-Py | Et | 2-methylcyclohexyl | |
| 585 | $CF_3$ | $CF_3$ | 4-ClPh | 263–264 |
| 862 | $CF_3$ | $CF_3$ | (6-Cl)-3-Py | 244–245 |
| 863 | $CF_3$ | $CF_3$ | 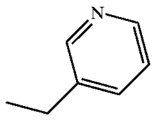 | 143–146 |
| 864 | $CF_3$ | $CF_3$ | (4-Cyano)Phenyl | 247 |
| 886 | $CF_3$ | $CF_3$ | 4-Pyrimidinyl | 218–219 |
| 887 | $CF_3$ | $CF_3$ | 3-Py | 152–155 |

TABLE 3

Compounds with L is —NHC(O)NH—

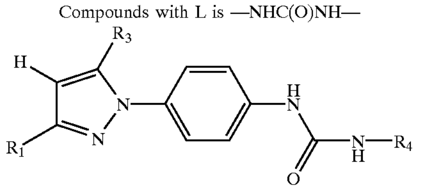

| Cpd. # | $R_1$ | $R_3$ | $R_4$ | m.p. ° C. |
|---|---|---|---|---|
| 908 | $CF_3$ | $CF_3$ | 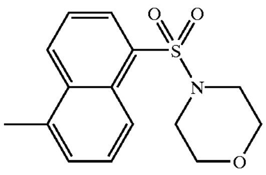 | 220–222 |
| 1387 | 3-Py | Et | Cyclohexyl | 197 |
| 1391 | 3-Py | Et | (2-Methyl-4-Methoxy)Phenyl | 228 |
| 1400 | 3-Py | Et | 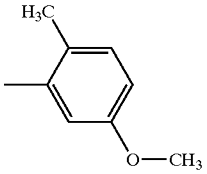 | |
| 1401 | 3-Py | Et | 4-bromophenyl | |
| 1402 | 3-Py | Et | 3-Py | |
| 1405 | 3-Py | Et | (4-Butoxy)Phenyl | 192 |
| 1406 | 3-Py | Et | 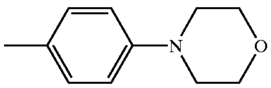 | 227 |
| 1409 | 3-Py | Et | 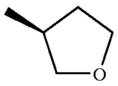 | 153–155 |

TABLE 4

L is —NHC(S)NH—

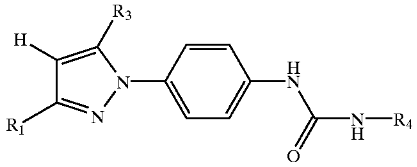

| Cpd. # | $R_1$ | $R_3$ | $R_4$ | m.p. ° C. |
|---|---|---|---|---|
| 1098 | 2-Furanyl | $CF_3$ | 4-ClPh | |
| 1099 | 2-Furanyl | $CF_3$ | 3-Py | |

TABLE 5

L is —NHCH($R_5$)—

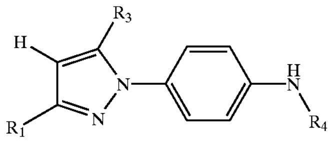

| Cpd. # | $R_1$ | $R_3$ | $R_4$ | $R_5$ | m.p. ° C. |
|---|---|---|---|---|---|
| 740 | $CF_3$ | $CF_3$ | Ph | n-Bu | |
| 753 | $CF_3$ | $CF_3$ | Ph | CN | 119–121 |
| 754 | $CF_3$ | $CF_3$ | Ph | (2-F)-3-Py | |
| 1078 | $CF_3$ | $CF_3$ | Ph | $—CH_2—SO—CH_3$ | |
| 1328 | i-Pr | Et | Ph | $—CH_2OH$ | |
| 1342 | i-Pr | Et | Ph | $—CH_2CH_2OH$ | |
| 1373 | 3-Py | Et | 3-Py | CN | |
| 1474 | 3-Py | Et | Ph | Me | |
| 1480 | 3-Py | Et | Cyclohexyl | Me | |
| 1515 | 3-Py | Et | Cyclopentyl | Me | |

TABLE 6

L is $—NHCH_2$

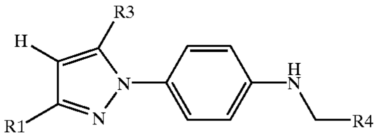

| CMPD # | $R_1$ | $R_3$ | $R_4$ | m.p. ° C. |
|---|---|---|---|---|
| 548 | $CF_3$ | $CF_3$ | (4-Chloro)phenyl | 89–90 |
| 592 | $CF_3$ | Me | (4-Chloro)phenyl | |
| 613 | $CF_3$ | $CF_3$ | Me | 54 |
| 769 | 2-Furanyl | $CF_3$ | 3-Py | 105–106 |
| 842 | 2-THF | $CF_3$ | 3-Py | |
| 1154 | $CF_3$ | Me | 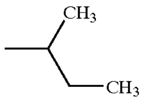 | |

TABLE 6-continued

L is —$NHCH_2$

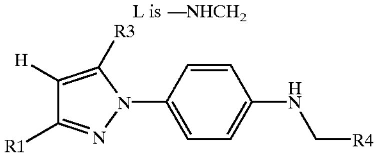

| CMPD # | $R_1$ | $R_3$ | $R_4$ | m.p. ° C. |
|---|---|---|---|---|
| 1155 | $CF_3$ | Me | 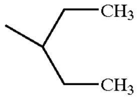 | |
| 1156 | $CF_3$ | Me | 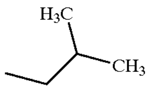 | |
| 1157 | $CF_3$ | Me | 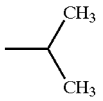 | |
| 1166 | 3-Py | Et | n-Pentyl | |
| 1186 | 3-Py | Et | 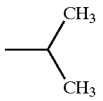 | |
| 1187 | 3-Py | Et | (4-Propyloxy)Phenyl | |
| 1188 | 3-Py | Et | (4-Trifluoromethoxy)Phenyl | |
| 1191 | 3-Py | Et | 3-furanyl | |
| 1198 | i-Pr | Et | 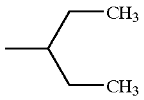 | |
| 1201 | i-Pr | Et | (3,5-Dimethyl)-4-isoxazolyl | 87–88 |
| 1203 | 3-Py | Et | Phenyl | |
| 1204 | 3-Py | Et | (4-Methoxy)Phenyl | |
| 1205 | 3-Py | Et | (4-Bromo)Phenyl | |
| 1206 | i-Pr | Et | 3-Py | |
| 1216 | 3-Py | Et | (2-Chloro)Phenyl | |
| 1218 | 3-Py | Et | (2-Nitro)Phenyl | |
| 1219 | 3-Py | Et | 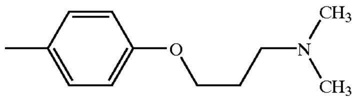 | |
| 1222 | 3-Py | Et | (2,6-Dimethoxy)Phenyl | |
| 1223 | 3-Py | Et | (2-Chloro-6-Nitro)Phenyl | |
| 1224 | 3-Py | Et | (2,5-Dimethyl)Phenyl | |
| 1226 | 3-Py | Et | (3-Methyl)Phenyl | |
| 1227 | 3-Py | Et | (3,5-Dimethoxy)Phenyl | |
| 1228 | 3-Py | Et | (3-Nitro)Phenyl | |
| 1229 | 3-Py | Et | (3,4-Dimethoxy)Phenyl | |
| 1230 | 3-Py | Et | (3-Benzyloxy)Phenyl | |
| 1231 | 3-Py | Et | (2,3-Dimethoxy)Phenyl | |
| 1233 | 3-Py | Et | (3-Trifluoromethoxy)Phenyl | |
| 1235 | 3-Py | Et | (3-Cyano)Phenyl | |
| 1236 | 3-Py | Et | (3,4-methylenedioxy)Phenyl | |
| 1237 | 3-Py | Et | (4-Methylthio)Phenyl | |
| 1238 | 3-Py | Et | (4-Ethoxy)Phenyl | |
| 1246 | $CF_3$ | Et | (4-Methoxycarbonyl)Phenyl | 93–95 |
| 1247 | $CF_3$ | Et | (3-Methyl)-2-thienyl | 93–95 |
| 1248 | $CF_3$ | Et | (5-Methyl)-2-thienyl | 87–89 |
| 1250 | 3-Py | Et | 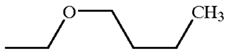 | |

TABLE 6-continued
L is —$NHCH_2$
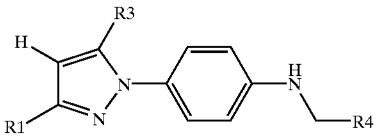
| CMPD # | $R_1$ | $R_3$ | $R_4$ | m.p. ° C. |
|---|---|---|---|---|
| 1252 | 3-Py | Et | (4-Trifluoromethyl)phenyl | |
| 1253 | 3-Py | Et | (2,5-Dimethoxy)Phenyl | |
| 1254 | 3-Py | Et | (4-Propyloxy)Phenyl | |
| 1255 | 3-Py | Et | cyclohexyl | |
| 1256 | 3-Py | Et | (2-Methoxy)Phenyl | |
| 1257 | 3-Py | Et | 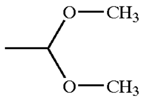 | |
| 1258 | 3-Py | Et | 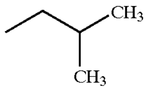 | |
| 1259 | 3-Py | Et | 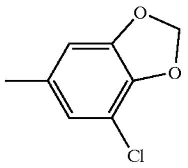 | |
| 1260 | 3-Py | Et | 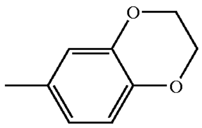 | |
| 1261 | 3-Py | Et | 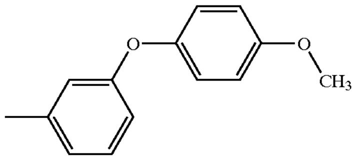 | |
| 1262 | 3-Py | Et | 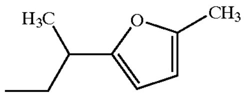 | |
| 1263 | 3-Py | Et | 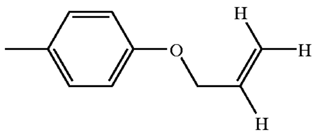 | |
| 1282 | 3-Py | Et | 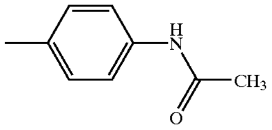 | |

TABLE 6-continued
L is —$NHCH_2$
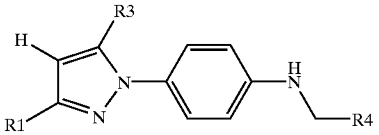
| CMPD # | $R_1$ | $R_3$ | $R_4$ | m.p. ° C. |
| --- | --- | --- | --- | --- |
| 1283 | 3-Py | Et | 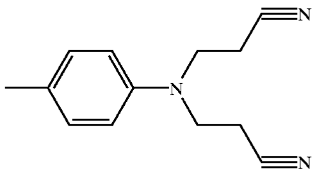 | |
| 1287 | 3-Py | Et | (2-Cyano)Phenyl | |
| 1288 | 3-Py | Et | 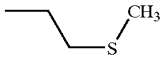 | |
| 1289 | 3-Py | Et | 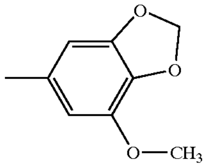 | |
| 1290 | 3-Py | Et | 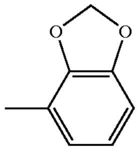 | |
| 1291 | 3-Py | Et | 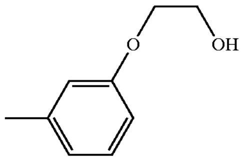 | |
| 1292 | 3-Py | Et | 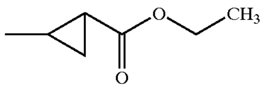 | |
| 1294 | 3-Py | Et | 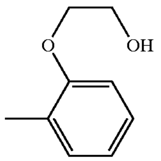 | |
| 1295 | 3-Py | Et | 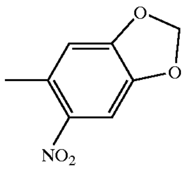 | |

TABLE 6-continued
L is —$NHCH_2$
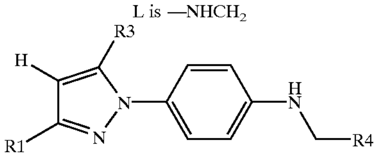
| CMPD # | $R_1$ | $R_3$ | $R_4$ | m.p. ° C. |
|---|---|---|---|---|
| 1296 | 3-Py | Et | 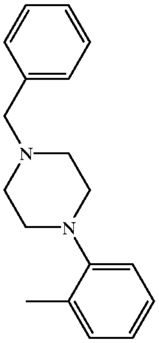 | |
| 1297 | 3-Py | Et | 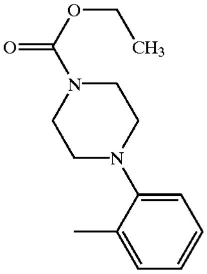 | |
| 1298 | 3-Py | Et | 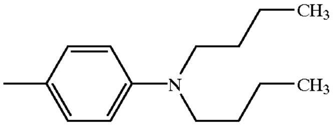 | |
| 1299 | 3-Py | Et | 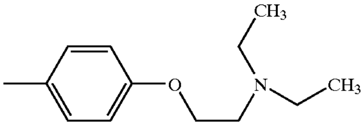 | |
| 1300 | 3-Py | Et | 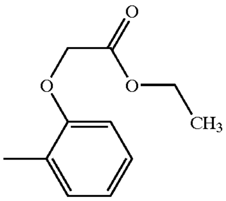 | |
| 1301 | 3-Py | Et | 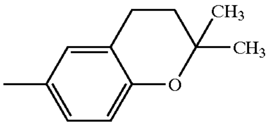 | |
| 1302 | 3-Py | Et | 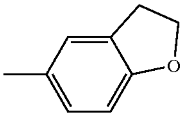 | |

TABLE 6-continued
L is —$NHCH_2$
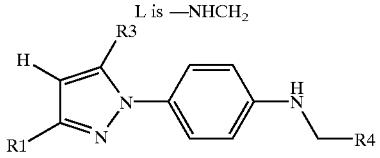
| CMPD # | $R_1$ | $R_3$ | $R_4$ | m.p. ° C. |
|---|---|---|---|---|
| 1303 | 3-Py | Et | 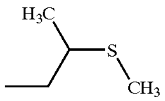 | |
| 1314 | 3-Py | Et | 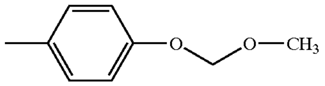 | |
| 1337 | 3-Py | Et | (3-Methyl)-2-thienyl | |
| 1376 | i-Pr | Et | (3-Methyl)-2-thienyl | |
| 1382 | 3-Py | Et | 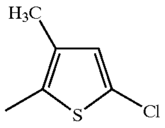 | |
| 1389 | 3-Py | Et | 2-thienyl | |
| 1396 | 3-Py | Et | (2-Methyl)-3-pyridinyl | |
| 1410 | 3-Py | Et | 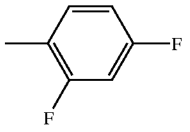 | 100–101 |
| 1411 | 3-Py | Et | 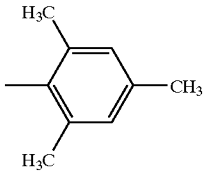 | 180–181 |
| 1413 | 3-Py | Et | (2-Chloro)-3-Pyridinyl | |
| 1417 | 3-Py | Et | 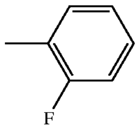 | |
| 1418 | 3-Py | Et | 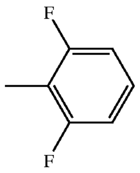 | |
| 1419 | 3-Py | Et | (2-Trifluoromethyl)Phenyl | |
| 1420 | 3-Py | Et | 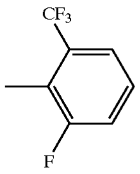 | |

TABLE 6-continued
L is —$NHCH_2$
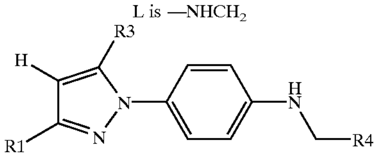
| CMPD # | $R_1$ | $R_3$ | $R_4$ | m.p. ° C. |
|---|---|---|---|---|
| 1421 | 3-Py | Et | (3,5-dimethyl)-4-isoxazolyl | |
| 1424 | 3-Py | Et | (2-Methyl)-3-furanyl | |
| 1425 | 3-Py | Et | (2-Ethyl)-Phenyl | |
| 1431 | 3-Py | Et | (5-Methyl)-4-isoxazolyl | |
| 1447 | 3-Py | CN | (3-Methyl)-2-thienyl | 136–137 |
| 1458 | 3-Py | Et | 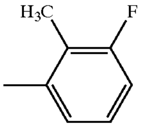 | 101–103 |
| 1459 | 3-Py | Et | 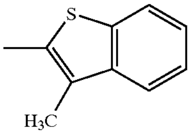 | 130 |
| 1460 | 3-Py | Et | 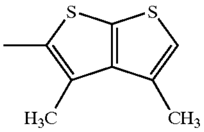 | 179–182 |
| 1461 | 3-Py | Et | 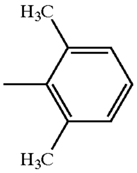 | 174–175 |
| 1462 | 3-Py | Et | 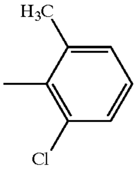 | 152–153 |
| 1470 | 3-Py | Et | cyclopentyl | |
| 1471 | 3-Py | Et | (2-Methyl)cyclohexyl | |
| 1472 | 3-Py | Et | (1-Methyl)cyclohexyl | |
| 1483 | 3-Py | Et | 3-Py | |
| 1487 | 3-Py | Et | 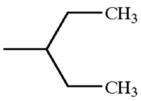 | 66–67 |
| 1488 | 3-Py | CN | 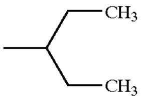 | 95–96 |
| 1490 | 3-Py | Et | 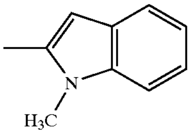 | 161–163 |

TABLE 6-continued

L is —$NHCH_2$

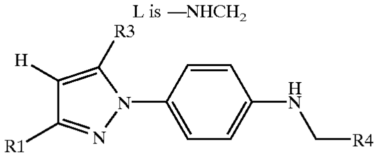

| CMPD # | $R_1$ | $R_3$ | $R_4$ | m.p. ° C. |
|---|---|---|---|---|
| 1491 | 3-Py | Et | 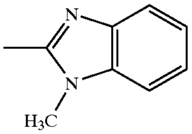 | |
| 1496 | 3-Py | Et | (3-Bromo)-2-thienyl | |
| 1499 | 3-Py | Et | 4-pyridinyl | |
| 1505 | 3-Py | Et | 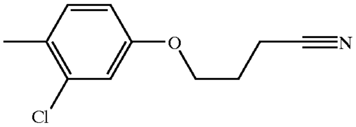 | |
| 1507 | 3-Py | CN | (2-methyl)phenyl | |
| 1514 | 3-Py | Et | 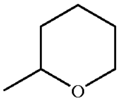 | |
| 1518 | 3-Py | CN | 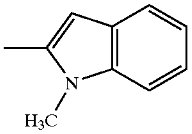 | 181 |
| 1520 | 3-Py | CN | Cyclopentyl | 131–133 |
| 1521 | 3-Py | Et | 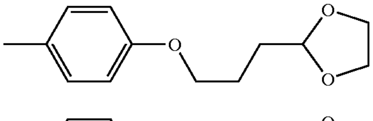 | 94–96 |
| 1522 | 3-Py | CN | 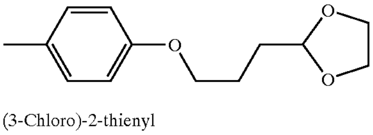 | 122–124 |
| 1525 | 3-Py | Et | (3-Chloro)-2-thienyl | |

Assessment of Biological Properties

IL-2 Promoter Assay

The IL-2 promoter assay measures transcriptional activation of a luciferase reporter gene which has been placed under control of the IL-2 promoter/enhancer. All the known regulatory features of the IL2gene are contained within a 300 bp sequence immediately upstream of the open reading frame. The region −328 to +35 relative to the transcription start site of the IL-2 gene is obtained by RT-PCR of human genomic DNA and is subcloned into the promoterless luciferase reporter vector pGL2-Basic (Promega). The resulting construct, pIL2P-luc, and a vector containing a neomycin resistance gene, pcDNA/Neo (Invitrogen), are linearized and stably transfected into Jurkat cells (a human T cell line) by electroporation. Following G-418 selection and dilution cloning, a cell line was established, J.1F/C6., which exhibited a strong induction of luciferase activity upon treatment with ionomycin and PMA (up to 100-fold), and potent inhibition by FK506 ($IC_{50}$=0.3 nM).

For screening compounds, the cells are pelleted by centrifugation, washed once with PBS, resuspended in RPMI (phenol red-free) containing 5% FBS, and dispensed into 96-well, white microtiter plates (Packard) at 50,000 cells/well. The cells are pre-incubated with compounds (1 $\mu$g/ml) for 15 min prior to addition of ionomycin (1 $\mu$g/ml) and PMA (10 ng/ml) in a final volume of 100 $\mu$l. Following a 5 hr incubation at 37° C. in a humidified incubator, 100 $\mu$l of Luc-Lite lysis buffer/luciferase assay buffer (Promega) is added and luminescence measured using a Packard Top-Count scintillation counter/luminometer.

Representatives from the synthetic examples and the Tables above were screened in this assay and had $IC_{50}$s below 10 microM IL-2 Production Assay Human peripheral blood is obtained from healthy donors by venipuncture and the mononuclear cell fraction is prepared by centrifugation on Ficoll Hypaque (Phamacia) density gradients. Contaminating red blood cells are lysed and the CD3+/CD4+ cells are purified using immunoaffinity columns (R&D Systems or CellPro). The cells are resuspended and dispensed in 96 well microtiter plates. Test compounds are added to the cells approximately 15 minutes prior to stimulation with ionomycin (1 $\mu$g/ml) and PMA (10 ng/ml). The final volume of the assay is 100 $\mu$L. Following a 16 hr incubation at 37° C., the cells are pelleted by centrifugation, and the supernatants are collected and stored at −70° C. until assayed for IL-2 using a commercial ELISA kit (Genzyme).

Representatives from the synthetic examples and theTables above were screened in this assay and had $IC_{50}$s below 10 microM Allogeneic Cell Transplant Response in Mice The ability of cells to recognize other cells from self or from another genetically different individual (non-self) is an important property in maintaining the integrity of tissue and organ structure. The allogeneic cell transplant response is therefore an important model for studies of transplant rejection. This T-cell-mediated immune response can be induced in adult mice by the injection of lymphocytes from an histoincompatible mouse strain. This response is characterized by T cell proliferation which is limited to the popliteal lymph node that receives drainage from the footpad area. No in vitro system exists that can exactly duplicate completely this in vivo response. The assay is commonly used to evaluate new and novel potential immunosuppressive molecules. The assay is preferred to the local GVH response in mice because the magnitude of the response is significantly greater (Kroczek et al., *J. Immunology*, 139, 3597 (1987)).

Experiments are conducted using male or female mice (20–26 grams). Any histoincompatible mouse strains suffice for donor and recipient populations. Typically DBA mice are used as donors and C57B1/6 mice are used as recipients. A minimum of 1 week stabilization and conditioning period is usually required before use of the mice. Each study utilizes approximately 36 recipient mice divided into groups of 6. Previous studies suggest this is the minimum number of animals which yields statistically significant results.

Donor mice are sacrificed by $CO_2$ asphyxiation and spleens are removed and a cell suspension is prepared. The cell suspension ($1.0\times10^7$/metatarsal in 0.05 ml) is injected I.D. into the dorsal metatarsal skin of recipient mice. Four days later, the animals are sacrificed by $CO_2$ asphyxiation and the popliteal nodes are removed and weighed. Groups of mice receiving putative immunosuppressive agents are dosed subcutaneously, intraperitoneally or orally one hour prior to cell injection and daily thereafter. The tests last approximately four days. The assay involves no footpad swelling and only a moderate increase in the size of the popliteal lymph node. The Student's t test is used to determine significant differences between popliteal lymph nodes of groups of untreated mice and those mice treated with putative immunosuppressive agents.

TABLE 7

Results of Allogenic Cell Transplant Model in Mice

| Cpd. # | Dose (mg/kg p.o., b.i.d.) | % Inhibition |
|---|---|---|
| 826 (Table 1) | 100 | 74 |

While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments that have been presented herein by way of example.

What is claimed is:

1. A compound of formula I'

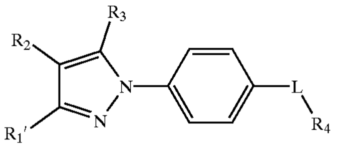

I' wherein:

$R_1'$ is aryl or heterocyclyl connected to the pyrazole in any position that makes a stable bond, optionally substituted with halogen, $C_{1-4}$ alkyl, $C_{1-4}$ alkenyl, CN, $Me_2N$, $CO_2Me$, OMe, aryl, heterocyclyl or $R_5$ (hereinafter defined);

$R_2$ is H, halogen, or methyl;

$R_3$ is $CF_3$, halogen, CN, $C_{1-8}$ alkyl or branched alkyl or $C_{1-8}$ alkenyl or branched alkenyl or $C_{3-8}$ cycloalkyl optionally substituted with OH, CN or methoxy; $C_{1-8}$ alkoxy, $C_{1-4}$ alkyloxyalkyl, $C_{1-8}$ alkylthio, $C_{1-4}$ alaylthioalkyl, $C_{1-8}$ dialkylamino $C_{1-4}$ dialkylaminoalkyl, $CO_2R_5$ where $R_5$ is $C_{1-4}$ alkyl or $C_{1-4}$alkenyl optionally substituted with carbocyclyl or heterocyclyl; aryl or heterocyclyl connected to the pyrazole in any position that makes a stable bond, optionally substituted with halogen, $C_{1-4}$ alkyl, $C_{1-4}$ alkenyl, CN, $Me_2N$, $CO_2Me$, OMe, aryl, heterocyclyl or $R_5$;

L is —NHC(O)—, —NHC(O)O—, —NHC(O)C(O)—, —NHC(S)—, —NH—, —NHC(O)NH, NHC(S)NH, $NECH_2$, —$NHCH(R_6)$—, where $R_6$ is H, CN, $C_{1-6}$ alkyl, $C_{1-6}$ alkyloxyoalyl $C_{1-6}$ alkythioalkyl, $C_{1-6}$ alkylsnylalkyl, $C_{1-6}$ alkylsulfonylalkyl, $C_{3-6}$ cycloalkyl, or heterocyclyl or aryl optionally substituted with a halogen, $C_{1-4}$ alkyl, CN, $Me_2N$, $CO_2Me$ or OMe, or —$NHC(R_6)$-lower alkyl;

$R_4$ is $C_{1-8}$ alkyl, $C_{1-8}$ alkyloxy, $C_{1-8}$ akylthio, $C_{1-8}$ alkylamino, $C_{1-4}$ alkoxyayl, $C_{1-4}$ allthioalkl, $C_{1-4}$ alkylarninoll, $C_{1-4}$ dialkylaminoalkyl, carbocyclyl or heterocyclyl, optionally substituted with one or more halogen, —CN, —$NO_2$, $SO_2NH_2$, or $R_7$ where $R_7$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkylsulfinylalkyl, $C_{1-6}$ alkylsulfonylalkyl or $C_{2-6}$ alkynyl, optionally substituted with halogen, OH, alkyloxy, CN, COO-lower alkyl, —CONH-lower alkyl, —CON(lower $alkyl)_2$, dialkylamino, phenyl or heterocylcyl; $CO_2R_7$, —$N(R_7)_2$, —$NH(R_7)$, —$C(O)R_7$, —$OR_7$, $S(O)_nR_7$ where n is 0, 1 or 2, —$SO_2NHR_7$, or —$SO_2N(R_7)_2$, wherein heterocyclyl refers to unsubstituted heterocycle radicals, those radicals that are partially or fully halogenated and those radicals substituted with alkyl, hydroxyl, nitro, —COOH, —CO (lower alkoxy), —CO (lower alkyl), amino, alkylamino, dialkylamino, alkoxy, —NCHO, —NCO (lower alkyl), —$NSO_2$—Ph $(halo)_{0\text{-}3}$, Ph, —O—Ph, naphthyl, —O-naphthyl, pyrrolyl, pyrrolyl substituted with lower alkyl, pyridyl, pyrazinyl, pyrimidinyl and pyridazinyl wherein heterocycle means benzimidazolyl, furyl; imidazolyl, imidazolinyl, imidazolidinyl, quinolinyl, isoquinolinyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiomorpholinyl, furyl, thienyl, thiazolyl, β-carbolinyl, tetrazolyl, thiazolidinyl, benzofuranoyl, thiamorpholinyl, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, tetrahydrothiophenyl and sulfolanyl.

2. The compound as recited in claim 1 wherein:

$R_1$' is heterocyclyl optionally substituted with halogen, $C_{1\text{-}4}$ alkyl, CN, alkoxy or $Me_2N$;

$R_2$ is H; and $R_3$ is halogen, Me, Et, $CF_3$, CN, cyclopropyl, vinyl, SMe, OMe, heterocyclyl or aryl optionally substituted with halogen, $C_{1\text{-}4}$ alkyl, CN, alkoxy or $Me_2N$;

L is —NHC(O)—, —NH—, —NHC(O)NH, —C(O)NH, or —$NHCH(R_6)$—, where $R_6$ is H, $C_{1\text{-}4}$ alkyl, or CN and $R_4$ is $C_{1\text{-}6}$ alkyl, $C_{1\text{-}4}$ alkyloxyalkyl, $C_{1\text{-}4}$ alkylioalkyl, cyclohexyl, cyclopentyl, indanyl, indolyl, phenyl, thienyl, naphthyl, isoxazolyl or pyridyl, optionally substituted with one or more halogen, —CN, —$NO_2$, $SO_2NH_2$, or $R_7$ where $R_7$ $C_{1\text{-}6}$ alkyl, $C_{2\text{-}6}$ alkenyl, $C_{1\text{-}6}$ alkyloxyalkyl, $C_{1\text{-}6}$ alkylthioalkyl, or $C_{2\text{-}6}$ alkynyl, optionally substituted with OH, CN, —COO-lower alkyl, —CONH-lower alkyl, —CON(lower $alkyl)_2$, dialkylo, or heterocylcyl; $CO_2R_7$, —$N(R_7)_2$, —NH $(R_7)$, —$C(O)R_7$, —$OR_7$, $S(O)_nR_7$ where n is 0, 1 or 2, —$SO_2NHR_7$, —$SO_2N(R_7)_2$.

3. The compound as recited in claim 1 wherein:

$R_1$' is 2-, 3-, or 4-pyridyl;

$R_2$ is H;

$R_3$ is CN, $CF_3$, Cl, Me, Et, cyclopropyl, vinyl, or 2-furanyl;

L is —NHC(O)—, —NH— or —$NHCH_2$—; and $R_4$ is a phenyl ring which is optionally substituted with one to three groups selected from $C_{1\text{-}3}$alkyl, chloro, fluoro, $CF_3$, $OC_{1\text{-}4}$alkyl, $OC_{3\text{-}5}$alkenyl, $CO_2C_{1\text{-}2}$alkyl, SMe, CN, $NO_2$, $NMe_2$ and $O(CH_2)_pR_{13}$, where p is 3 or 4 and $R_{13}$ is CN, $CO_2Me$, 2-(1,3-dioxolanyl), OH, or $OC_6H_5$; 1- or 2-indanyl, 2-tetrahydropyranyl, or a heterocycle selected from the group consisting of 2-thienyl, 3-furanyl, 3- or 4pyridyl, 4-isoxazlyl, 1-isoquinolinyl, 2-indolyl, 2-benzothienyl and 4-pyrazolyl, which may be optionally substituted with one to three groups selected from Cl, Br, Me, CN, $CF_3$, $OCF_3$, $NO_2$, or $O(CH_2)_pR_{13}$, where p is 3 or 4 and $R_{13}$ is CN, $CO_2Me$, 2-(1,3-dioxolanyl), OH, or $OC_6H_5$; $C_{5\text{-}6}$ alkyl, $C_{5\text{-}6}$cycloalkyl, or cyclohexenyl.

4. The compound as recited in claim 1 wherein:

$R_1$' is 3-pyridyl or 4-pyridyl;

$R_2$is H;

$R_3$ is CN, $CF_3$, Cl, Me or Et;

L is —NHC(O)—, —NH— or —$NHCH_2$—; and $R_4$is a phenyl ring which is optionally substituted with $O(CH_2)_3R_{13}$, where $R_{13}$ is CN, OH or 2-(1,3-dioxolanyl); $OC_{3\text{-}4}$alkyl, $O(CH_2)_4OH$, 1-pentenyl, one to three groups selected from Me, Cl, F and CN; 3-pyridyl optionally substituted in the 6-position with $O(CH_2)_2OEt$ or $O(CH_2)_3R_{13}$, where $R_{13}$ is CN, OH or 2-(1,3-dioxolanyl); 4-pyridinyl optionally substituted with a chlorine, 2-thienyl optionally substituted with Me or Br, 3,5-dimethyl-4-isoxazolyl, 1- methyl-2-indolyl, cyclopentyl, cyclohexyl, 1-indanyl or n-pent-3-yl.

5. A compound of formula I"

I"

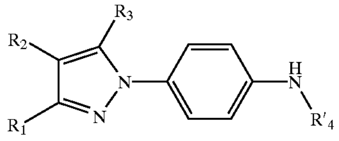

wherein:

$R_1$ and $R_3$ are the same or different and each is $CF_3$, halogen, CN, $C_{1\text{-}8}$ alkyl or branched alkyl or $C_{1\text{-}8}$ alkenyl or branched alkrenyl or $C_{3\text{-}8}$ cycloalkyl optionally substituted with OH, CN or methoxy; $C_{1\text{-}8}$ alkoxy, $C_{1\text{-}4}$ alkyloxyalkyl, $C_{1\text{-}8}$ alkylthio, $C_{1\text{-}4}$ alkylthioalkyl, $C_{1\text{-}8}$ dialkylamino, $C_{1\text{-}4}$ dialkylaminoalkyl, $CO_2R_5$ where $R_5$ is $C_{1\text{-}4}$ alkryl or $C_{1\text{-}4}$ alkenyl optionally substituted with carbocyclyl or heterocyclyl; aryl or heterocyclyl connected to the pyrazole in any position that makes a stable bond, optionally substituted with halogen, $C_{1\text{-}4}$ alkyl, $C_{1\text{-}4}$ alkenyl, CN, $Me_2N$, $CO_2Me$, OMe, aryl, heterocyclyl or $R_5$;

$R_2$ is H, halogen, or methyl; and $R_4$' is aryl, heterocyclyl or cycloalkyl, wherein heterocyclyl refers to unsubstituted heterocycle radicals, those radicals that are partially or fully halogenated and those radicals substituted with alkyl, hydroxyl, nitro, —COOH, —CO (Gower alkoxy), —CO (lower alkyl), amino, alkylamino, dialkylamino, alkoxy, —NCHO, —NCO (lower alkyl), —$NSO_2$—Ph $(halo)_{0\text{-}3}$, Ph, —O—Ph, naphthyl, —O-naphthyl, pyrrolyl, pyrrolyl substituted with lower alkyl, pyridyl, pyrazinyl, pyrimidinyl and pyridazinyl wherein heterocycle means benz imidazolyl, furyl; imidazolyl, imidazolinyl, imidazolidinyl, quinolinyl, isoquinolinyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiomorpholinyl, furyl, thienyl, thiazolyl, β-carbolinyl, tetrazolyl, thiazolidinyl, benzofuranoyl, thiamorpholinyl, benzoxazolyl, oxopiperidinyl, oxopyrroldinyl, oxoazepinyl, azepinyl, isoxazolyl, tetrahydropyranyl, tetrahydrofiuranyl, thiadiazoly, benzodioxolyl, tetrahydrothiophenyl and sulfolanyl, and with the proviso thai compounds of Formula I" in which $R_1$ is CN, $R_2$ is H, $R_3$ is 4-methylsulfonylphenyl and $R_4$ is either 4-methylaminophenyl or 4-ethylaminophenyl are excluded.

6. The compound as recited in claim 5 wherein:

$R_1$ is straight-chained, branched or cyclo-$C_{3\text{-}8}$ alkyl, alkenyl or alynyl; $C_{1\text{-}3}$ alkyloxyalkyl, $C_{1\text{-}5}$ alkyloxyl $C_{1\text{-}3}$alkylthioalkyl, $C_{1\text{-}5}$ alkylthio, $CF_3$; heterocyclyl or aryl optionally substituted with halogen, $C_{1\text{-}4}$ alkyl, CN, alkoxy or $Me_2N$;

$R_2$ is H; and $R_3$ is halogen, Me, Et, $CF_3$, CN, cyclopropyl, vinyl, SMe, OMe, heterocyclyl or aryl optionally substituted with halogen, $C_{1-4}$ alkyl, CN, alkoxy or $Me_2N$;

$R_4$' is cyclohexyl, cyclopentyl, indolyl, phenyl, thienyl, isoquinolyl, tetrahydropyranyl, naphthyl, or pyridyl, optionally substituted with one or more halogen, —CN, —$NO_2$, $SO_2NH_2$, or $R_7$ where $R_7$ is $C_{1-6}$ alkyl, $C_{2-6}$ alkenyl, $C_{1-6}$ alkyloxyalkyl, $C_{1-6}$ alkylthioalkyl, or $C_{2-6}$ alkynyl, optionally substituted with OH, CN, —COO-lower alkyl, —CONH-lower alkyl, —CON(lower alkyl)$_2$, dialkylamino, or heterocylcyl.

7. The compound as recited in claim 5 wherein:

$R_1$ is Et, i-Pr, n-Pr, t-Bu, cyclopentyl, $CF_3$, -OEt, $MeOCH_{2-}$, 2- or 3-tetrahydrofuranyl, 2-, 3-, or 4-pyridyl, 2-furanyl, or 2-thiazolyl;

$R_2$ is H;

$R_3$ is CN, $CF_3$, Cl, Me, Et, cyclopropyl, vinyl, or 2-furanyl; and $R_4$' is a phenyl ring which is optionally substituted with one to three groups selected from $C_{1-3}$alkyl, chloro, fluoro, $CF_3$, $OC_{1-4}$alkyl, $OC_{3-5}$alkenyl, $CO_2C_{1-2}$alkyl, SMe, CN, $NO_2$, $NMe_2$ and $O(CH_2)_pR_{13}$, where p is 3 or 4 and $R_{13}$ is CN, $CO_2Me$, 2-(1,3-dioxolanyl), OH, or $OC_6H_5$; isoquiniolyl; tetrahydropyranyl, 2-thienyl, 3- or 4-pyridyl, 1-isoquinolinyl, 2-indolyl, 2-benzothienyl and 4-pyrazolyl, which may be optionally substituted with one to three groups selected from Cl, Br, Me, CN, $CF_3$, $OCF_3$, $NO_2$, or $O(CH_2)_pR_{13}$, where p is 3 or 4 and $R_{13}$ is CN, $CO_2Me$, 2-(1,3-dioxolanyl), OH, or $OC_6H_5$; $C_{5-6}$cycloalkyl, or cyclohexenyl.

8. The compound as recited in claim 5 wherein:

$R_1$ is i-Pr, $CF_3$, 3-pyridyl or 4-pyridyl;

$R_2$ is H;

$R_3$ is CN, $CF_3$, Cl, Me or Et; and $R_4$' is a phenyl ring which is optionally substituted with $O(CH_2)_3R_{13}$, where $R_{13}$ is CN, OH or 2-(1,3-dioxolanyl); 3-pyridyl optionally substituted in the 6-position with $O(CH_2)_2OEt$ or $O(CH_2)_3R_{13}$, where $R_{13}$ is CN, OH or 2-(1,3-dioxolanyl); 4-pyridinyl optionally substituted with a chlorine; isoquinolyl, 2-thienyl optionally substituted with Me or Br; 1-methyl-2-indolyl; cyclopentyl, or cyclohexyl.

9. A pharmaceutical composition comprising a compound according to claim 1 and a pharmaceutically acceptable carrier adjuvant.

10. A pharmaceutical composition comprising a compound according to claim 5 and a pharmaceutically acceptable carrier or adjuvant.

11. A method of treating an inflammatory disease which comprises administering to a patient in need of such treatment a therapeutically effective amount of a compound according to claim 1.

12. A method of treating an inflammatory disease which comprises administering to a patient in need of such treatment-a therapeutically effective amount of a compound according to claim 5.

13. A compound selected from the group consisting of:

N-[4-(5-Ethyl-3-pyridin-3-yl-pyrazol-1-yl)phenyl]pyridine-3-carboxamide;

(2-Chloro-6-fluorobenzyl)-[4(5-ethyl-3pyridin-3-yl-pyrazol-1-yl)phenyl]amine;

(2-Methylbenzyl)-[4-(5-ethyl-3-pyridin-3-yl-pyrazol-1-yl)phenyl]amine;

[6-(3-Cyanopropoxy)pyridin-3-ylmethyl]-[4-(5-cyano-3-pyridin-3-yl-pyrazol-1-yl)phenyl]amine;

[6-(3-[1,3]Dioxolan-2-ylpropoxy)pyridin-3-ylmethyl]-[4(5-cyano-3-pyridin-3-yl-pyrazol-1-yl)phenyl]amine;

N-[4-(5-Ethyl-3-pyridin-3-yl-pyrazol-1-yl)phenyl]-1-methylindole-2-carboxarlide;

(2-Chloro-6-fluorobenzyl)-[4-(5-cyano-3-pyridin-3-yl-pyrazol-1-yl)phenyl]amine;

[4-(5-Cyano-3-pyridin-3-yl-pyrazol-1-yl)phenyl]-(2,6-dimethylbenzyl)-amine;

(2-Chloro-6-methylbenzyl)-[4-(5-cyano-3-pyridin-3-yl-pyrazol-1-yl)phenyl]amine;

[4-(5-Cyano-3-pyridin-3-yl-pyrazol-1-yl)phenyl]-(2-indanylmethyl)amine;

[4-(5-Ethyl-3-pyridin-3-yl-pyrazol-1-yl)phenyl]-(2-indanylmethyl)amine;

[4-(5-Ethyl-3-pyridin-3-yl-pyrazol-1-yl)phenyl]-(2-fluoro-6-methylbenzyl)amine;

4-(3-Cyanopropoxy)-N-[4-(5-cyano-3-pyridin-3-yl-pyrazol-1-yl)phenyl]benzamide;

N-[4-(5-cyano-3-pyridin-3-yl-pyrazol-1-yl)phenyl]-4-(3-[1,3]dioxolan-2-yl-propoxy)benzamide;

[4-(3-Cyanopropoxy)benzyl]-[4-(5-ethyl-3-pyridin-3-yl-pyrazol-1-yl)phenyl]amine;

[4-(3-Cyanopropoxy)benzyl]-[4-(5-cyano-3-pyridin-3-yl-pyrazol-1-yl)phenyl]amine.

14. 1-(Nitrophenyl)-3pyridin-3-yl)-1H-pyrazole-5-carbonitrile.

15. 1-(4Nitrophenyl)-3-(pyridin-3-yl)-5-ethyl-H-pyrazole.

* * * * *